US012053223B2

(12) United States Patent
Shelton, IV et al.

(10) Patent No.: US 12,053,223 B2
(45) Date of Patent: Aug. 6, 2024

(54) ADAPTIVE SURGICAL SYSTEM CONTROL ACCORDING TO SURGICAL SMOKE PARTICULATE CHARACTERISTICS

(71) Applicant: Cilag GmbH International, Zug (CH)

(72) Inventors: Frederick E. Shelton, IV, Hillsboro, OH (US); Andrew C. Deck, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 917 days.

(21) Appl. No.: 16/729,796

(22) Filed: Dec. 30, 2019

(65) Prior Publication Data
US 2021/0199557 A1  Jul. 1, 2021

(51) Int. Cl.
| | |
|---|---|
| *A61B 18/12* | (2006.01) |
| *A61B 1/04* | (2006.01) |
| *A61B 17/00* | (2006.01) |
| *A61B 18/00* | (2006.01) |
| *G01N 15/1434* | (2024.01) |
| *A61B 1/00* | (2006.01) |
| *A61B 34/30* | (2016.01) |
| *G01N 15/14* | (2006.01) |

(52) U.S. Cl.
CPC .......... *A61B 18/1206* (2013.01); *A61B 1/044* (2022.02); *A61B 1/046* (2022.02); *A61B 18/12* (2013.01); *G01N 15/1434* (2013.01); *A61B 1/000094* (2022.02); *A61B 2017/00061* (2013.01); *A61B 2017/00119* (2013.01); *A61B 2018/00642* (2013.01); *A61B 2018/00702* (2013.01); *A61B 2018/00773* (2013.01); *A61B 34/30* (2016.02); *G01N 2015/1486* (2013.01)

(58) Field of Classification Search
None
See application file for complete search history.

(56) References Cited

U.S. PATENT DOCUMENTS

| | | | |
|---|---|---|---|
| 3,901,602 A * | 8/1975 | Gravatt, Jr. | ............ G01N 21/53 356/439 |
| 4,753,641 A | 6/1988 | Vaslow | |
| 4,785,180 A | 11/1988 | Dietrich et al. | |
| 4,986,262 A | 1/1991 | Saito | |
| 5,434,667 A * | 7/1995 | Hutchins | ............ G01N 15/0205 356/336 |
| 5,460,182 A | 10/1995 | Goodman et al. | |
| 5,609,562 A | 3/1997 | Kaali | |
| 6,350,233 B1 | 2/2002 | Lubowski | |
| 6,386,758 B2 | 5/2002 | Loser | |

(Continued)

FOREIGN PATENT DOCUMENTS

| | | |
|---|---|---|
| CN | 109011149 A | 12/2018 |
| DE | 102015115903 A1 | 3/2017 |

(Continued)

OTHER PUBLICATIONS

Yi Liu et al, "Awareness of surgical smoke hazards and enhancement of surgical smoke prevention among the gynecologists," Jun. 2, 2019, IVYSPRING (Year: 2019).*

(Continued)

*Primary Examiner* — Linda C Dvorak
*Assistant Examiner* — Nicholas S Borsch

(57) ABSTRACT

Various control systems for controlling a surgical system according to detected airborne particulate characteristics are disclosed.

17 Claims, 36 Drawing Sheets

(56) References Cited

U.S. PATENT DOCUMENTS

| | | |
|---|---|---|
| 6,614,453 B1 | 9/2003 | Suri et al. |
| 6,632,183 B2 | 10/2003 | Bowman et al. |
| 6,804,012 B2 | 10/2004 | Gombert |
| 6,869,430 B2 | 3/2005 | Balbierz et al. |
| 6,951,535 B2 | 10/2005 | Ghodoussi et al. |
| 7,137,980 B2 | 11/2006 | Buysse et al. |
| 7,314,048 B2 | 1/2008 | Couture et al. |
| 7,477,931 B2 | 1/2009 | Hoyt |
| 7,516,675 B2 | 4/2009 | Kurtz et al. |
| 7,726,171 B2 | 6/2010 | Langlotz et al. |
| 7,740,623 B2 | 6/2010 | Nayak et al. |
| 7,766,210 B2 | 8/2010 | Shelton, IV et al. |
| 7,770,775 B2 | 8/2010 | Shelton, IV et al. |
| 7,798,385 B2 | 9/2010 | Boyden et al. |
| 7,810,691 B2 | 10/2010 | Boyden et al. |
| 7,901,353 B2 | 3/2011 | Vayser et al. |
| 7,905,840 B2 | 3/2011 | Pimenta et al. |
| 7,975,894 B2 | 7/2011 | Boyden et al. |
| 8,041,089 B2 | 10/2011 | Drumm et al. |
| 8,063,883 B2 | 11/2011 | Senft et al. |
| 8,073,528 B2 | 12/2011 | Zhao et al. |
| 8,079,950 B2 | 12/2011 | Stern et al. |
| 8,142,450 B2 | 3/2012 | Harris et al. |
| 8,161,977 B2 | 4/2012 | Shelton, IV et al. |
| 8,224,484 B2 | 7/2012 | Swarup et al. |
| 8,231,639 B2 | 7/2012 | Bolduc et al. |
| 8,523,043 B2 | 9/2013 | Ullrich et al. |
| 8,632,468 B2 | 1/2014 | Glossop et al. |
| 8,652,148 B2 | 2/2014 | Zuhars |
| 8,706,211 B2 | 4/2014 | Dacey, Jr. et al. |
| 8,755,576 B2 | 6/2014 | Taerum |
| 8,763,879 B2 | 7/2014 | Shelton, IV et al. |
| 8,820,603 B2 | 9/2014 | Shelton, IV et al. |
| 8,840,616 B2 | 9/2014 | Wilkinson et al. |
| 8,932,208 B2 | 1/2015 | Kendale et al. |
| 8,934,003 B2 | 1/2015 | Popovic et al. |
| 8,989,528 B2 | 3/2015 | Udd |
| 8,992,558 B2 | 3/2015 | Stone et al. |
| 9,005,118 B2 | 4/2015 | Selover et al. |
| 9,044,230 B2 | 6/2015 | Morgan et al. |
| 9,064,173 B2 | 6/2015 | Redden |
| 9,072,501 B2 | 7/2015 | Menchaca et al. |
| 9,072,535 B2 | 7/2015 | Shelton, IV et al. |
| 9,119,670 B2 | 9/2015 | Yang et al. |
| 9,141,868 B2 | 9/2015 | Xu et al. |
| 9,161,817 B2 | 10/2015 | Olson et al. |
| 9,161,820 B2 | 10/2015 | Mark et al. |
| 9,179,822 B2 | 11/2015 | Kitamura et al. |
| 9,179,890 B2 | 11/2015 | Ionasec et al. |
| 9,241,693 B2 | 1/2016 | Taylor et al. |
| 9,254,103 B2 | 2/2016 | Krishnaswamy et al. |
| 9,259,290 B2 | 2/2016 | Jenkins et al. |
| 9,265,587 B2 | 2/2016 | Vancamberg et al. |
| 9,274,047 B2 | 3/2016 | Velten et al. |
| 9,282,878 B2 | 3/2016 | Grey et al. |
| 9,295,773 B2 | 3/2016 | Prosl et al. |
| 9,326,770 B2 | 5/2016 | Shelton, IV et al. |
| 9,345,389 B2 | 5/2016 | Nie et al. |
| 9,402,726 B2 | 8/2016 | Linderman et al. |
| 9,480,534 B2 | 11/2016 | Bowling et al. |
| 9,547,940 B1 | 1/2017 | Sun et al. |
| 9,561,019 B2 | 2/2017 | Mihailescu et al. |
| 9,561,082 B2 | 2/2017 | Yen et al. |
| 9,597,054 B2 | 3/2017 | Kudavelly et al. |
| 9,649,109 B2 | 5/2017 | Ranucci et al. |
| 9,720,076 B2 | 8/2017 | Guo et al. |
| 9,730,690 B2 | 8/2017 | Shanley et al. |
| 9,760,989 B2 | 9/2017 | Yin et al. |
| 9,775,497 B2 | 10/2017 | Igarashi et al. |
| 9,788,851 B2 | 10/2017 | Dannaher et al. |
| 9,801,685 B2 | 10/2017 | Nguyen et al. |
| 9,855,317 B2 | 1/2018 | Bright |
| 9,857,167 B2 | 1/2018 | Jovanovski et al. |
| 9,883,857 B2 | 2/2018 | Shluzas et al. |
| 9,901,409 B2 | 2/2018 | Yang et al. |
| 9,911,187 B2 | 3/2018 | Steinle et al. |
| 9,918,640 B2 | 3/2018 | Ntziachristos et al. |
| 9,987,019 B2 | 6/2018 | Sato |
| 10,010,326 B2 | 7/2018 | Sato |
| 10,022,199 B2 | 7/2018 | Gassner et al. |
| 10,042,150 B2 | 8/2018 | Brown |
| 10,045,763 B2 | 8/2018 | Sato |
| 10,068,173 B2 | 9/2018 | Vayser et al. |
| 10,070,929 B2 | 9/2018 | Tanji |
| 10,085,611 B2 | 10/2018 | Yabe et al. |
| 10,105,470 B2 * | 10/2018 | Reasoner ............... A61B 50/10 |
| 10,123,706 B2 | 11/2018 | Elbaz et al. |
| 10,136,959 B2 | 11/2018 | Mintz et al. |
| 10,143,470 B2 | 12/2018 | Sato |
| 10,170,205 B2 | 1/2019 | Curd et al. |
| 10,194,981 B2 | 2/2019 | Margallo Balbas et al. |
| 10,194,990 B2 | 2/2019 | Amanatullah et al. |
| 10,219,738 B2 | 3/2019 | Monty et al. |
| 10,226,299 B2 | 3/2019 | Raffy et al. |
| 10,238,356 B2 | 3/2019 | Suzuki et al. |
| 10,255,723 B2 | 4/2019 | Thomas et al. |
| 10,314,463 B2 | 6/2019 | Agrawal et al. |
| 10,357,253 B2 | 7/2019 | Sato |
| 10,357,317 B2 | 7/2019 | Dupont et al. |
| 10,390,835 B2 | 8/2019 | Williams |
| 10,433,911 B2 | 10/2019 | Wang et al. |
| 10,467,752 B2 | 11/2019 | Tanji |
| 10,470,687 B2 | 11/2019 | Garbey et al. |
| 10,470,763 B2 | 11/2019 | Yates et al. |
| 10,506,991 B2 | 12/2019 | Govari |
| 10,510,149 B2 | 12/2019 | Cutu et al. |
| 10,512,518 B2 | 12/2019 | Vayser et al. |
| 10,531,074 B2 | 1/2020 | Wilson et al. |
| 10,546,423 B2 | 1/2020 | Jones et al. |
| 10,548,679 B2 | 2/2020 | Carlson et al. |
| 10,561,465 B2 | 2/2020 | Scholl et al. |
| 10,576,246 B2 | 3/2020 | Fischell et al. |
| 10,587,659 B2 | 3/2020 | Miller |
| 10,588,699 B2 | 3/2020 | Richmond et al. |
| 10,607,738 B2 | 3/2020 | Davidson et al. |
| 10,643,371 B2 | 5/2020 | Bharadwaj et al. |
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,768,402 B2 | 9/2020 | Brown |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,898,064 B2 | 1/2021 | Atarot et al. |
| 10,925,465 B2 | 2/2021 | Tully et al. |
| 10,925,598 B2 | 2/2021 | Scheib et al. |
| 10,945,787 B2 | 3/2021 | Fischell et al. |
| 10,945,796 B2 | 3/2021 | Popovic et al. |
| 10,973,519 B2 | 4/2021 | Weir et al. |
| 10,980,420 B2 | 4/2021 | Fengler et al. |
| 10,986,999 B2 | 4/2021 | Frangioni et al. |
| 10,987,176 B2 | 4/2021 | Poltaretskyi et al. |
| 11,000,270 B2 | 5/2021 | Scheib et al. |
| 11,006,100 B1 | 5/2021 | Douglas |
| 11,013,563 B2 | 5/2021 | Shelton, IV et al. |
| 11,020,016 B2 | 6/2021 | Wallace et al. |
| 11,058,501 B2 | 7/2021 | Tokarchuk et al. |
| 11,100,631 B2 | 8/2021 | Yates et al. |
| 11,109,866 B2 | 9/2021 | Shelton, IV et al. |
| 11,122,987 B2 | 9/2021 | Barash et al. |
| 11,204,322 B2 | 12/2021 | Kiselev et al. |
| 11,213,361 B2 | 1/2022 | Denlinger et al. |
| 11,219,501 B2 | 1/2022 | Shelton, IV et al. |
| 11,257,589 B2 | 2/2022 | Shelton, IV et al. |
| 11,269,173 B2 | 3/2022 | Komp et al. |
| 11,276,175 B2 | 3/2022 | Witte |
| 11,315,438 B1 | 4/2022 | Hannaford et al. |
| 11,410,259 B2 | 8/2022 | Harris et al. |

(56) References Cited

U.S. PATENT DOCUMENTS

| | | |
|---|---|---|
| 11,424,027 B2 | 8/2022 | Shelton, IV |
| 11,583,349 B2 | 2/2023 | Azizian et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0279354 A1 | 12/2005 | Deutsch et al. |
| 2006/0013454 A1 | 1/2006 | Flewelling et al. |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0227324 A1* | 10/2006 | Bloom .................. G01N 15/147 356/343 |
| 2006/0282096 A1 | 12/2006 | Papa et al. |
| 2006/0293557 A1 | 12/2006 | Chuanggui et al. |
| 2007/0014784 A1 | 1/2007 | Nayak et al. |
| 2007/0019781 A1 | 1/2007 | Haras |
| 2007/0040906 A1 | 2/2007 | Iketani |
| 2007/0066970 A1* | 3/2007 | Ineson ................ A61B 18/1206 606/1 |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0015664 A1 | 1/2008 | Podhajsky |
| 2008/0069433 A1 | 3/2008 | Corcoran et al. |
| 2008/0077158 A1 | 3/2008 | Haider et al. |
| 2008/0144906 A1 | 6/2008 | Allred et al. |
| 2008/0151233 A1 | 6/2008 | Blanke et al. |
| 2008/0194930 A1 | 8/2008 | Harris et al. |
| 2008/0205588 A1 | 8/2008 | Kim |
| 2008/0228104 A1 | 9/2008 | Uber et al. |
| 2008/0234866 A1 | 9/2008 | Kishi et al. |
| 2008/0269596 A1 | 10/2008 | Revie et al. |
| 2008/0297360 A1* | 12/2008 | Knox .................... G08B 25/10 340/628 |
| 2008/0319491 A1 | 12/2008 | Schoenefeld |
| 2009/0000627 A1 | 1/2009 | Quaid et al. |
| 2009/0012533 A1 | 1/2009 | Barbagli et al. |
| 2009/0234223 A1 | 9/2009 | Onoda et al. |
| 2009/0326336 A1 | 12/2009 | Lemke et al. |
| 2010/0030231 A1 | 2/2010 | Revie et al. |
| 2010/0036374 A1* | 2/2010 | Ward ................ A61B 18/1206 604/23 |
| 2010/0081875 A1 | 4/2010 | Fowler et al. |
| 2010/0087755 A1 | 4/2010 | Boezaart |
| 2010/0137882 A1 | 6/2010 | Quaid, III |
| 2010/0152539 A1 | 6/2010 | Ghabrial et al. |
| 2010/0194574 A1* | 8/2010 | Monk .................... G01S 17/88 340/627 |
| 2010/0217278 A1 | 8/2010 | Tripathi |
| 2010/0280493 A1 | 11/2010 | Nayak |
| 2011/0014181 A1 | 1/2011 | Thornton |
| 2011/0046476 A1 | 2/2011 | Cinquin et al. |
| 2011/0071531 A1 | 3/2011 | Carson |
| 2011/0082369 A1 | 4/2011 | Mohr et al. |
| 2011/0201881 A1 | 8/2011 | Emch |
| 2011/0257611 A1 | 10/2011 | Locke et al. |
| 2011/0257661 A1 | 10/2011 | Choi et al. |
| 2011/0306985 A1 | 12/2011 | Inoue et al. |
| 2012/0004894 A1 | 1/2012 | Butler et al. |
| 2012/0046668 A1 | 2/2012 | Gantes |
| 2012/0143341 A1 | 6/2012 | Zipnick |
| 2012/0165837 A1 | 6/2012 | Belman et al. |
| 2012/0265022 A1 | 10/2012 | Menn |
| 2012/0300051 A1 | 11/2012 | Daigo et al. |
| 2013/0035583 A1 | 2/2013 | Park et al. |
| 2013/0053679 A1 | 2/2013 | Owen |
| 2013/0090554 A1 | 4/2013 | Zvuloni et al. |
| 2013/0100250 A1 | 4/2013 | Raskar et al. |
| 2013/0172902 A1 | 7/2013 | Lightcap et al. |
| 2013/0211244 A1 | 8/2013 | Nathaniel |
| 2013/0274596 A1 | 10/2013 | Azizian et al. |
| 2013/0274673 A1 | 10/2013 | Fischell et al. |
| 2013/0274674 A1 | 10/2013 | Fischell et al. |
| 2013/0296712 A1 | 11/2013 | Durvasula |
| 2014/0005685 A1 | 1/2014 | Modrow et al. |
| 2014/0024945 A1 | 1/2014 | Mung et al. |
| 2014/0035762 A1 | 2/2014 | Shelton, IV et al. |
| 2014/0039520 A1 | 2/2014 | Haider et al. |
| 2014/0114180 A1 | 4/2014 | Jain |
| 2014/0148679 A1 | 5/2014 | Eary et al. |
| 2014/0163359 A1 | 6/2014 | Sholev et al. |
| 2014/0163664 A1 | 6/2014 | Goldsmith |
| 2014/0171793 A1 | 6/2014 | Lin et al. |
| 2014/0175150 A1 | 6/2014 | Shelton, IV et al. |
| 2014/0179997 A1 | 6/2014 | von Grunberg et al. |
| 2014/0267549 A1 | 9/2014 | Pinter et al. |
| 2014/0320684 A1 | 10/2014 | Chatenever et al. |
| 2014/0336461 A1 | 11/2014 | Reiter et al. |
| 2014/0378843 A1 | 12/2014 | Valdes et al. |
| 2015/0009473 A1 | 1/2015 | Su |
| 2015/0018999 A1 | 1/2015 | Lee et al. |
| 2015/0025548 A1 | 1/2015 | Franklin et al. |
| 2015/0032140 A1 | 1/2015 | Khouri |
| 2015/0051460 A1 | 2/2015 | Saxena et al. |
| 2015/0066107 A1 | 3/2015 | Richter et al. |
| 2015/0133909 A1 | 5/2015 | van der Weide et al. |
| 2015/0145966 A1 | 5/2015 | Krieger et al. |
| 2015/0202005 A1 | 7/2015 | Fuflyigin et al. |
| 2015/0209035 A1 | 7/2015 | Zemlok |
| 2015/0223903 A1 | 8/2015 | Bell et al. |
| 2015/0238071 A1 | 8/2015 | Hua et al. |
| 2015/0238276 A1 | 8/2015 | Atarot et al. |
| 2015/0243056 A1 | 8/2015 | Lee et al. |
| 2015/0245878 A1 | 9/2015 | Jaramaz et al. |
| 2015/0272557 A1 | 10/2015 | Overmyer et al. |
| 2015/0297177 A1 | 10/2015 | Boctor et al. |
| 2015/0305650 A1 | 10/2015 | Hunter et al. |
| 2015/0366628 A1 | 12/2015 | Ingmanson |
| 2015/0374435 A1 | 12/2015 | Cao et al. |
| 2016/0000516 A1 | 1/2016 | Cheng et al. |
| 2016/0007827 A1 | 1/2016 | Frimer et al. |
| 2016/0014328 A1 | 1/2016 | Rokutanda |
| 2016/0022146 A1 | 1/2016 | Piron et al. |
| 2016/0038004 A1 | 2/2016 | Tanaka |
| 2016/0070436 A1 | 3/2016 | Thomas et al. |
| 2016/0086380 A1 | 3/2016 | Vayser et al. |
| 2016/0135909 A1 | 5/2016 | Ogawa et al. |
| 2016/0183841 A1 | 6/2016 | Duindam et al. |
| 2016/0206204 A1 | 7/2016 | Matsuda et al. |
| 2016/0228090 A1 | 8/2016 | Boctor et al. |
| 2016/0235304 A1 | 8/2016 | Tzoumas et al. |
| 2016/0256101 A1 | 9/2016 | Aharoni et al. |
| 2016/0270861 A1 | 9/2016 | Guru et al. |
| 2016/0331467 A1 | 11/2016 | Slamin et al. |
| 2016/0338795 A1 | 11/2016 | Vayser et al. |
| 2016/0346034 A1 | 12/2016 | Arya et al. |
| 2017/0007350 A1 | 1/2017 | Popovic et al. |
| 2017/0020460 A1 | 1/2017 | Leblond et al. |
| 2017/0020613 A1 | 1/2017 | Kang et al. |
| 2017/0055819 A1 | 3/2017 | Hansen et al. |
| 2017/0059408 A1 | 3/2017 | Korner et al. |
| 2017/0071475 A1 | 3/2017 | Irisawa |
| 2017/0071688 A1 | 3/2017 | Cohen et al. |
| 2017/0079530 A1 | 3/2017 | DiMaio et al. |
| 2017/0099479 A1 | 4/2017 | Browd et al. |
| 2017/0165008 A1 | 6/2017 | Finley |
| 2017/0172382 A1 | 6/2017 | Nir et al. |
| 2017/0172662 A1 | 6/2017 | Panescu et al. |

(56) References Cited

U.S. PATENT DOCUMENTS

| | | |
|---|---|---|
| 2017/0180704 A1 | 6/2017 | Panescu et al. |
| 2017/0181808 A1 | 6/2017 | Panescu et al. |
| 2017/0181809 A1 | 6/2017 | Panescu et al. |
| 2017/0189006 A1 | 7/2017 | Shluzas et al. |
| 2017/0197028 A1 | 7/2017 | Goldsmith |
| 2017/0202624 A1 | 7/2017 | Atarot et al. |
| 2017/0238962 A1 | 8/2017 | Hansen et al. |
| 2017/0251900 A1 | 9/2017 | Hansen et al. |
| 2017/0258526 A1 | 9/2017 | Lang |
| 2017/0265943 A1 | 9/2017 | Sela et al. |
| 2017/0265947 A1 | 9/2017 | Dyer et al. |
| 2017/0296213 A1 | 10/2017 | Swensgard et al. |
| 2017/0304007 A1 | 10/2017 | Piron et al. |
| 2017/0312032 A1 | 11/2017 | Amanatullah et al. |
| 2017/0319057 A1 | 11/2017 | Inglese et al. |
| 2017/0366773 A1 | 12/2017 | Kiraly et al. |
| 2017/0367580 A1 | 12/2017 | DiMaio et al. |
| 2018/0000533 A1 | 1/2018 | Boll et al. |
| 2018/0014777 A1 | 1/2018 | Amir et al. |
| 2018/0014851 A1 | 1/2018 | Hansen et al. |
| 2018/0064498 A1 | 3/2018 | Kapadia et al. |
| 2018/0082480 A1 | 3/2018 | White et al. |
| 2018/0168741 A1 | 6/2018 | Swayze et al. |
| 2018/0214016 A1 | 8/2018 | Thommen et al. |
| 2018/0228555 A1 | 8/2018 | Charron et al. |
| 2018/0228559 A1 | 8/2018 | Brierton et al. |
| 2018/0235715 A1 | 8/2018 | Amiot et al. |
| 2018/0242967 A1 | 8/2018 | Meade |
| 2018/0247128 A1 | 8/2018 | Alvi et al. |
| 2018/0247153 A1 | 8/2018 | Ganapati et al. |
| 2018/0250086 A1 | 9/2018 | Grubbs |
| 2018/0271603 A1 | 9/2018 | Nir et al. |
| 2018/0271615 A1* | 9/2018 | Mahadik ............. A61M 13/003 |
| 2018/0333210 A1 | 11/2018 | Nijkamp et al. |
| 2018/0338806 A1 | 11/2018 | Grubbs |
| 2018/0343381 A1 | 11/2018 | Kobayashi et al. |
| 2018/0344140 A1 | 12/2018 | Aizenfeld |
| 2018/0368883 A1 | 12/2018 | Rossa et al. |
| 2019/0000478 A1 | 1/2019 | Messerly et al. |
| 2019/0008579 A1 | 1/2019 | Begg et al. |
| 2019/0022418 A1 | 1/2019 | Fishman |
| 2019/0046276 A1 | 2/2019 | Inglese et al. |
| 2019/0053691 A1 | 2/2019 | Hansen et al. |
| 2019/0053872 A1 | 2/2019 | Meglan |
| 2019/0059736 A1 | 2/2019 | Maier-Hein et al. |
| 2019/0069824 A1 | 3/2019 | Darty et al. |
| 2019/0076186 A1 | 3/2019 | Fischell et al. |
| 2019/0099070 A1 | 4/2019 | Mark et al. |
| 2019/0099226 A1 | 4/2019 | Hallen |
| 2019/0104919 A1 | 4/2019 | Shelton, IV et al. |
| 2019/0110924 A1 | 4/2019 | Moreno et al. |
| 2019/0117319 A1 | 4/2019 | Cima et al. |
| 2019/0125361 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125459 A1 | 5/2019 | Shelton, IV et al. |
| 2019/0142524 A1 | 5/2019 | Hladio et al. |
| 2019/0159848 A1 | 5/2019 | Quaid et al. |
| 2019/0172371 A1 | 6/2019 | Eckert et al. |
| 2019/0175272 A1 | 6/2019 | Khan et al. |
| 2019/0180865 A1 | 6/2019 | Kashima et al. |
| 2019/0192145 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201075 A1 | 7/2019 | Shelton, IV et al. |
| 2019/0201102 A1 | 7/2019 | Shelton, IV et al. |
| 2019/0201116 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205567 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0208641 A1 | 7/2019 | Yates et al. |
| 2019/0223961 A1 | 7/2019 | Barral et al. |
| 2019/0247050 A1 | 8/2019 | Goldsmith |
| 2019/0269476 A1 | 9/2019 | Bowling et al. |
| 2019/0279524 A1 | 9/2019 | Stoyanov et al. |
| 2019/0290524 A1 | 9/2019 | Augustine et al. |
| 2019/0293554 A1 | 9/2019 | Nakao et al. |
| 2019/0307524 A1 | 10/2019 | Popovic |
| 2019/0311542 A1 | 10/2019 | Douglas et al. |
| 2019/0320117 A1 | 10/2019 | Wu et al. |
| 2019/0320878 A1 | 10/2019 | Duindam et al. |
| 2019/0321118 A1 | 10/2019 | Genova et al. |
| 2019/0374140 A1 | 12/2019 | Tucker et al. |
| 2019/0388157 A1 | 12/2019 | Shameli et al. |
| 2020/0008879 A1 | 1/2020 | Popovic et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0030036 A1 | 1/2020 | Forstein |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0078120 A1 | 3/2020 | Aldridge et al. |
| 2020/0121245 A1 | 4/2020 | Barclay et al. |
| 2020/0188032 A1 | 6/2020 | Komp et al. |
| 2020/0222146 A1 | 7/2020 | Komp |
| 2020/0246073 A1 | 8/2020 | Rossetto et al. |
| 2020/0253669 A1 | 8/2020 | Diolaiti et al. |
| 2020/0271565 A1 | 8/2020 | Gütle et al. |
| 2020/0273577 A1 | 8/2020 | Wolf et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Denlinger et al. |
| 2020/0289230 A1 | 9/2020 | Denlinger et al. |
| 2020/0291476 A1 | 9/2020 | Deng et al. |
| 2020/0315721 A1 | 10/2020 | Rabindran et al. |
| 2020/0330166 A1 | 10/2020 | Meglan et al. |
| 2020/0345451 A1 | 11/2020 | Peine et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0045838 A1 | 2/2021 | Bradbury et al. |
| 2021/0068908 A1 | 3/2021 | Thienphrapa et al. |
| 2021/0137634 A1 | 5/2021 | Lang |
| 2021/0153943 A1 | 5/2021 | Piron et al. |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |

(56) References Cited

U.S. PATENT DOCUMENTS

| | | |
|---|---|---|
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0212794 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0275252 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307866 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |
| 2021/0315645 A1 | 10/2021 | Hares et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0079675 A1 | 3/2022 | Lang |
| 2022/0133412 A1 | 5/2022 | Tolkowsky et al. |
| 2022/0273288 A1 | 9/2022 | Scheib et al. |
| 2022/0323066 A1 | 10/2022 | Scheib et al. |
| 2023/0046220 A1 | 2/2023 | Scheib et al. |
| 2023/0074951 A1 | 3/2023 | Scheib et al. |

FOREIGN PATENT DOCUMENTS

| | | |
|---|---|---|
| EP | 2700365 A1 | 2/2014 |
| EP | 2754383 A2 | 7/2014 |
| EP | 3367387 A1 | 8/2018 |
| JP | 2006280591 A | 10/2006 |
| JP | 4106991 B2 | 6/2008 |
| KR | 20120068597 A | 6/2012 |
| WO | WO-2008033133 A2 | 3/2008 |
| WO | WO-2013093391 A1 | 6/2013 |
| WO | WO-2013163391 A1 | 10/2013 |
| WO | WO-2015135058 A1 | 9/2015 |
| WO | WO-2017042171 A1 | 3/2017 |
| WO | WO-2018171851 A1 | 9/2018 |
| WO | WO-2018200767 A1 | 11/2018 |
| WO | WO-2019130085 A1 | 7/2019 |
| WO | WO-2020116991 A1 | 6/2020 |

OTHER PUBLICATIONS

Kurata et al. "Time-of-flight Near-infrared Spectroscopy for Non-destructive Measurement of Internal Quality in Grapefruit," J. Amer. Soc. Hort. Sci. 138(3): 225-228, 2013.

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhajj, et al., "Sleeve Gastrectomy Surgical Assistive Instrument for Accurate Remnant Stomach Volume," ASME, J. Med. Devices, vol. 4, pp. 1-10, Jun. 2010.

Brecht, Hans-Peter et al., "Whole-body three-dimensional optoacoustic tomography system for small animals," Journal of Biomedical Optics, vol. 14, No. 6, 064007-1-064007-7 (2009).

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

Ueda et al., "Quantitative computed tomography for the prediction of pulmonary function after lung cancer surgery: a simple method using simulation software," European Journal of Cardio-thoracic Surgery, 35 (2009) 414-418.

Fuchs et al., "Three-dimensional visualization and virtual simulation of resections in pediatric solid tumors," Journal of Pediatric Surgery (2005) 40, 364-370.

Brainlab Ag: "iPLAN CRANIAL—Software user guide", Jan. 1, 2014, Retrieved from the internet: URL: https://userguides.brainlab.com/wp-content/uploads/2019/12/iPlan-Cranial-3.0-Software-User-Guide-English-60914-63EN-Rev.1.4.pdf, pp. 1-268 (Jan. 1, 2014).

* cited by examiner

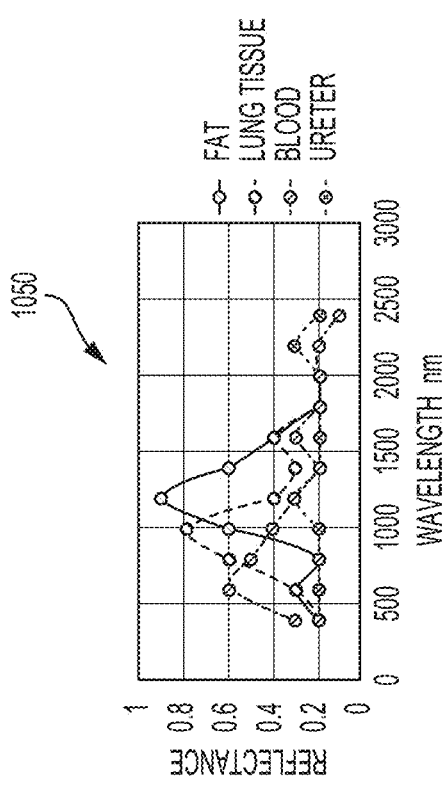
FIG. 13C
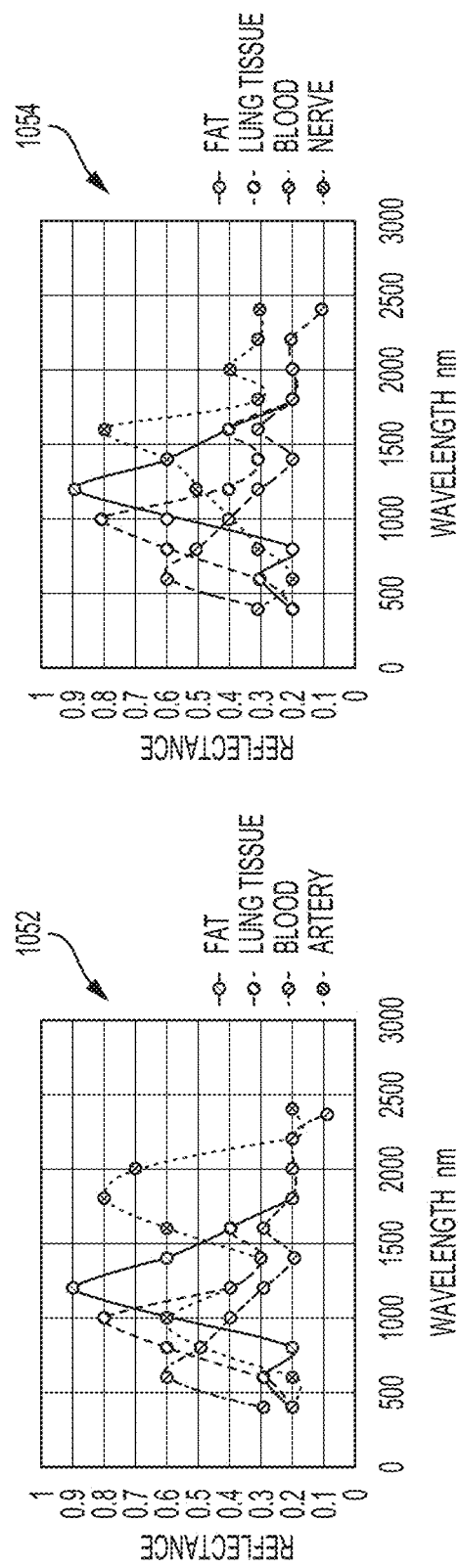
FIG. 13D
FIG. 13E

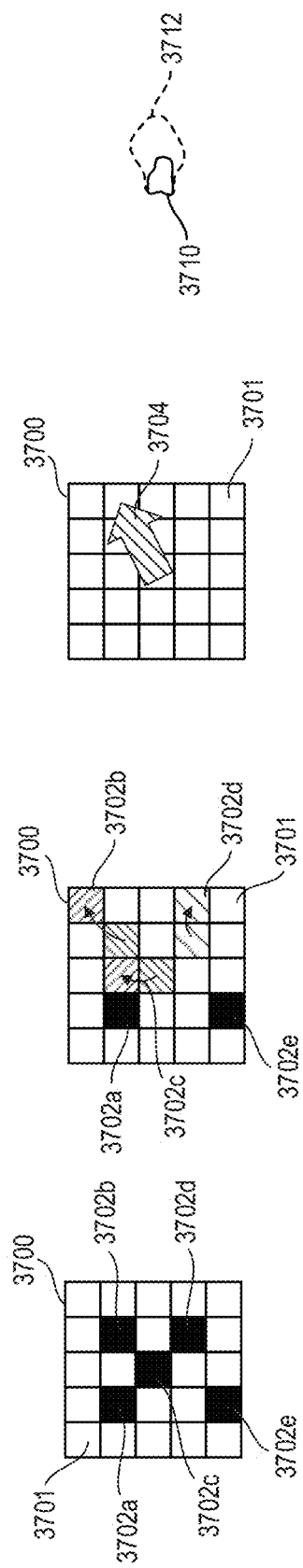

ADAPTIVE SURGICAL SYSTEM CONTROL ACCORDING TO SURGICAL SMOKE PARTICULATE CHARACTERISTICS

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In one general aspect, a control system for a surgical system is disclosed. The control system includes an imaging system and a control circuit coupled to the imaging system. The imaging system includes an emitter configured to emit electromagnetic radiation (EMR), a polarizing filter configured to polarize the EMR emitted by the emitter, and an image sensor. The control circuit is configured to detect the polarized EMR reflected from an airborne particulate as received by the image sensor, determine whether a particulate type of the airborne particulate is a naturally occurring particulate or a synthetic particulate based on a reflective characteristic of the polarized EMR, and adjust a control parameter of the surgical system according to the determined particulate type.

In another general aspect, a control system for a surgical system is disclosed. The control system includes an imaging system and a control circuit coupled to the imaging system. The imaging system includes a multispectral electromagnetic radiation (EMR) source, a polarizing filter configured to polarize EMR emitted by the multispectral EMR source, and an image sensor. The control circuit is configured to detect the polarized EMR reflected from a particulate in an aerosol as received by the image sensor, determine whether a particulate type of the particulate is a naturally occurring particulate or a synthetic particulate based on a reflective characteristic of the polarized EMR, determine whether to adjust a first control parameter or a second control parameter according to the determined particulate type, and adjust the first control parameter or the second control parameter accordingly.

In yet another general aspect, a control system for a surgical system is disclosed. The control system includes an imaging system and a control circuit coupled to the imaging system. The imaging system includes a multispectral electromagnetic radiation (EMR) source, a polarizing filter configured to polarize EMR emitted by the multispectral EMR source, and an image sensor. The control circuit is configured to detect the polarized EMR reflected from a particulate in an aerosol as received by the image sensor, determine whether a particulate type of the particulate is a naturally occurring particulate or a synthetic particulate based on a reflective characteristic of the polarized EMR, determine whether to adjust a first control parameter or a second control parameter according to the determined particulate type, and adjust the first control parameter or the second control parameter accordingly.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIGS. 13C-13E depict illustrative hyperspectral identifying signatures to differentiate anatomy from obscurants, wherein FIG. 13C is a graphical representation of a ureter signature versus obscurants, FIG. 13D is a graphical representation of an artery signature versus obscurants, and FIG. 13E is a graphical representation of a nerve signature versus obscurants, according to at least one aspect of the present disclosure.

Figure 14:
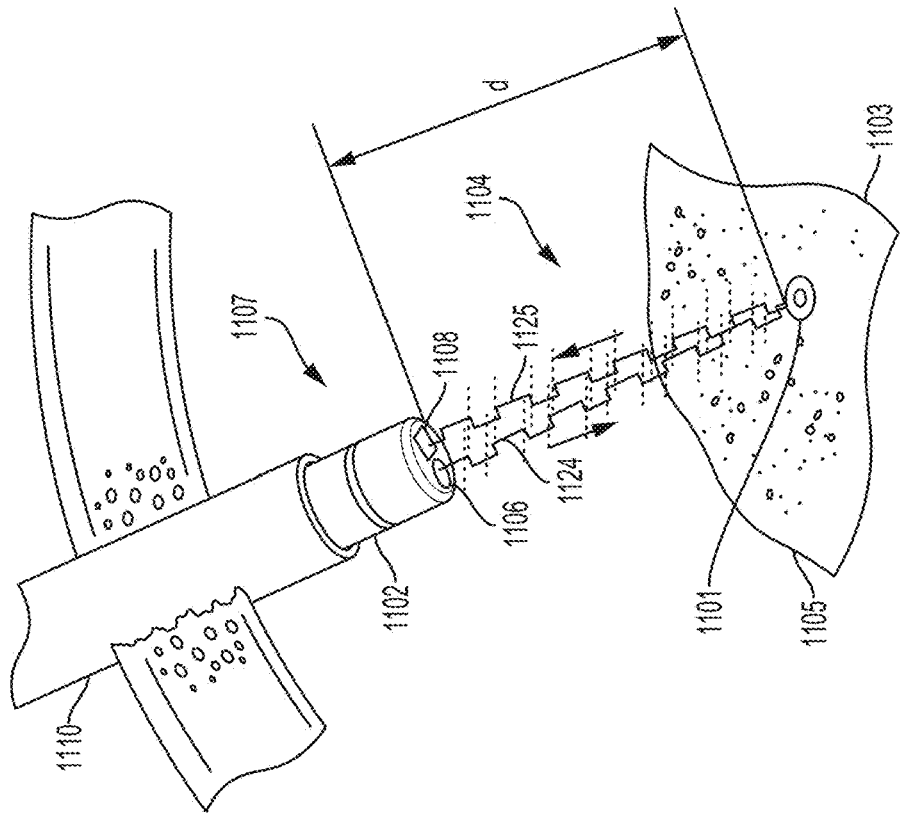

FIG. 14 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 15:
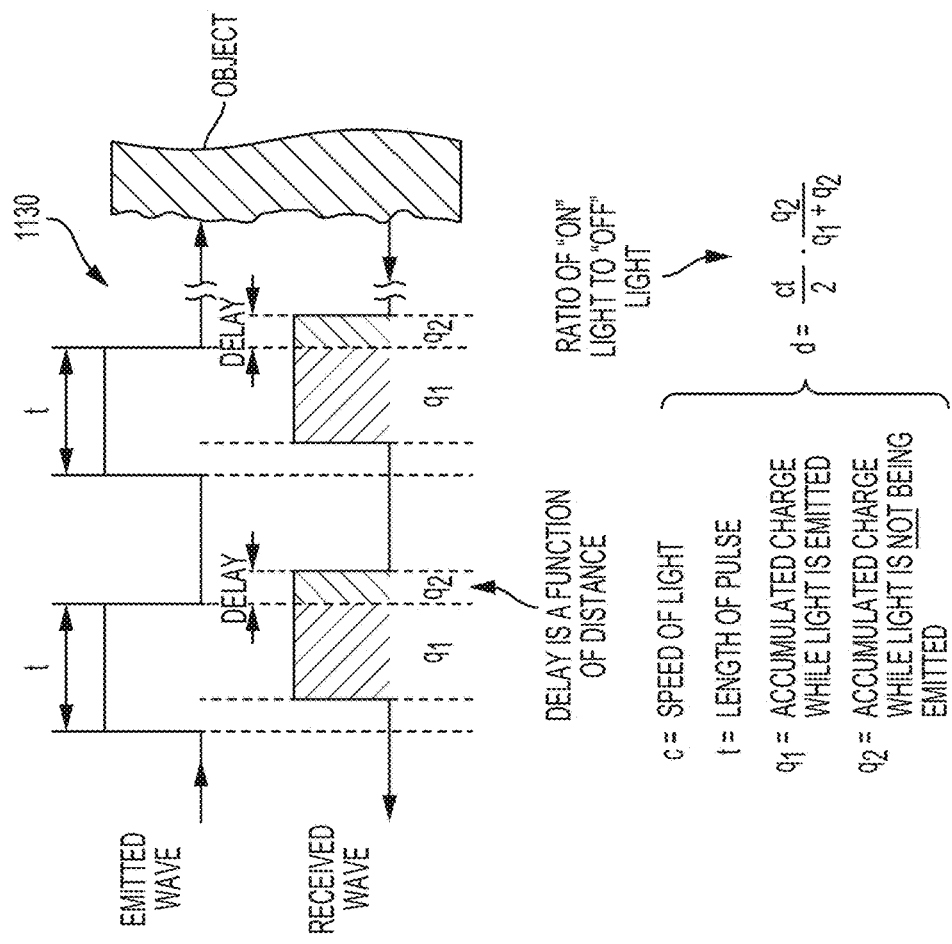

FIG. 15 is a schematic of an emitted wave, a received wave, and a delay between the emitted wave and the received wave of the NIR time-of-flight measurement system of FIG. 17A, according to at least one aspect of the present disclosure.

Figure 16:
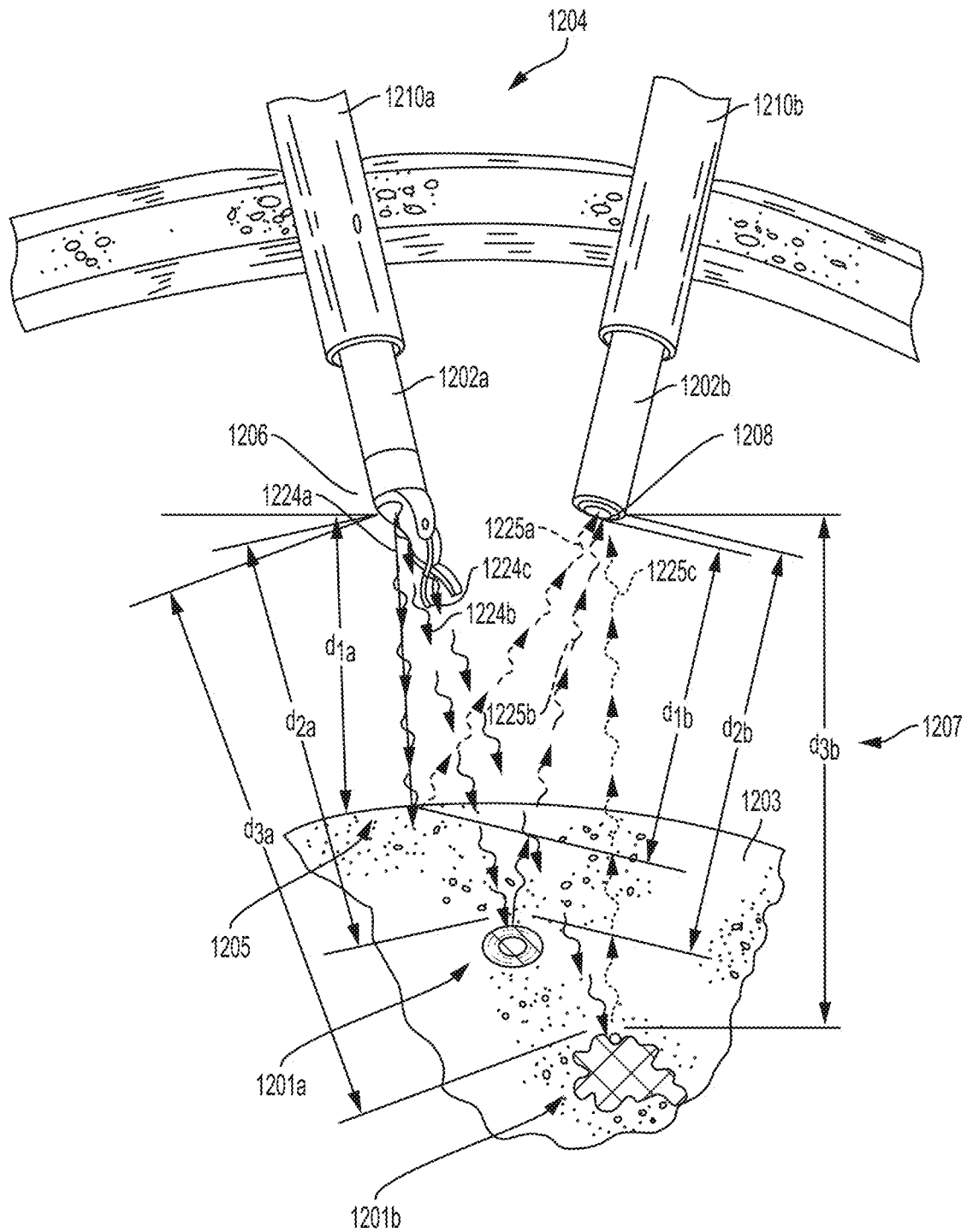

FIG. 16 illustrates a NIR time-of-flight measurement system configured to sense a distance to different structures, the time-of-flight measurement system including a transmitter (emitter) and a receiver (sensor) on separate devices, according to at least one aspect of the present disclosure.

Figure 17:
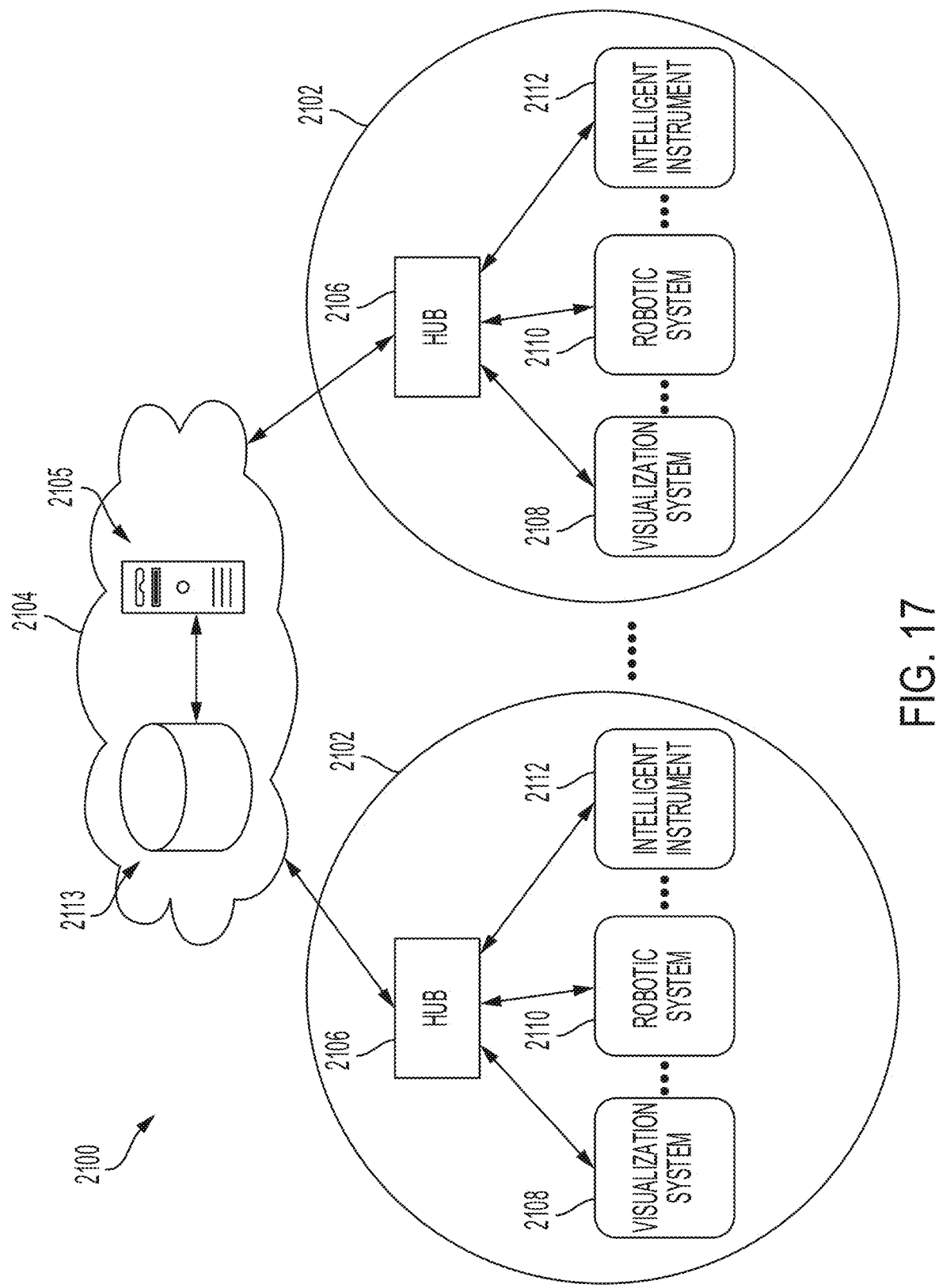

FIG. 17 is a block diagram of a computer-implemented interactive surgical system, according to at least one aspect of the present disclosure.

Figure 18:
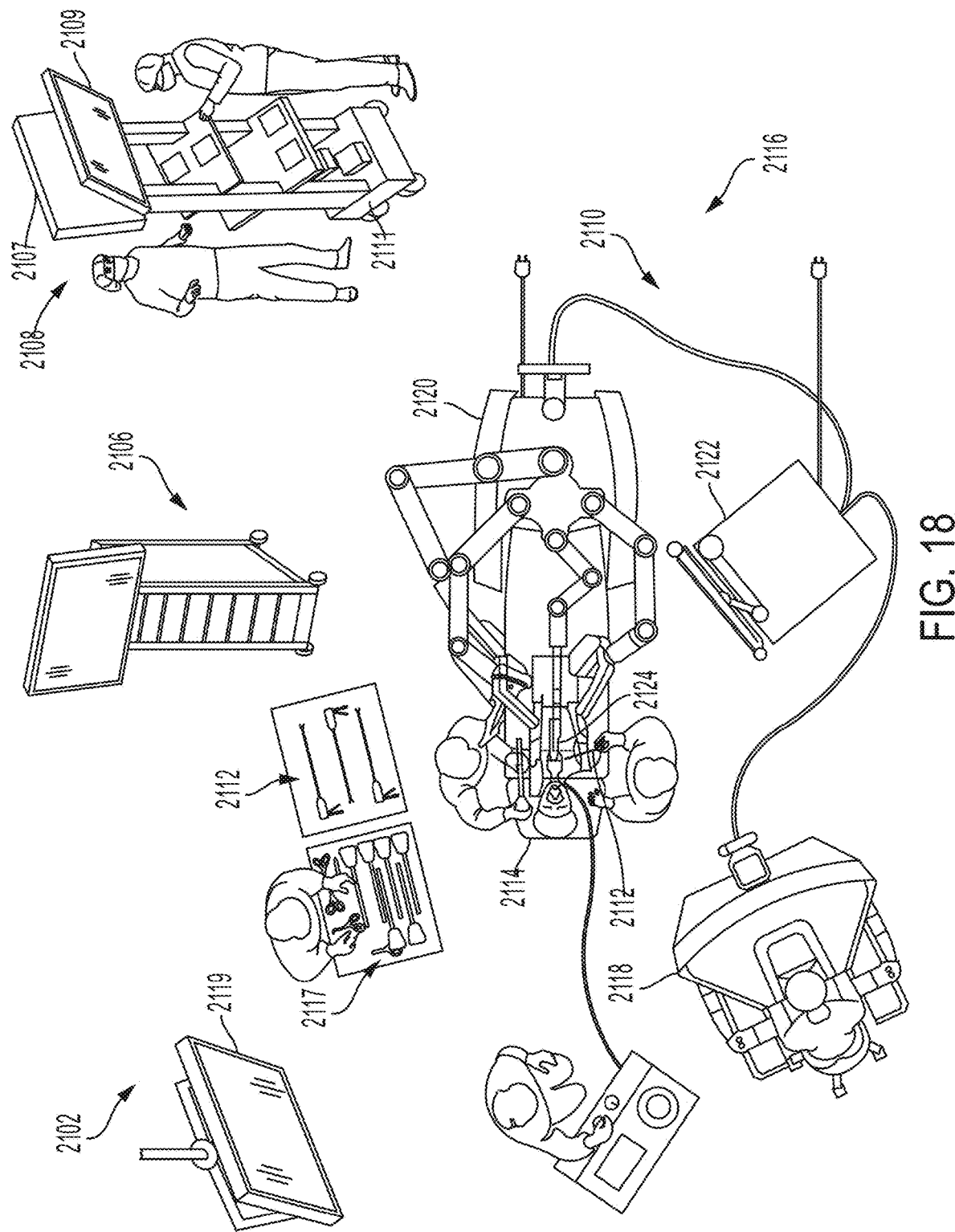

FIG. 18 is a surgical system being used to perform a surgical procedure in an operating room, according to at least one aspect of the present disclosure.

Figure 19:
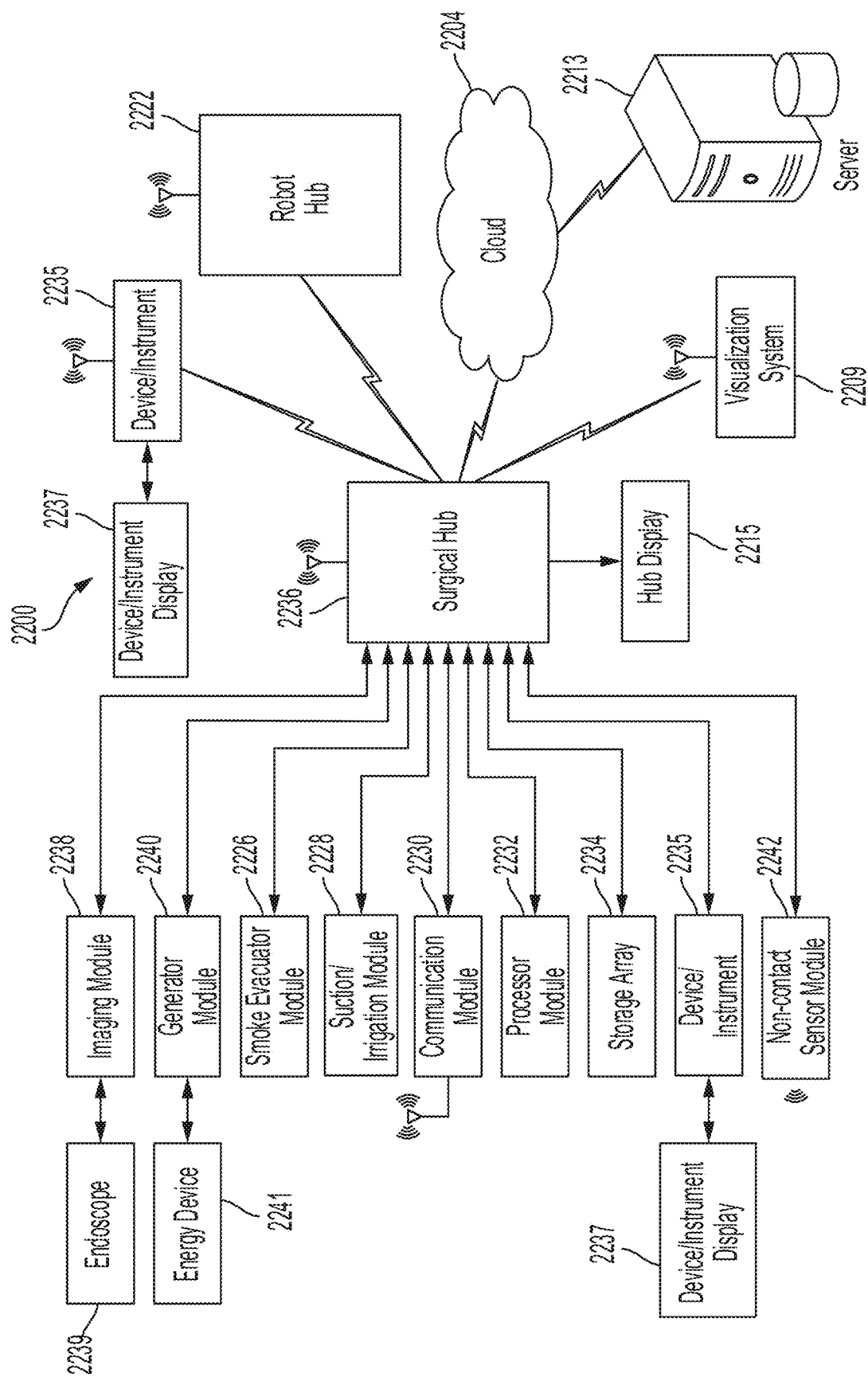

FIG. 19 illustrates a computer-implemented interactive surgical system, according to at least one aspect of the present disclosure.

Figure 20:
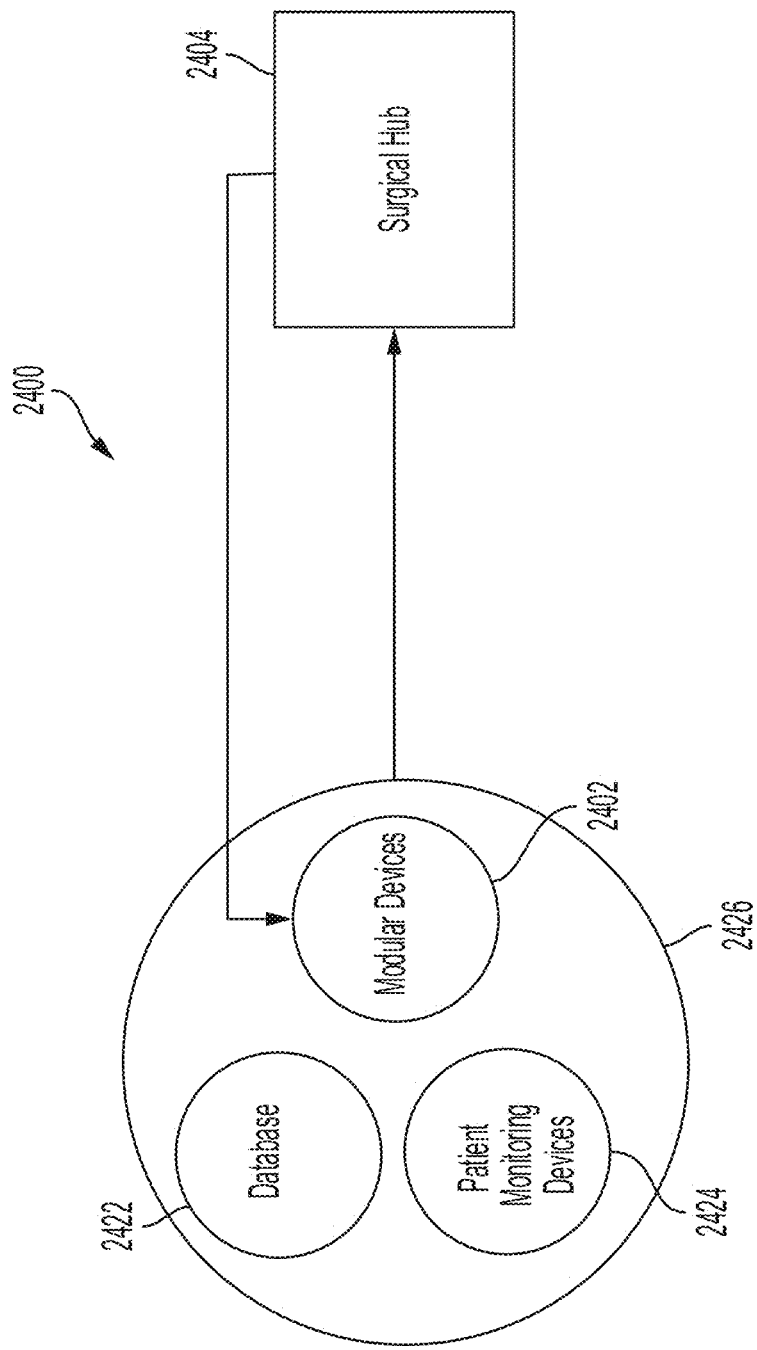

FIG. 20 illustrates a diagram of a situationally aware surgical system, according to at least one aspect of the present disclosure.

Figure 21:
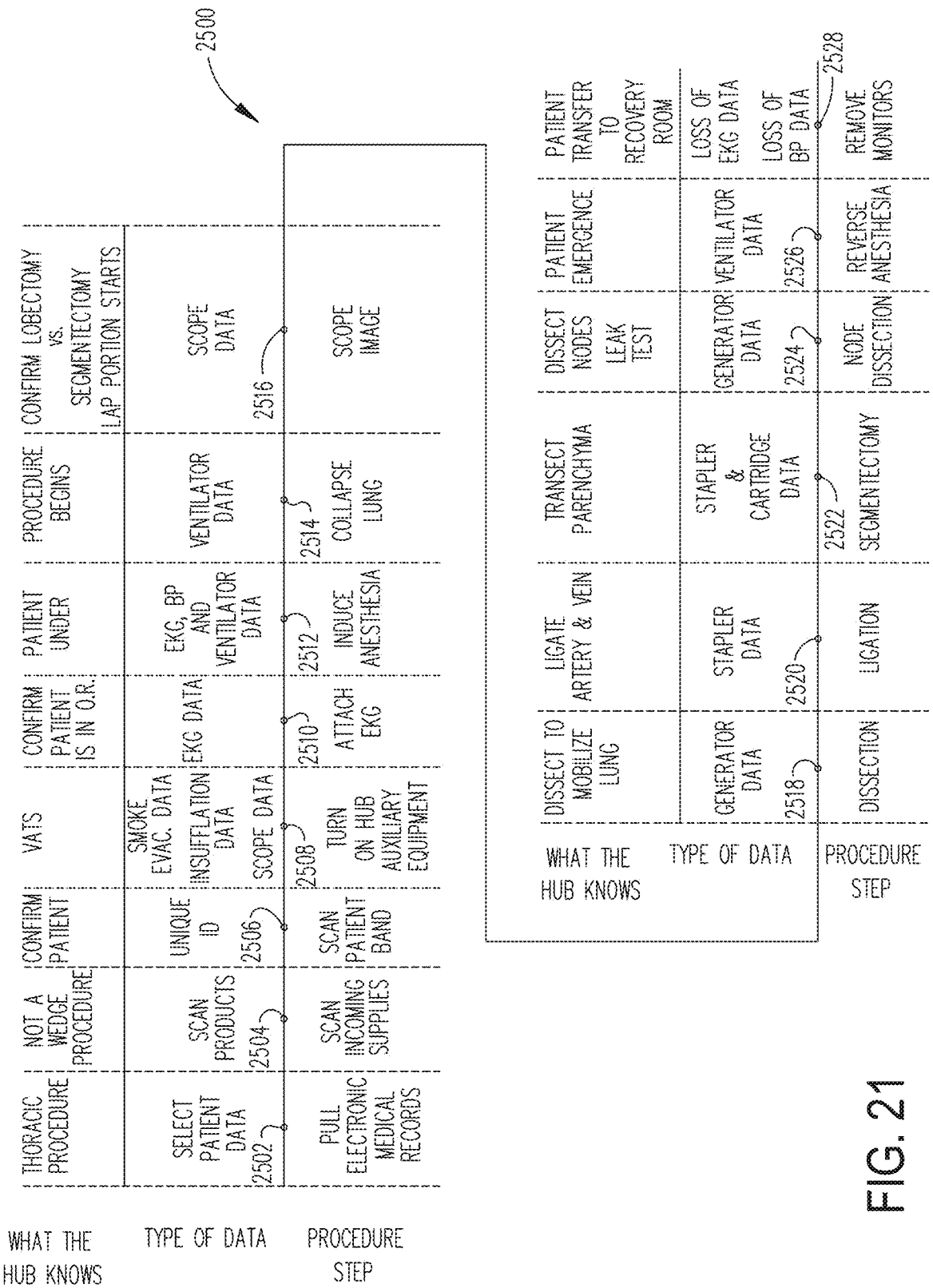

FIG. 21 illustrates a timeline depicting situational awareness of a hub, according to at least one aspect of the present disclosure.

Figure 22:
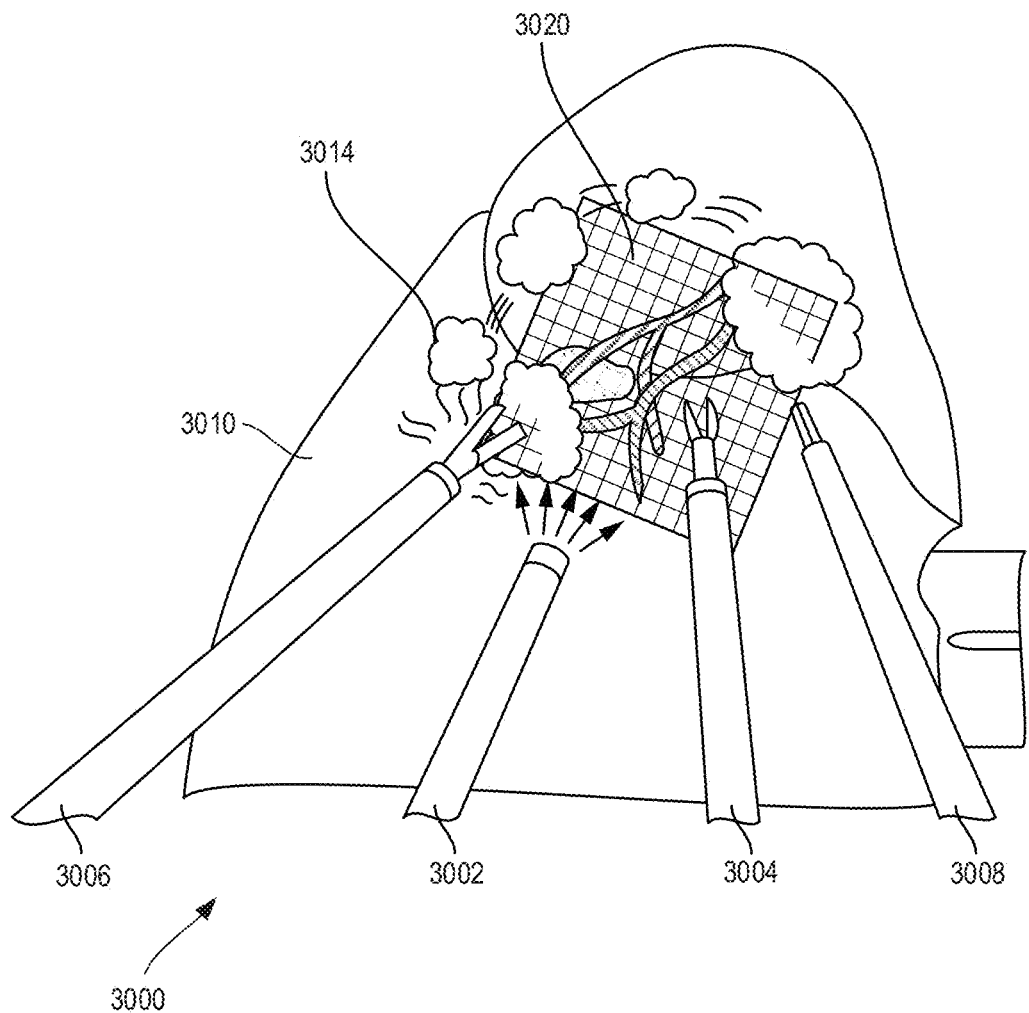

FIG. 22 is a diagram of a surgical system during the performance of a surgical procedure, in accordance with at least one aspect of the present disclosure.

Figure 23:
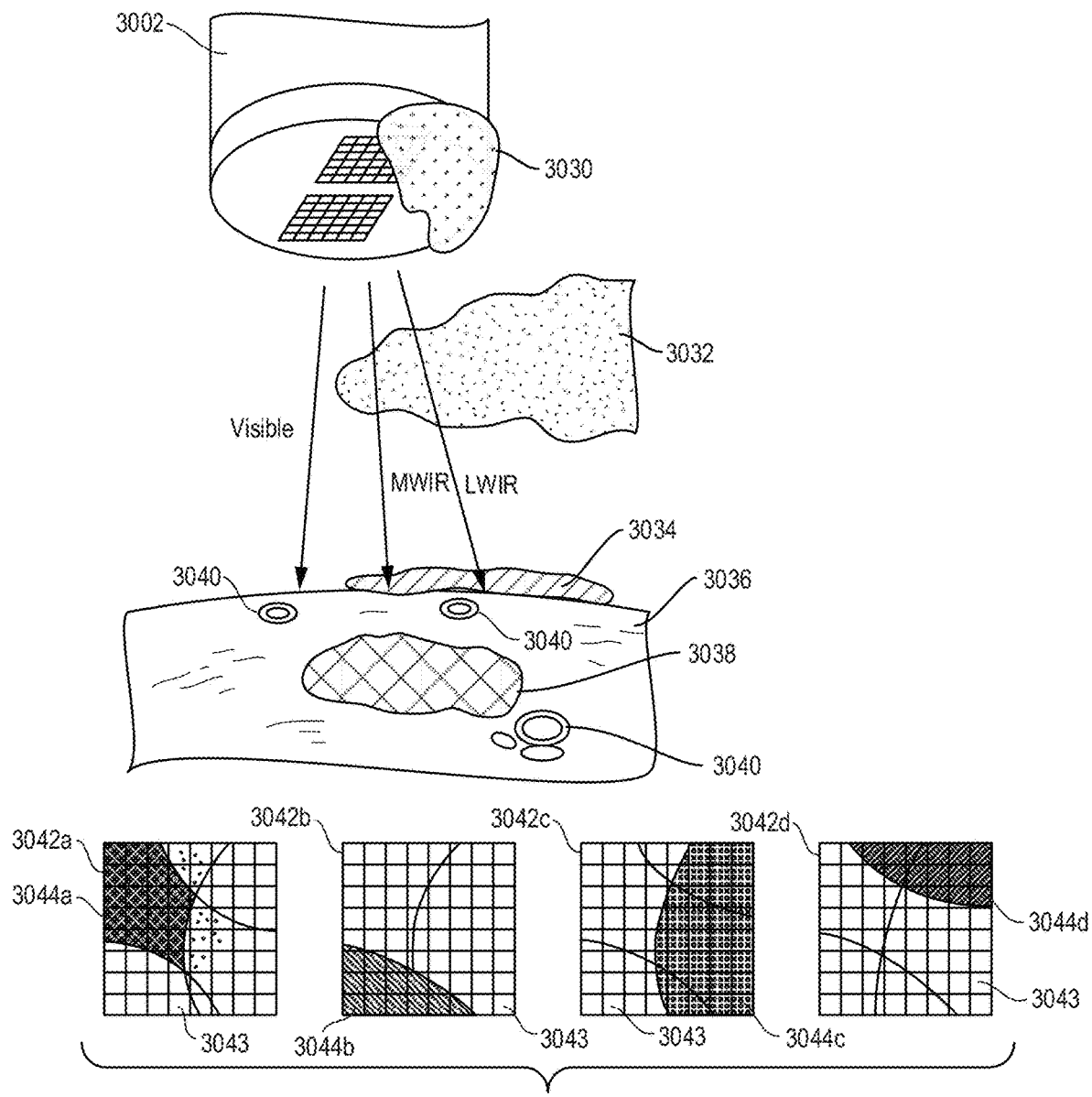

FIG. 23 is a diagram of an imaging device faced with multiple obscurants, in accordance with at least one aspect of the present disclosure.

Figure 24:
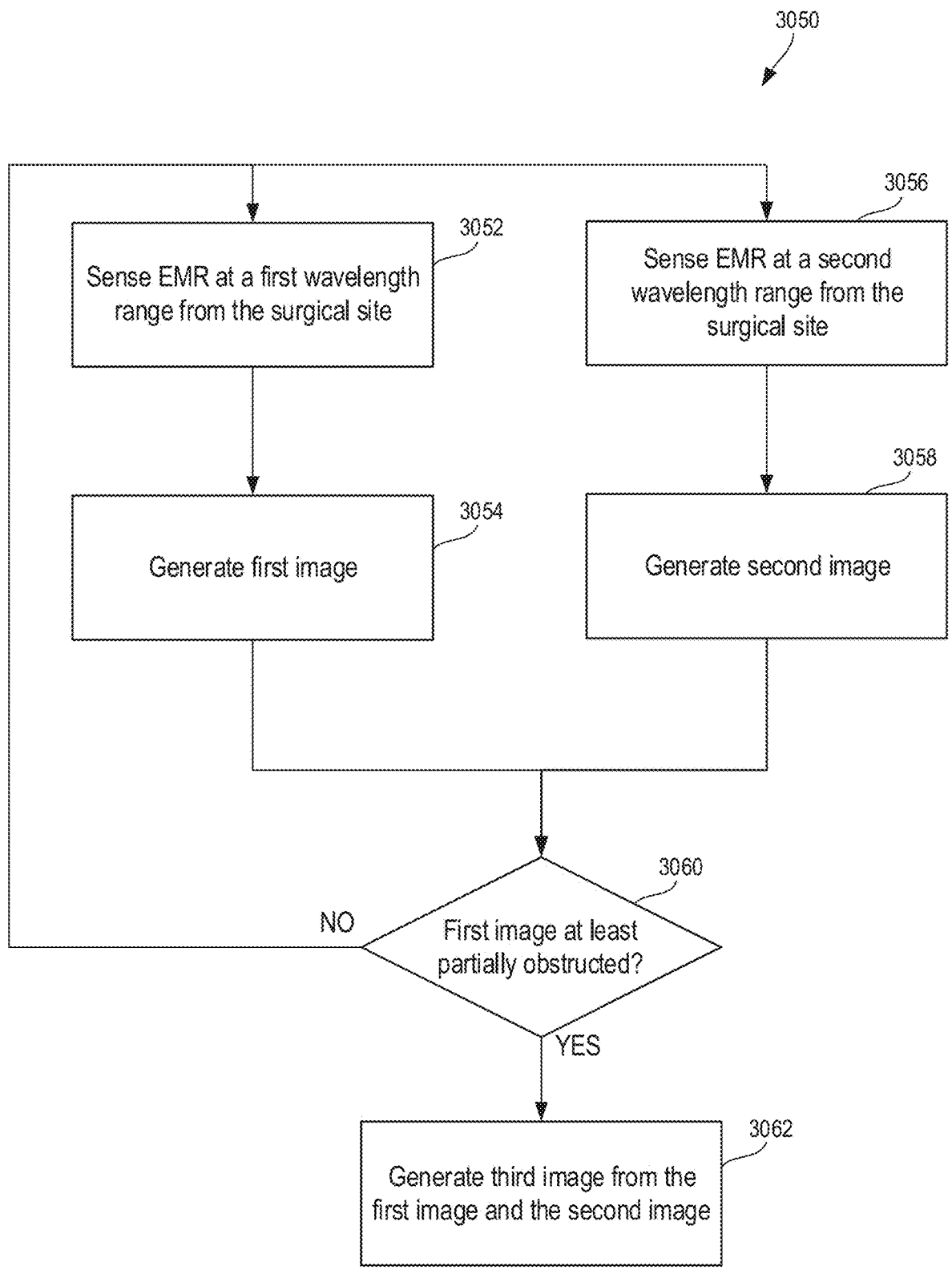

FIG. 24 is a logic flow diagram of a process for generating fused images utilizing a multispectral EMR source, in accordance with at least one aspect of the present disclosure.

Figure 25:
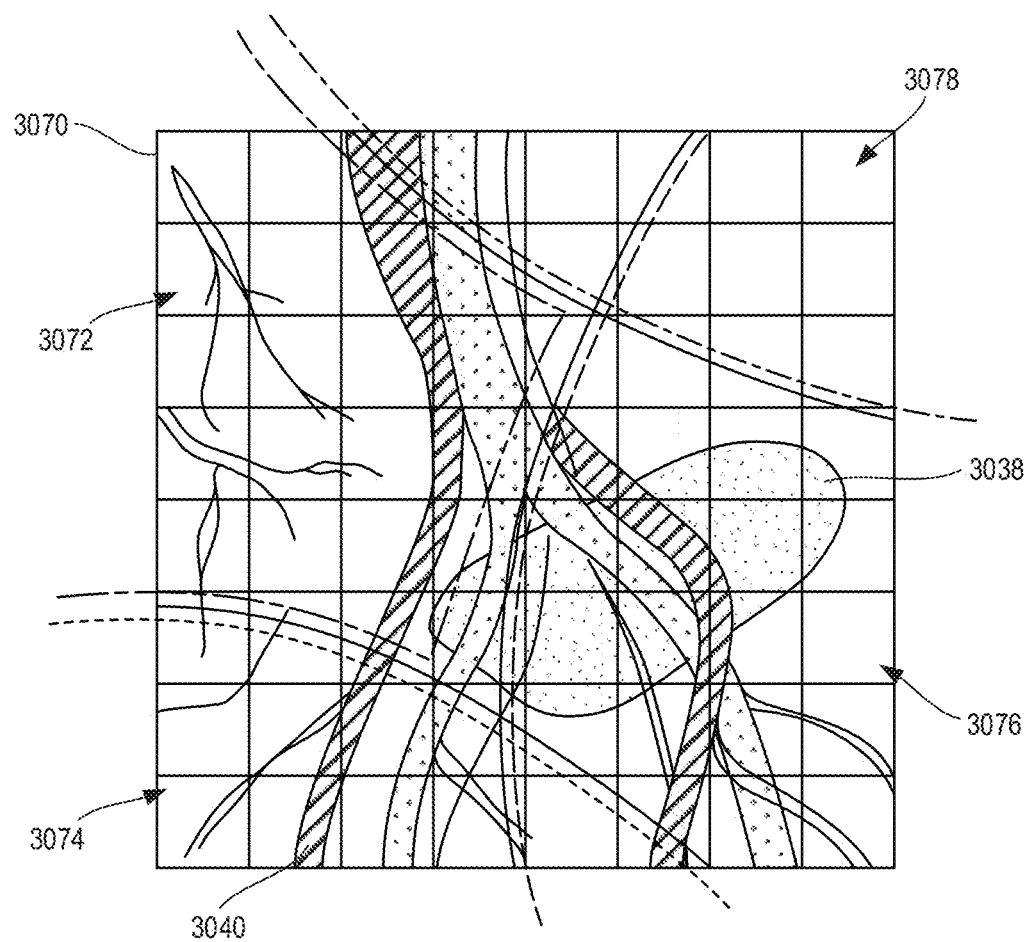

FIG. 25 is a diagram of a fused image generated from a multispectral EMR source, in accordance with at least one aspect of the present disclosure.

Figure 26:
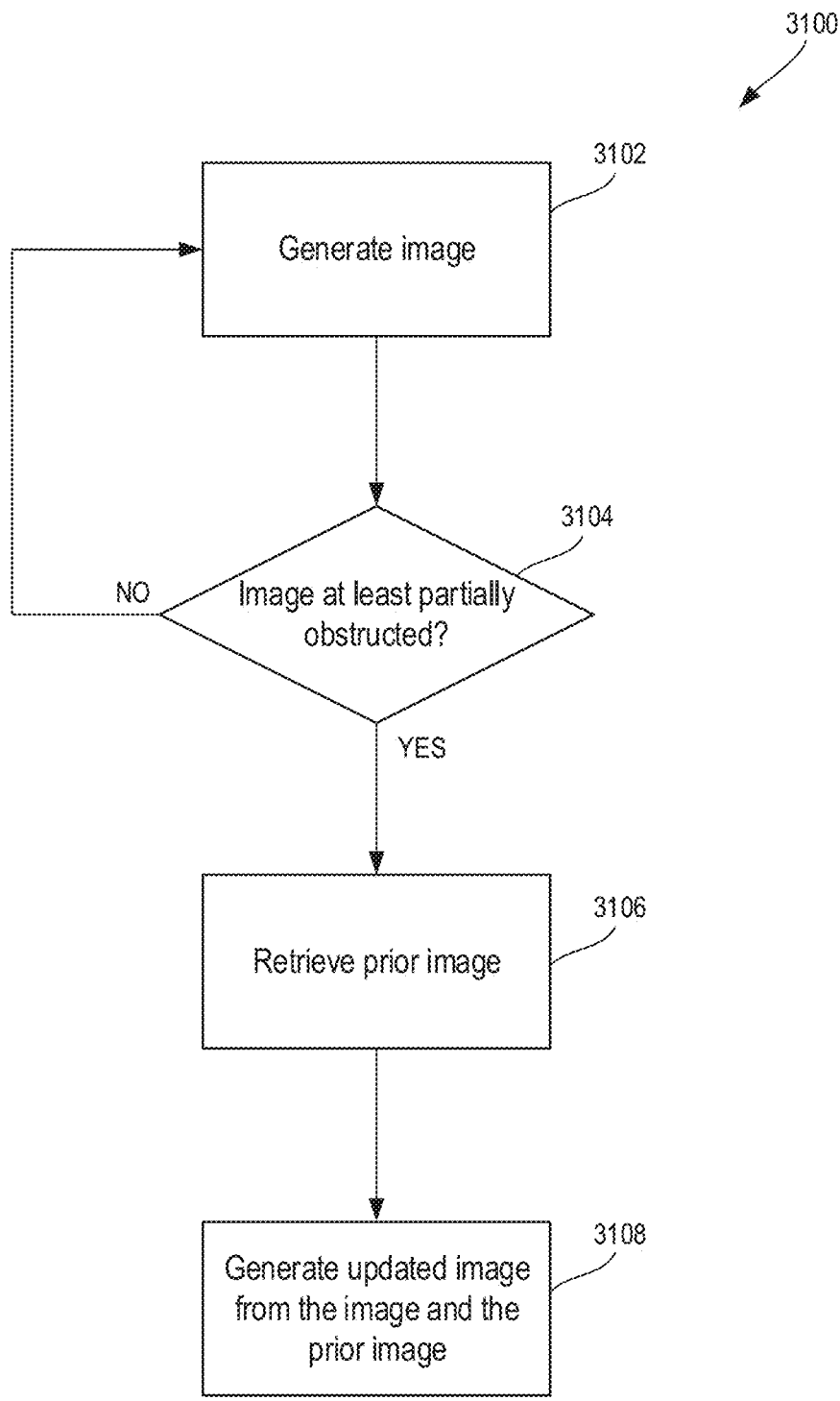

FIG. 26 is a logic flow diagram of a process for generating fused images utilizing multiple image frames, in accordance with at least one aspect of the present disclosure.

Figure 27:
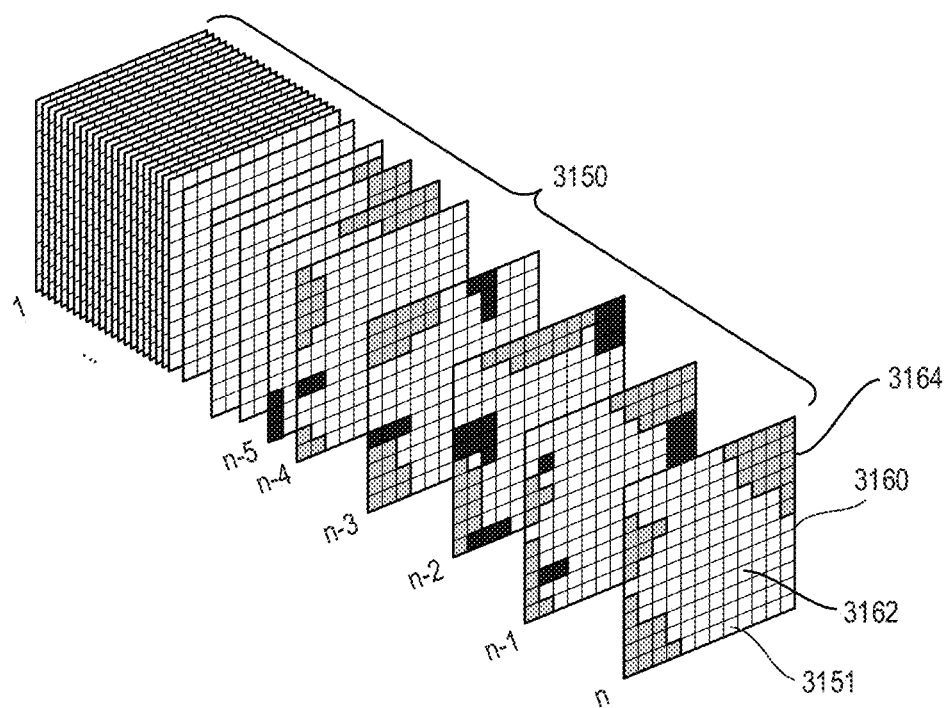

FIG. 27 is a diagram of a series of image frames, in accordance with at least one aspect of the present disclosure.

Figure 28:
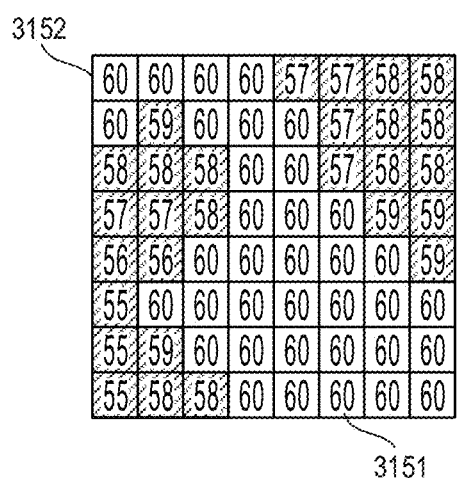

FIG. 28 is a diagram of a fused image, in accordance with at least one aspect of the present disclosure.

Figure 29:
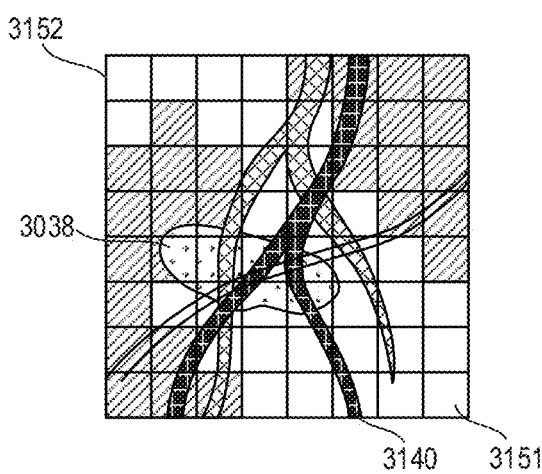

FIG. 29 is a diagram of a fused image as visualized to a user, in accordance with at least one aspect of the present disclosure.

Figure 30:
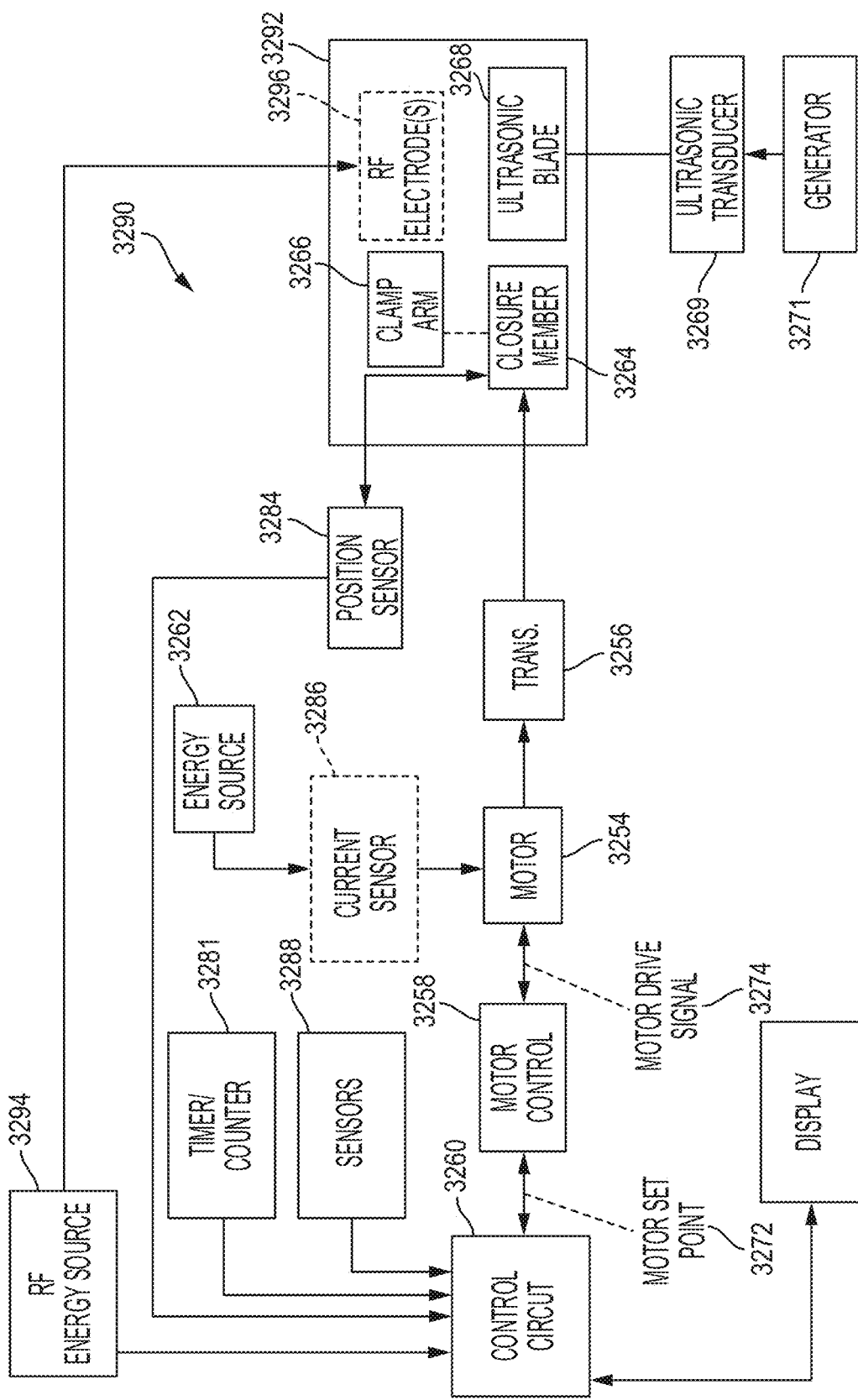

FIG. 30 is schematic diagram of a surgical instrument, in accordance with at least one aspect of the present disclosure.

Figure 31:
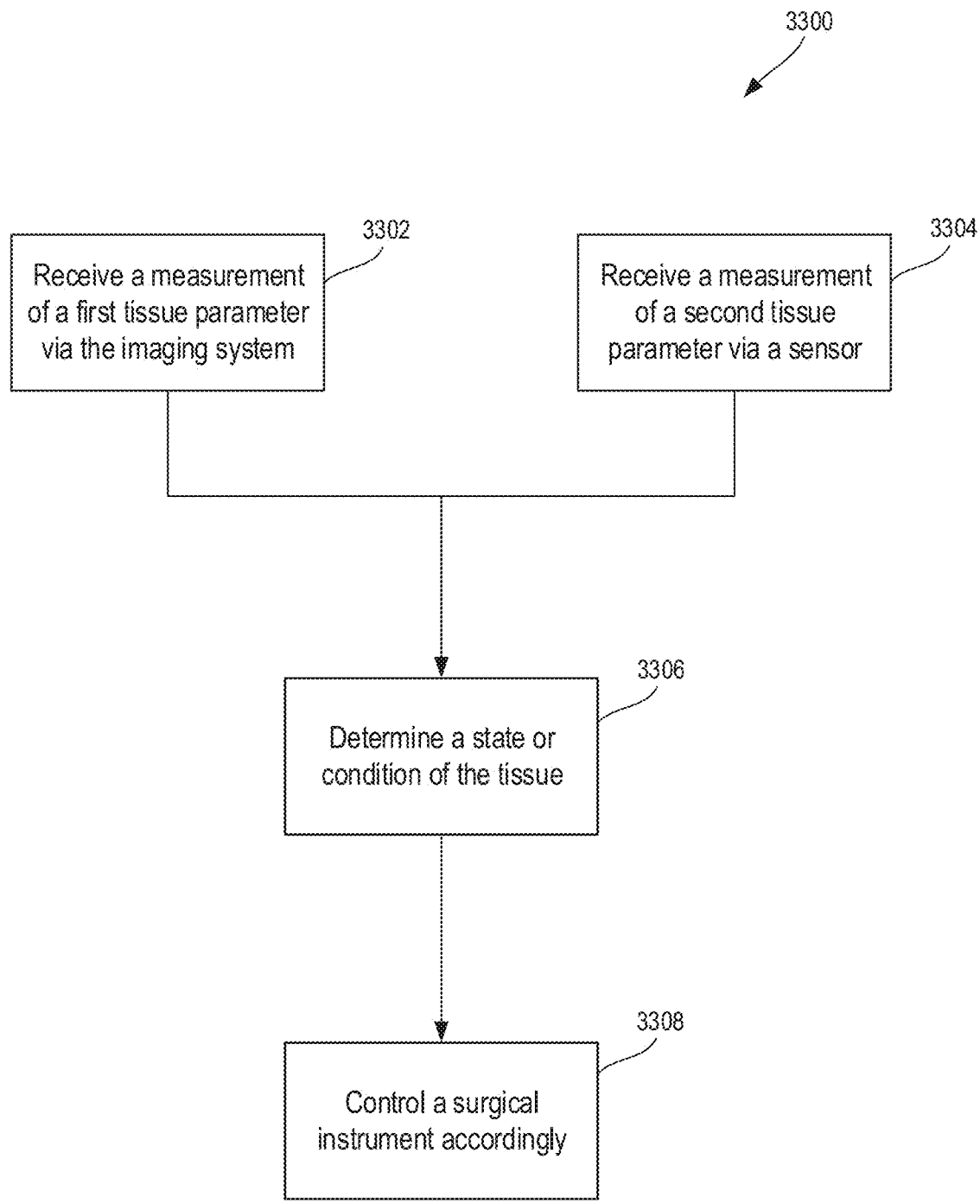

FIG. 31 is a logic flow diagram of a process for controlling a surgical system based on multiple sensed parameters, in accordance with at least one aspect of the present disclosure.

Figure 32:
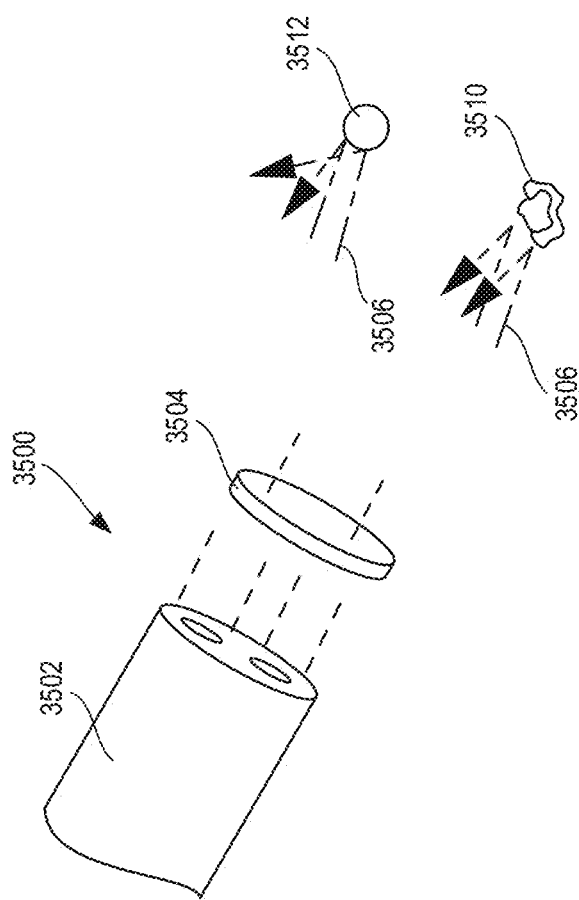

FIG. 32 is a diagram of a polarizing EMR source for detecting different particulate types, in accordance with at least one aspect of the present disclosure.

Figure 33A:
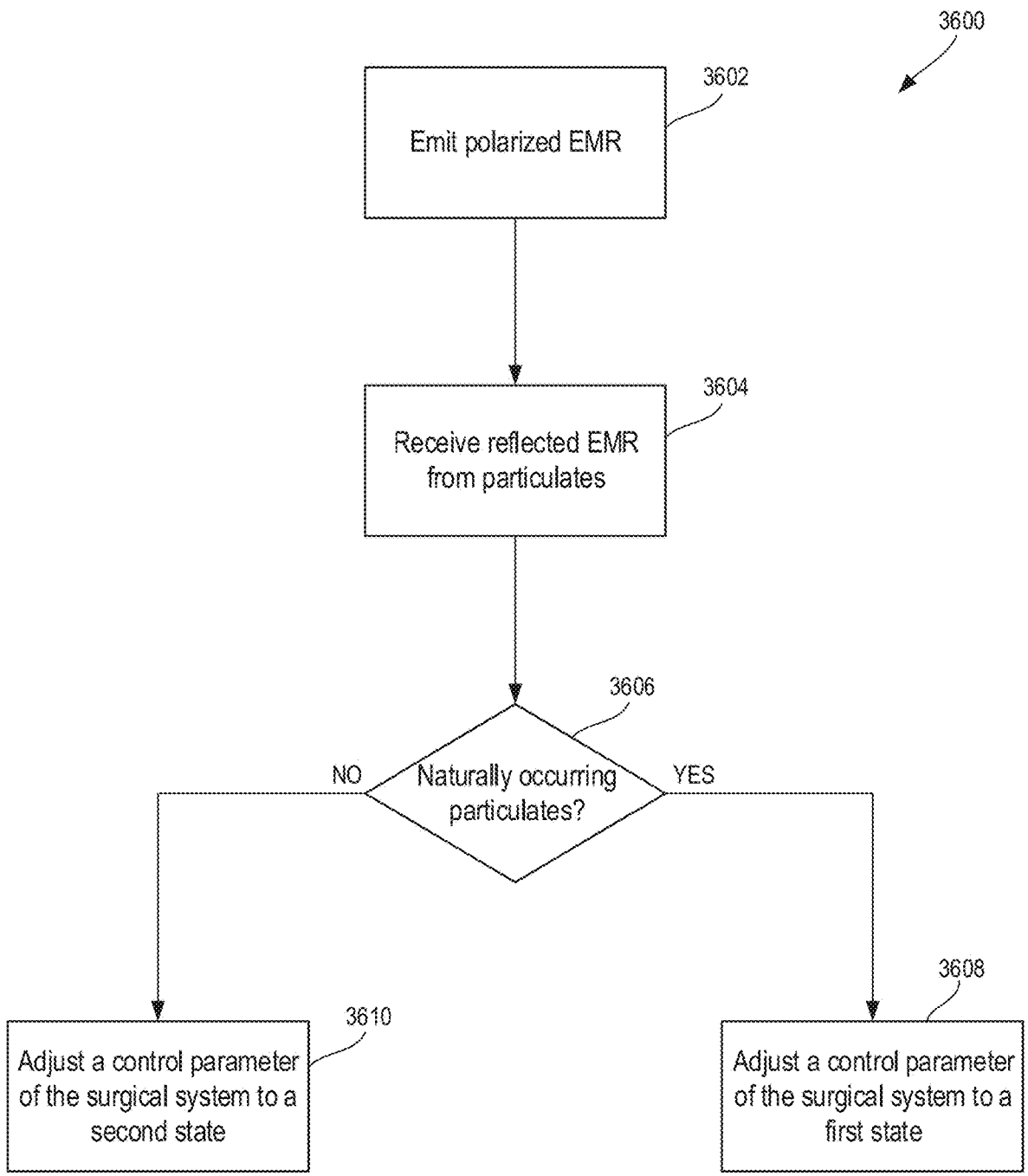

FIG. 33A is a logic flow diagram of a process for controlling a surgical system according to detected particulate types, in accordance with at least one aspect of the present disclosure.

Figure 33B:
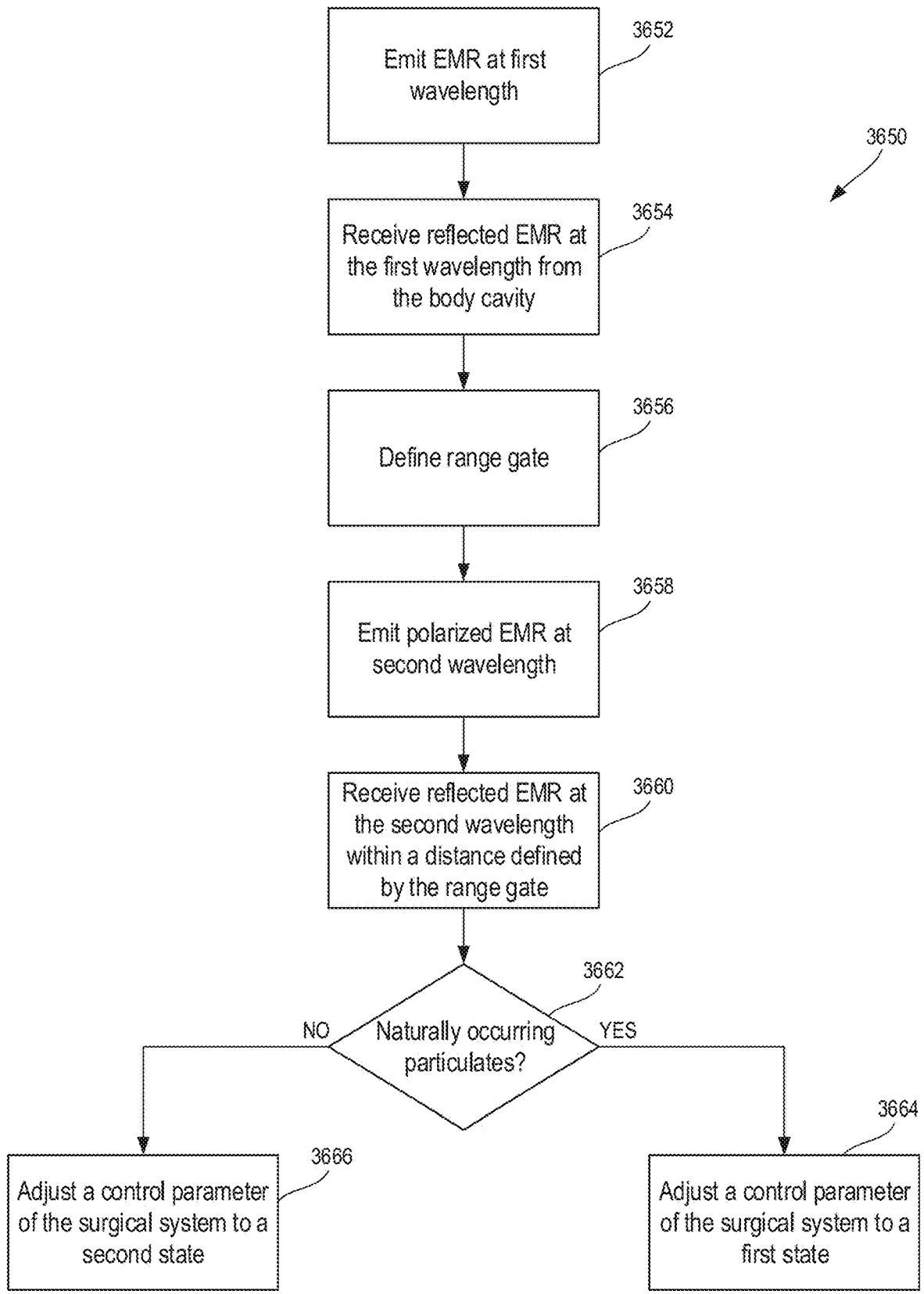

FIG. 33B is a logic flow diagram of a process for controlling a surgical system according to detected particulate types detected within a defined range gate, in accordance with at least one aspect of the present disclosure.

FIG. 34A is a pixel array of an image sensor detecting airborne particulates, in accordance with at least one aspect of the present disclosure.

FIG. 34B is a pixel array of an image sensor detecting airborne particulates that have moved from the positions shown in FIG. 34A, in accordance with at least one aspect of the present disclosure.

FIG. 34C is a pixel array of an image sensor indicating the generalized movement vector of the particulates shown in FIG. 34B, in accordance with at least one aspect of the present disclosure.

FIG. 35 illustrates a change in airborne particulate cloud state corresponding to FIGS. 34A-C, in accordance with at least one aspect of the present disclosure.

Figure 36:
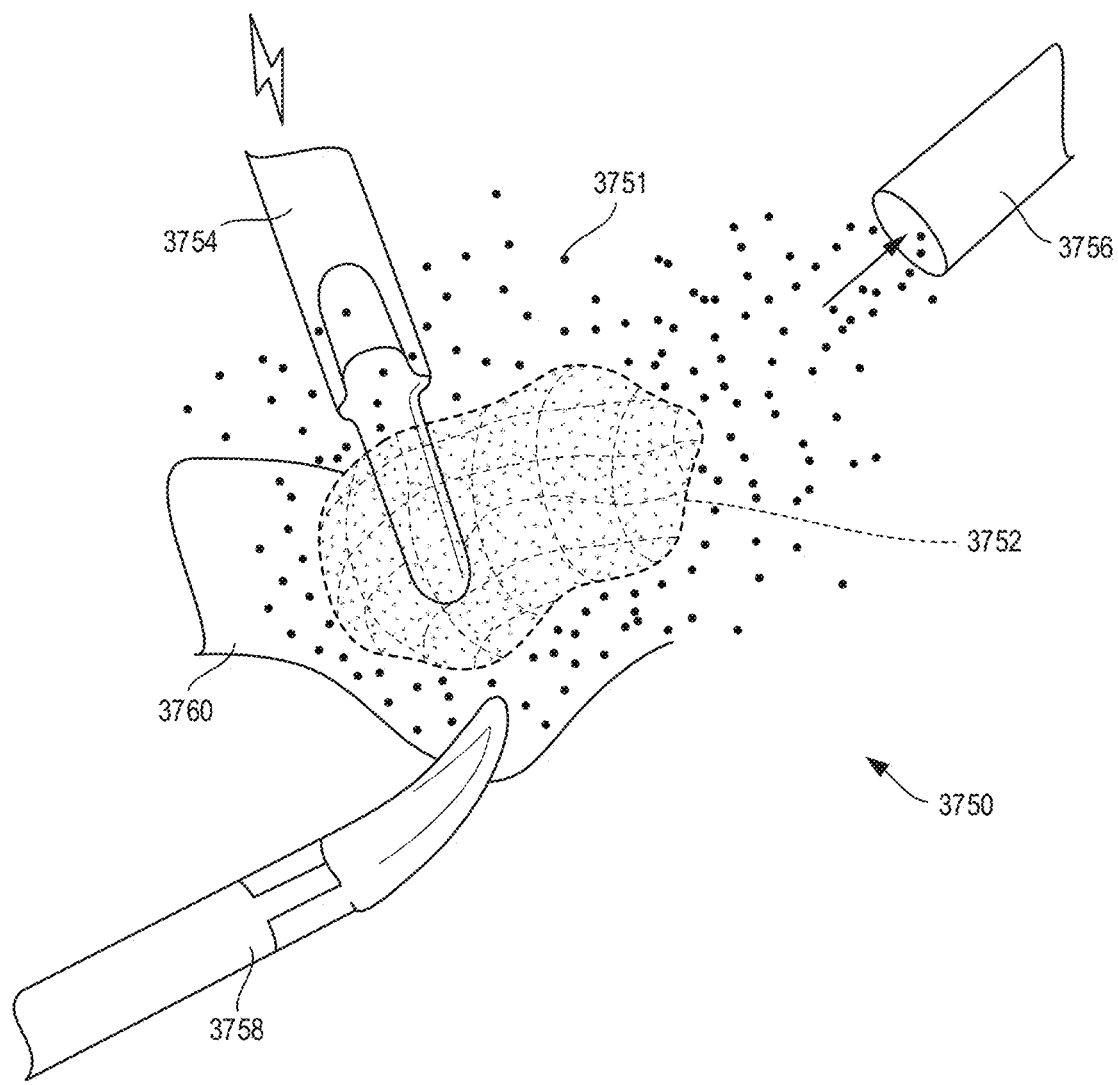

FIG. 36 is a diagram of a surgical system during the performance of a surgical procedure in which a particulate cloud is being generated, in accordance with at least one aspect of the present disclosure.

Figure 37:
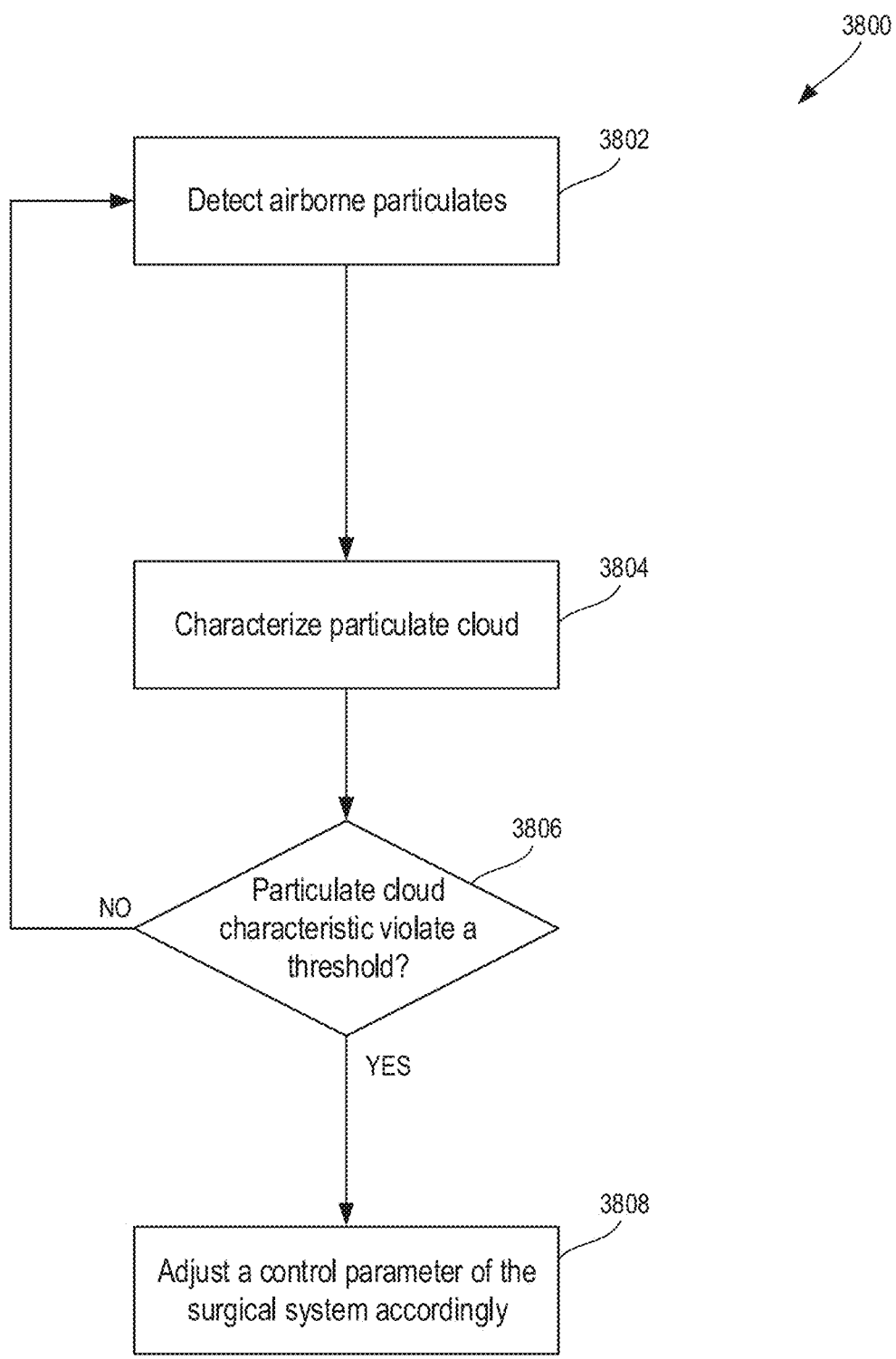

FIG. 37 is a logic flow diagram of a process for controlling a surgical system according to particulate cloud characteristics, in accordance with at least one aspect of the present disclosure.

Figure 38:
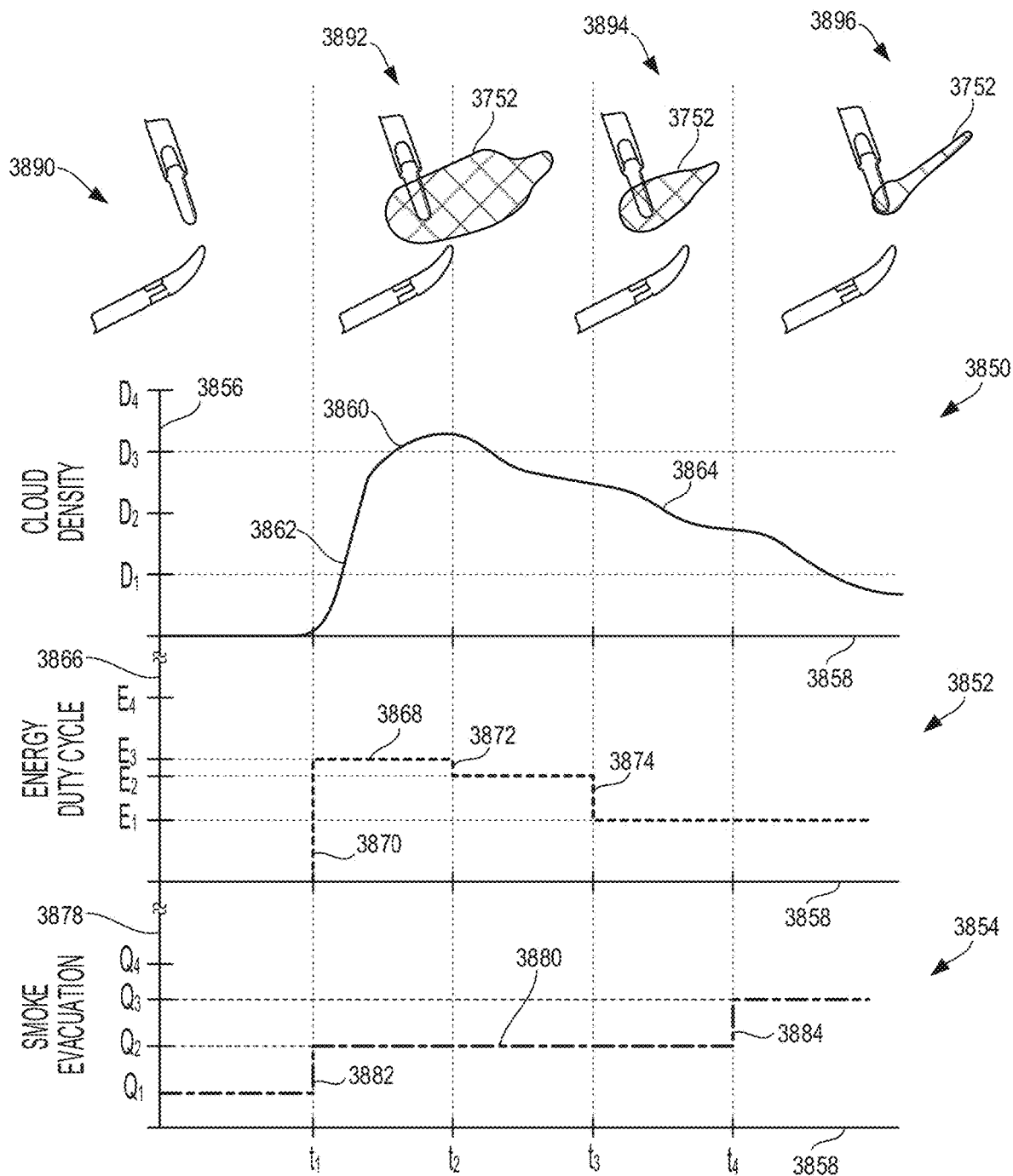

FIG. 38 is a series of graphs illustrating the adjustment of control parameters based on particulate cloud characteristics, in accordance with at least one aspect of the present disclosure.

DESCRIPTION

Applicant of the present application owns the following U.S. Patent Applications, filed Dec. 30, 2019, each of which is herein incorporated by reference in its entirety:
- U.S. patent application Ser. No. 16/729,807, titled METHOD OF USING IMAGING DEVICES IN SURGERY, now U.S. Pat. No. 11,284,963;
- U.S. patent application Ser. No. 16/729,803, titled ADAPTIVE VISUALIZATION BY A SURGICAL SYSTEM, now U.S. Pat. No. 11,744,667;
- U.S. patent application Ser. No. 16/729,790, titled SURGICAL SYSTEM CONTROL BASED ON MULTIPLE SENSED PARAMETERS, now U.S. Patent Application Publication No. 2021/0196098;
- U.S. patent application Ser. No. 16/729,737, titled ADAPTIVE SURGICAL SYSTEM CONTROL ACCORDING TO SURGICAL SMOKE CLOUD CHARACTERISTICS, now U.S. Patent Application Publication No. 2021/0196108;
- U.S. patent application Ser. No. 16/729,740, titled SURGICAL SYSTEMS CORRELATING VISUALIZATION DATA AND POWERED SURGICAL INSTRUMENT DATA, now U.S. Patent Application Publication No. 2021/0196383;
- U.S. patent application Ser. No. 16/729,751, titled SURGICAL SYSTEMS FOR GENERATING THREE DIMENSIONAL CONSTRUCTS OF ANATOMICAL ORGANS AND COUPLING IDENTIFIED, now U.S. Pat. No. 11,759,283;
- U.S. patent application Ser. No. 16/729,735, titled SURGICAL SYSTEM FOR OVERLAYING SURGICAL INSTRUMENT DATA ONTO A VIRTUAL THREE DIMENSIONAL CONSTRUCT OF AN ORGAN, now U.S. Pat. No. 11,648,060;
- U.S. patent application Ser. No. 16/729,729, titled SURGICAL SYSTEMS FOR PROPOSING AND CORROBORATING ORGAN PORTION REMOVALS, now U.S. Patent Application Publication No. 2021/0196381;
- U.S. patent application Ser. No. 16/729,778, titled SYSTEM AND METHOD FOR DETERMINING, ADJUSTING, AND MANAGING RESECTION MARGIN ABOUT A SUBJECT TISSUE, now U.S. Pat. No. 11,776,144;
- U.S. patent application Ser. No. 16/729,744, titled VISUALIZATION SYSTEMS USING STRUCTURED LIGHT, now U.S. Pat. No. 11,219,501;
- U.S. Patent application Ser. No. 16/729,747, titled DYNAMIC SURGICAL VISUALIZATION SYSTEMS, now U.S. Patent Application Publication No. 2021/0196384; and
- U.S. Patent application Ser. No. 16/729,772, titled ANALYZING SURGICAL TRENDS BY A SURGICAL SYSTEM, now U.S. Pat. No. 11,832,996.

Applicant of the present application owns the following U.S. Patent Applications, filed on Mar. 15, 2019, each of which is herein incorporated by reference in its entirety:
- U.S. patent application Ser. No. 16/354,417, titled INPUT CONTROLS FOR ROBOTIC SURGERY;
- U.S. patent application Ser. No. 16/354,420, titled DUAL MODE CONTROLS FOR ROBOTIC SURGERY;
- U.S. patent application Ser. No. 16/354,422, titled MOTION CAPTURE CONTROLS FOR ROBOTIC SURGERY;
- U.S. patent application Ser. No. 16/354,440, titled ROBOTIC SURGICAL SYSTEMS WITH MECHANISMS FOR SCALING SURGICAL TOOL MOTION ACCORDING TO TISSUE PROXIMITY;
- U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE;
- U.S. patent application Ser. No. 16/354,454, titled ROBOTIC SURGICAL SYSTEMS WITH SELECTIVELY LOCKABLE END EFFECTORS;
- U.S. patent application Ser. No. 16/354,461, titled SELECTABLE VARIABLE RESPONSE OF SHAFT MOTION OF SURGICAL ROBOTIC SYSTEMS;
- U.S. patent application Ser. No. 16/354,470, titled SEGMENTED CONTROL INPUTS FOR SURGICAL ROBOTIC SYSTEMS;
- U.S. patent application Ser. No. 16/354,474, titled ROBOTIC SURGICAL CONTROLS HAVING FEEDBACK CAPABILITIES;
- U.S. patent application Ser. No. 16/354,478, titled ROBOTIC SURGICAL CONTROLS WITH FORCE FEEDBACK; and
- U.S. patent application Ser. No. 16/354,481, titled JAW COORDINATION OF ROBOTIC SURGICAL CONTROLS.

Applicant of the present application also owns the following U.S. Patent Applications, filed on Sep. 11, 2018, each of which is herein incorporated by reference in its entirety:
- U.S. patent application Ser. No. 16/128,179, titled SURGICAL VISUALIZATION PLATFORM;
- U.S. patent application Ser. No. 16/128,180, titled CONTROLLING AN EMITTER ASSEMBLY PULSE SEQUENCE;
- U.S. patent application Ser. No. 16/128,198, titled SINGULAR EMR SOURCE EMITTER ASSEMBLY;
- U.S. patent application Ser. No. 16/128,207, titled COMBINATION EMITTER AND CAMERA ASSEMBLY;
- U.S. patent application Ser. No. 16/128,176, titled SURGICAL VISUALIZATION WITH PROXIMITY TRACKING FEATURES;
- U.S. patent application Ser. No. 16/128,187, titled SURGICAL VISUALIZATION OF MULTIPLE TARGETS;
- U.S. patent application Ser. No. 16/128,192, titled VISUALIZATION OF SURGICAL DEVICES;
- U.S. patent application Ser. No. 16/128,163, titled OPERATIVE COMMUNICATION OF LIGHT;
- U.S. patent application Ser. No. 16/128,197, titled ROBOTIC LIGHT PROJECTION TOOLS;
- U.S. patent application Ser. No. 16/128,164, titled SURGICAL VISUALIZATION FEEDBACK SYSTEM;
- U.S. patent application Ser. No. 16/128,193, titled SURGICAL VISUALIZATION AND MONITORING;
- U.S. patent application Ser. No. 16/128,195, titled INTEGRATION OF IMAGING DATA;
- U.S. patent application Ser. No. 16/128,170, titled ROBOTICALLY-ASSISTED SURGICAL SUTURING SYSTEMS;
- U.S. patent application Ser. No. 16/128,183, titled SAFETY LOGIC FOR SURGICAL SUTURING SYSTEMS;
- U.S. patent application Ser. No. 16/128,172, titled ROBOTIC SYSTEM WITH SEPARATE PHOTOACOUSTIC RECEIVER; and
- U.S. patent application Ser. No. 16/128,185, titled FORCE SENSOR THROUGH STRUCTURED LIGHT DEFLECTION.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, now U.S. Patent Application Publication No. 2019/0201111;

U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,711, titled SENSING ARRANGEMENTS FOR ROBOT-ASSISTED SURGICAL PLATFORMS, now U.S. Patent Application Publication No. 2019/0201120; and U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905.

Applicant of the present application owns the following U.S. Patent Applications, filed on Dec. 4, 2018, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Surgical Visualization System

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. It should be noted that throughout the following disclosure, any reference to "light," unless specifically in reference to visible light, can include electromagnetic radiation (EMR) or photons in the visible and/or non-visible portions of the EMR wavelength spectrum. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
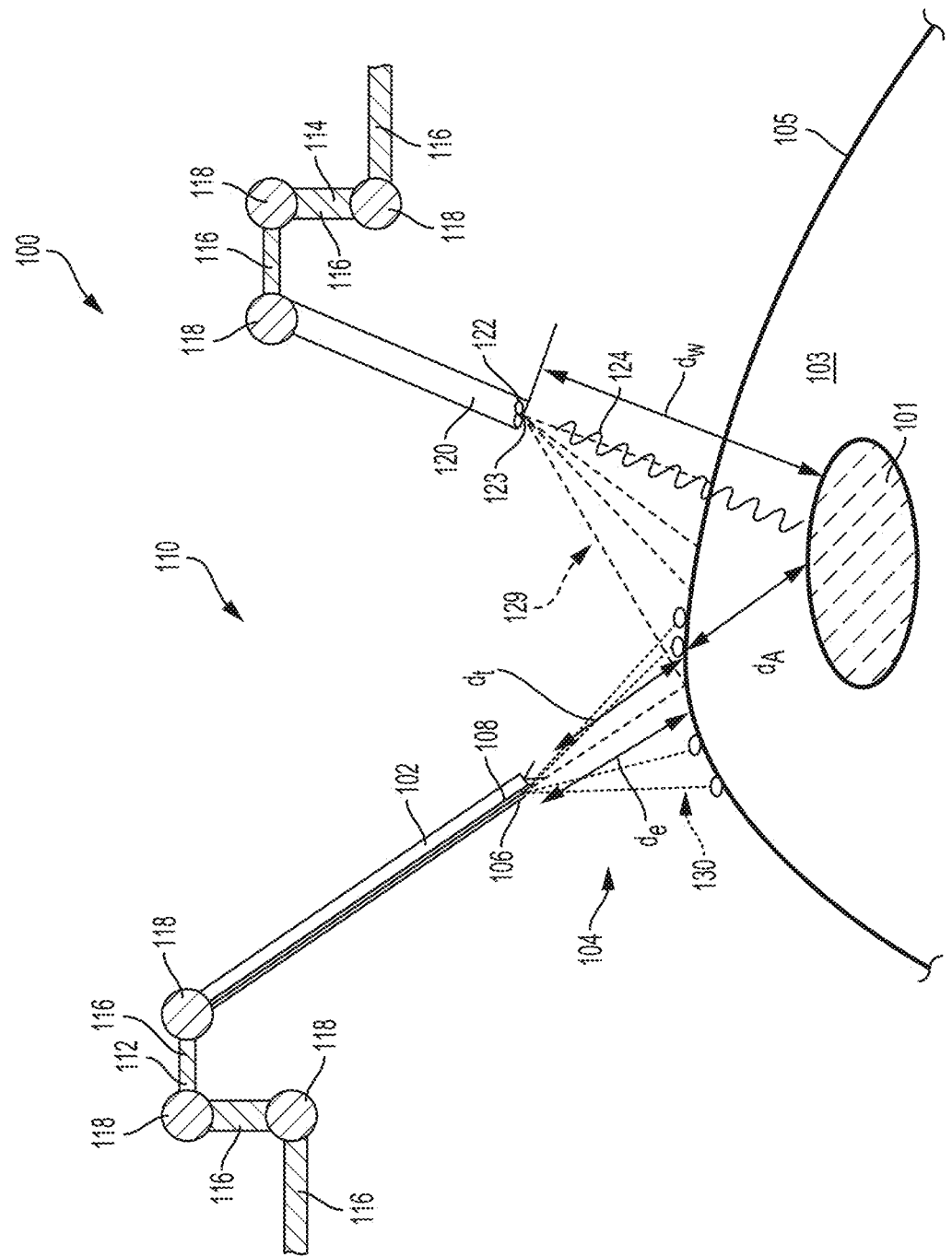
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
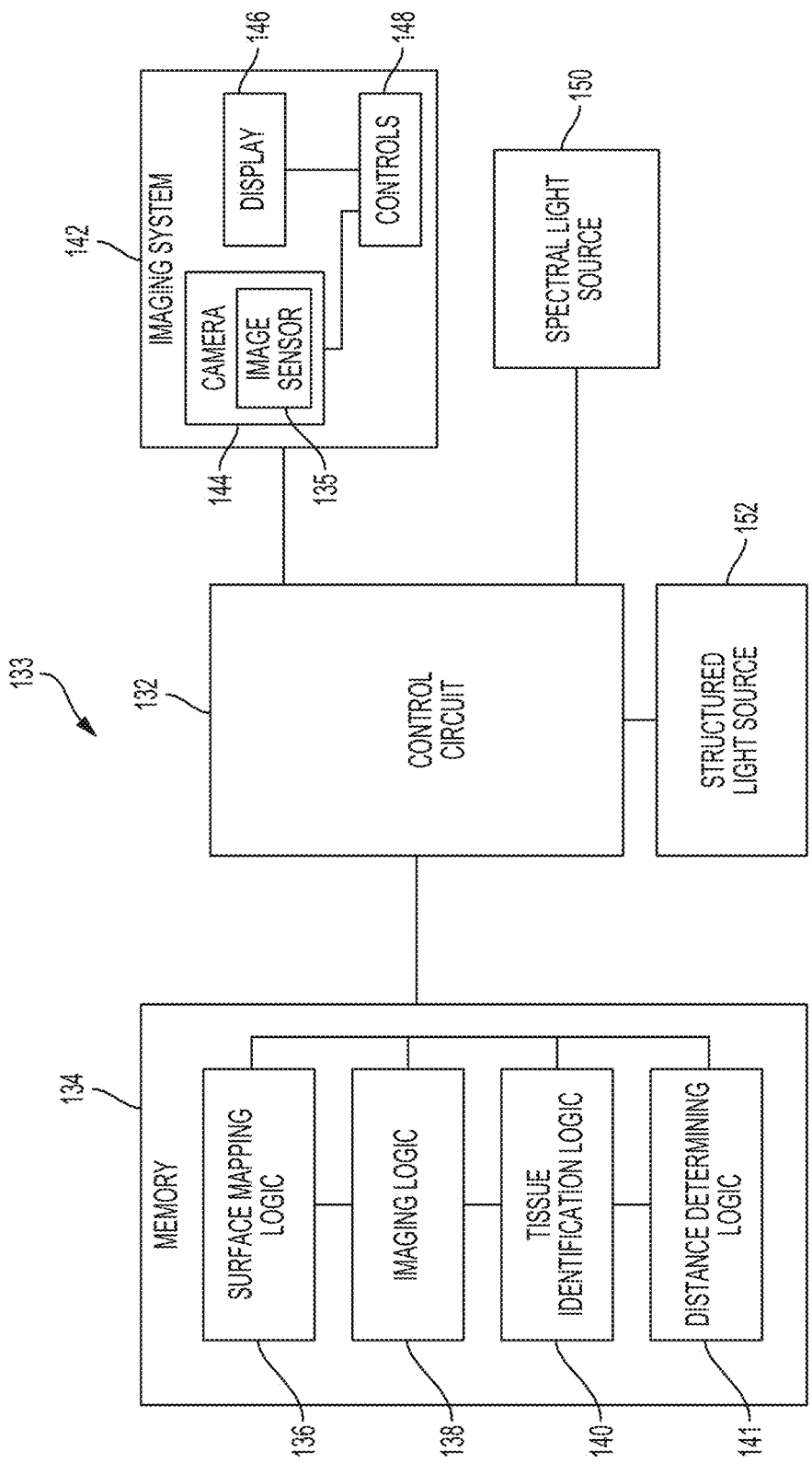
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, shortwave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
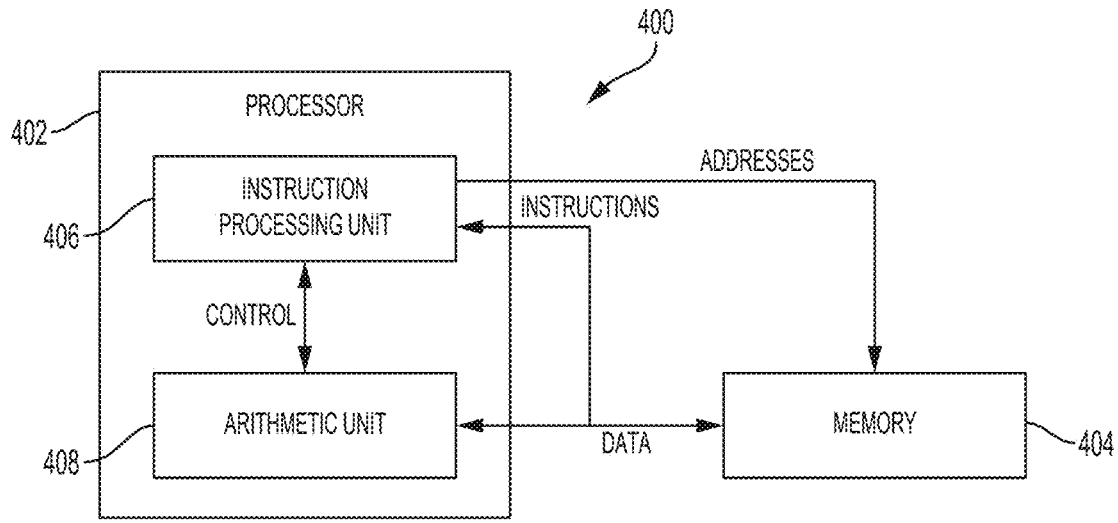
FIG. 2A illustrates a control circuit configured to control aspects of a surgical visualization system, according to at least one aspect of the present disclosure.
Figure 2B:
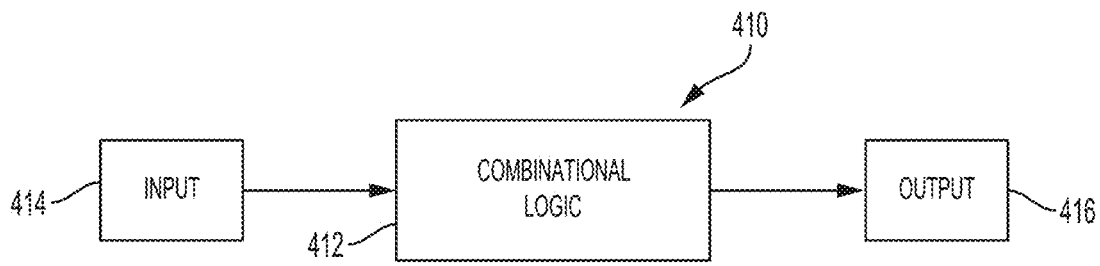
FIG. 2B illustrates a combinational logic circuit configured to control aspects of a surgical visualization system, according to at least one aspect of the present disclosure.
Figure 2C:
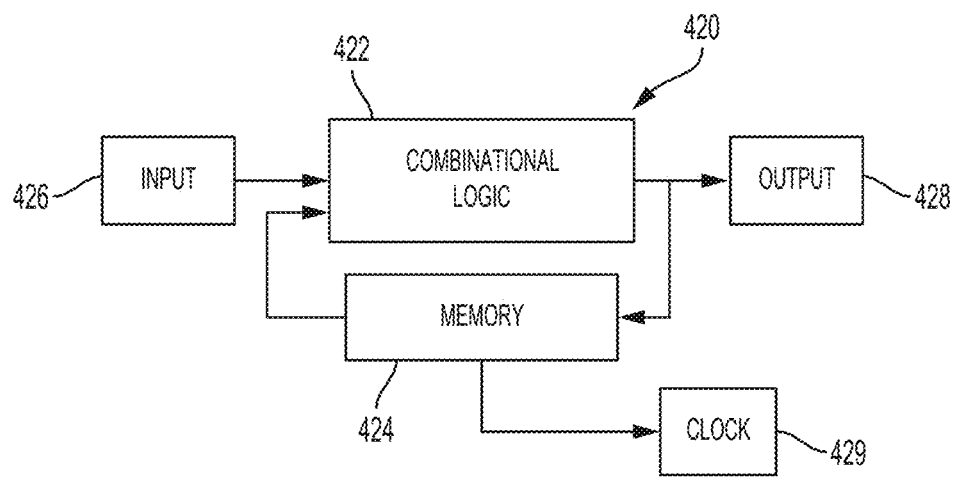
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned U.S. Patent Applications, including U.S. patent application Ser. No. 16/128,192, titled VISUALIZATION OF SURGICAL DEVICES, filed Sep. 11, 2018, for example, which are incorporated by reference herein in their respective entireties.

In one aspect, the critical structure 101 may be embedded in tissue 103. Stated differently, the critical structure 101 may be positioned below the surface 105 of the tissue 103.

In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
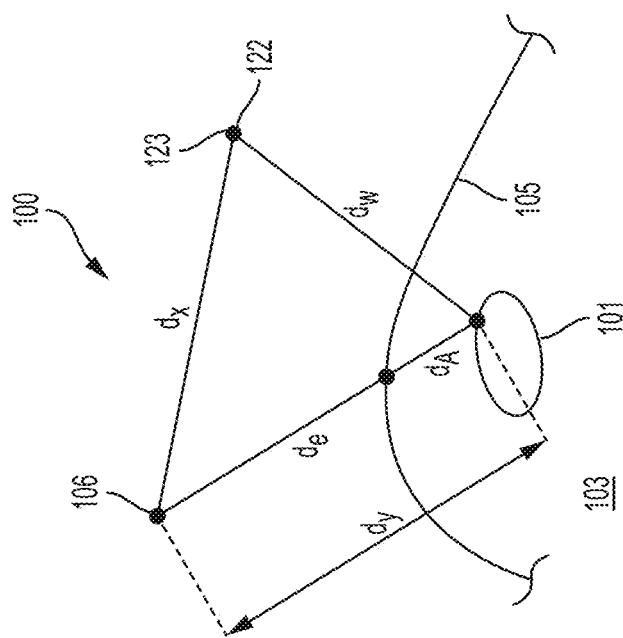
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
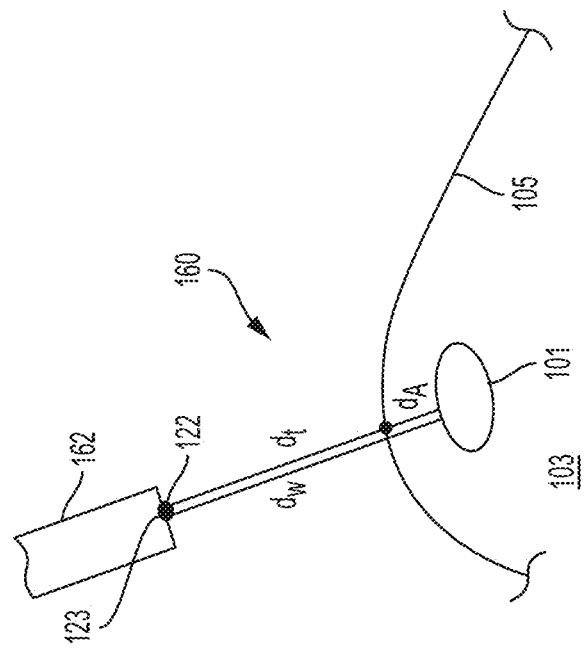
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
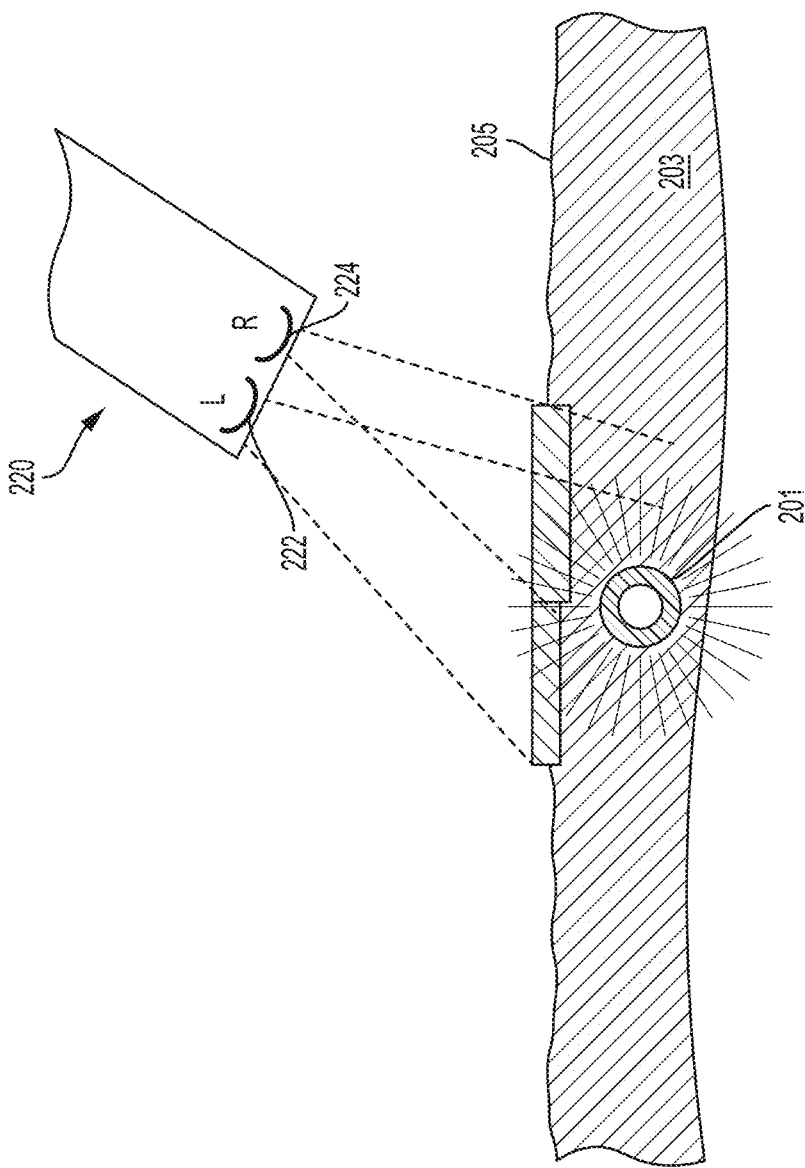
FIG. 6 is a schematic of a surgical visualization system including a three-dimensional camera, wherein the surgical visualization system is configured to identify a critical structure that is embedded within tissue, according to at least one aspect of the present disclosure.
Figures 7A, 7B:
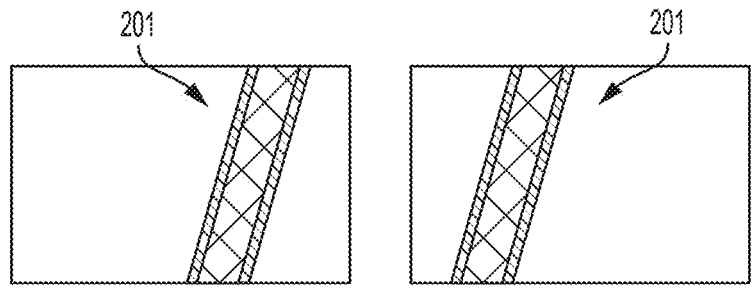
Figure 8:
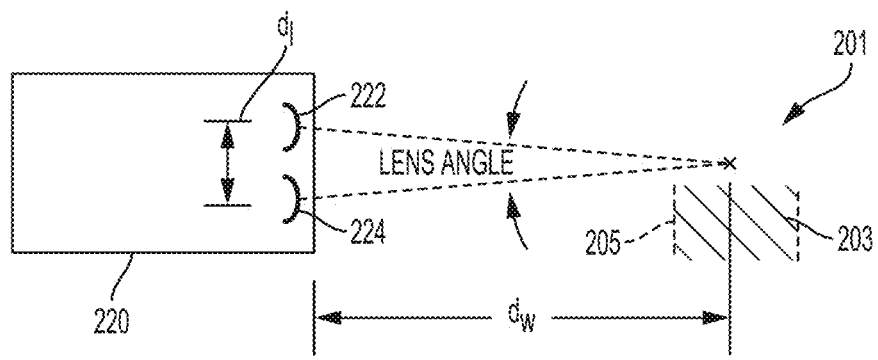
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
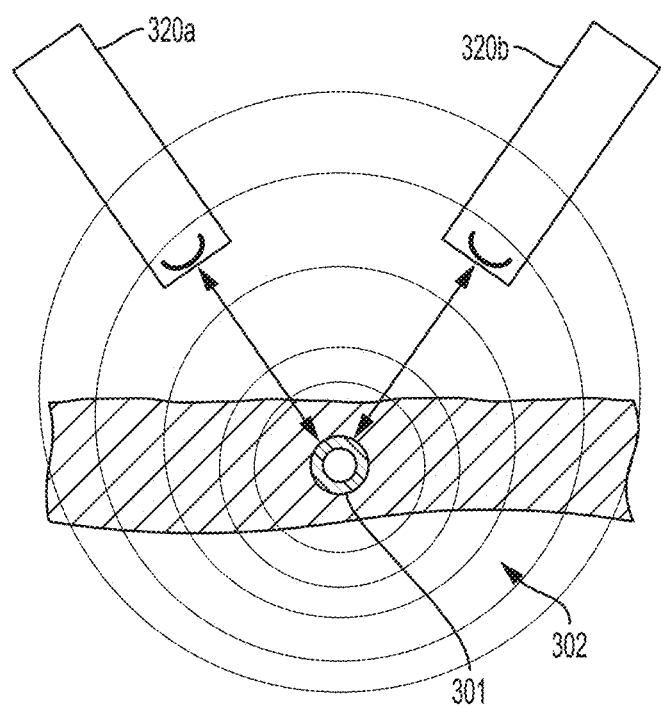
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/ image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
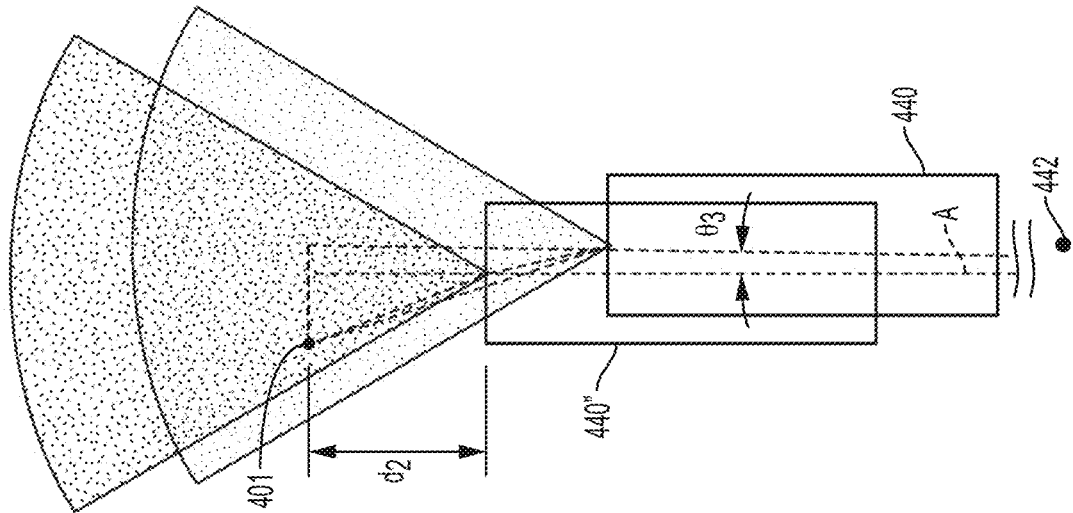
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
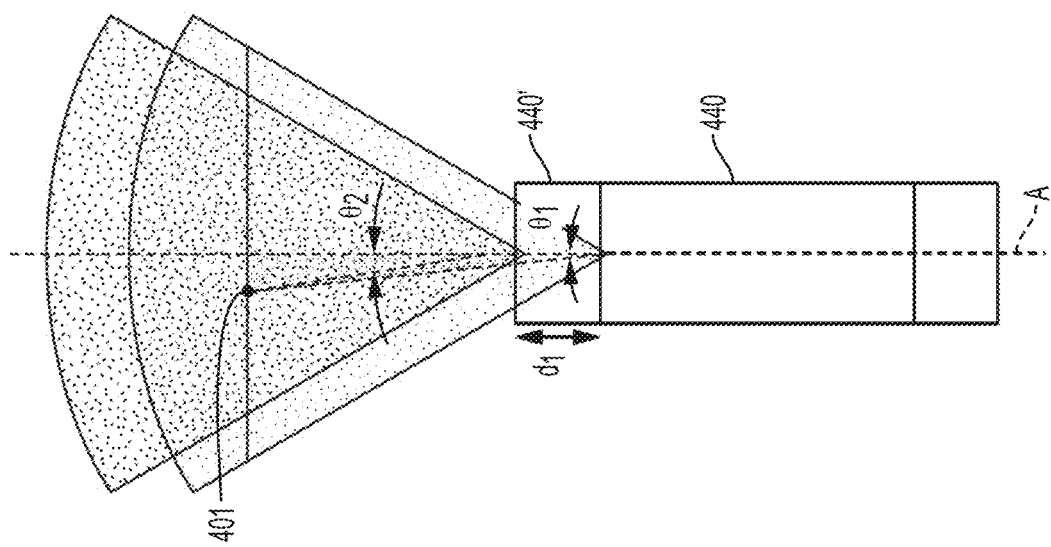
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta 3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta 3$ can be 0.9 degrees, for example.

Figure 5:
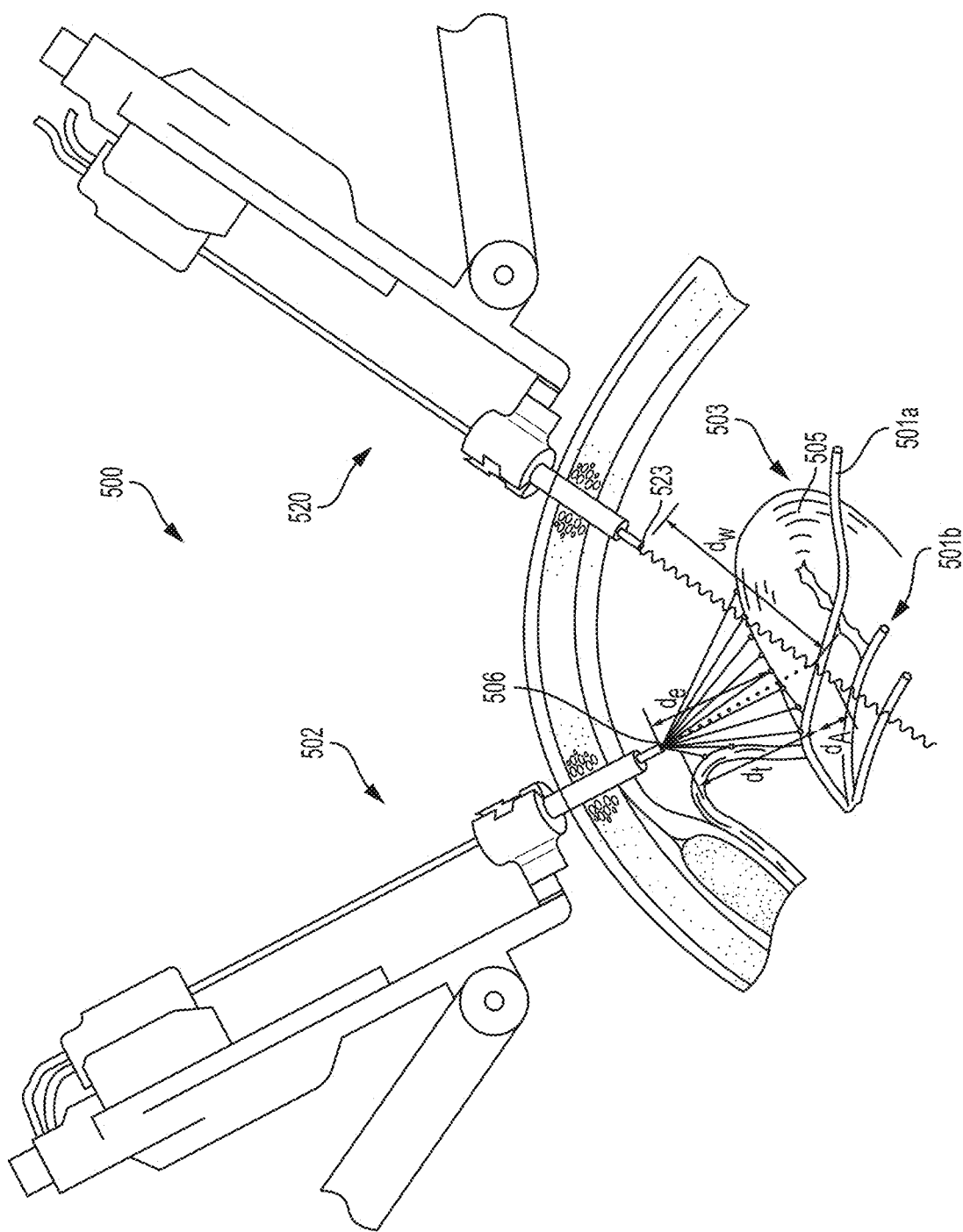
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera—to ureter distance $d_t$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
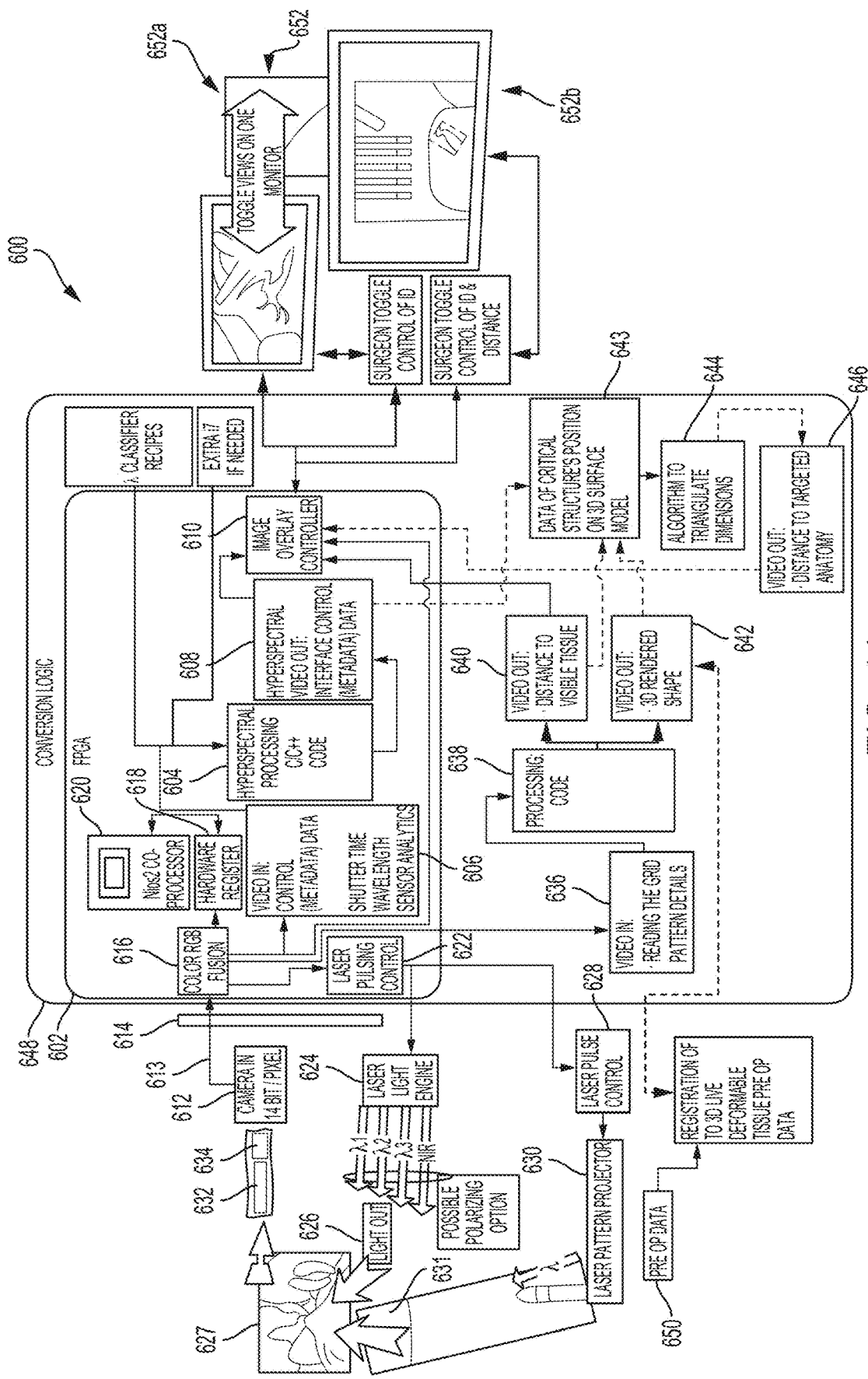
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned U.S. Patent Applications, including U.S. patent application Ser. No. 16/128,195, titled INTEGRATION OF IMAGING DATA, filed Sep. 11, 2018, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
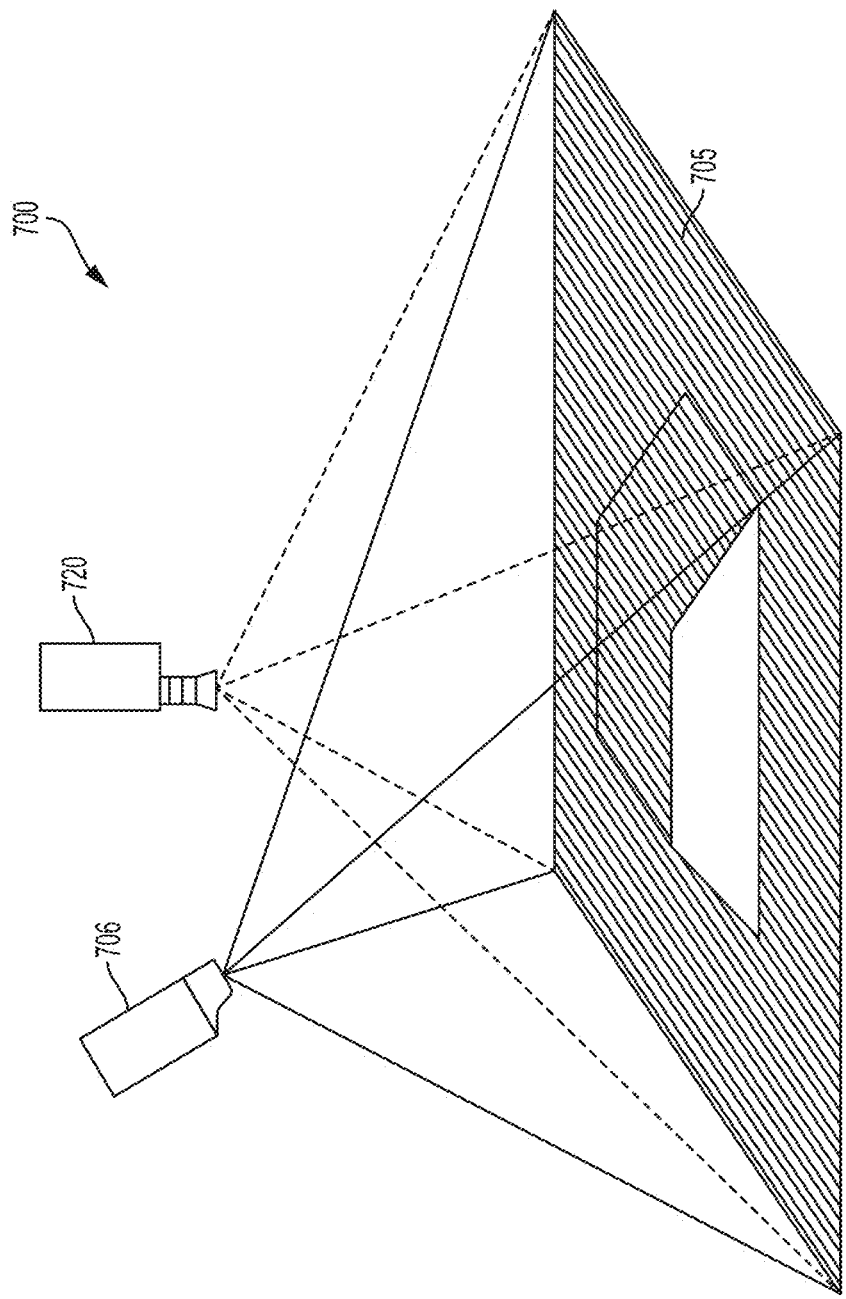
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13A:
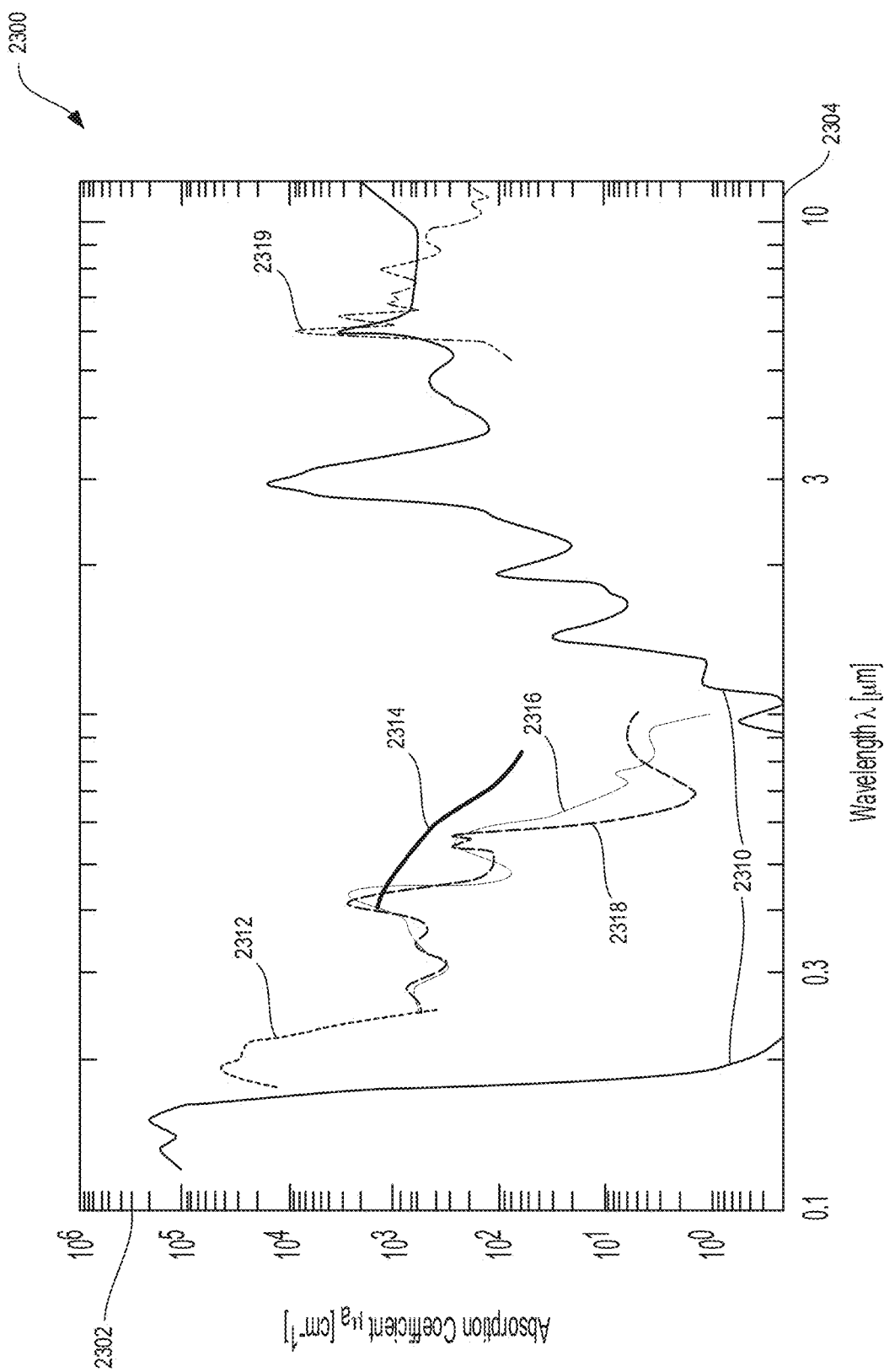
FIG. 13A is a graph of absorption coefficient verse wavelength for various biological materials, according to at least one aspect of the present disclosure.

As noted above, the various surgical visualization systems described herein can be utilized to visualize various different types of tissues and/or anatomical structures, including tissues and/or anatomical structures that may be obscured from being visualized by EMR in the visible portion of the spectrum. In one aspect, the surgical visualization systems can utilize a spectral imaging system to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be further configured to characterize the tissue type of the tissue being visualized based upon the particular combination of constituent materials. To illustrate, FIG. 13A is a graph 2300 depicting how the absorption coefficient of various biological materials varies across the EMR wavelength spectrum.

In the graph 2300, the vertical axis 2303 represents absorption coefficient of the biological material (e.g., in $cm^{-1}$) and the horizontal axis 2304 represents EMR wavelength (e.g., in μm). The graph 2300 further illustrates a first line 2310 representing the absorption coefficient of water at various EMR wavelengths, a second line 2312 representing the absorption coefficient of protein at various EMR wavelengths, a third line 2314 representing the absorption coefficient of melanin at various EMR wavelengths, a fourth line 2316 representing the absorption coefficient of deoxygenated hemoglobin at various EMR wavelengths, a fifth line 2318 representing the absorption coefficient of oxygenated hemoglobin at various EMR wavelengths, and a sixth line 2319 representing the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 13B:
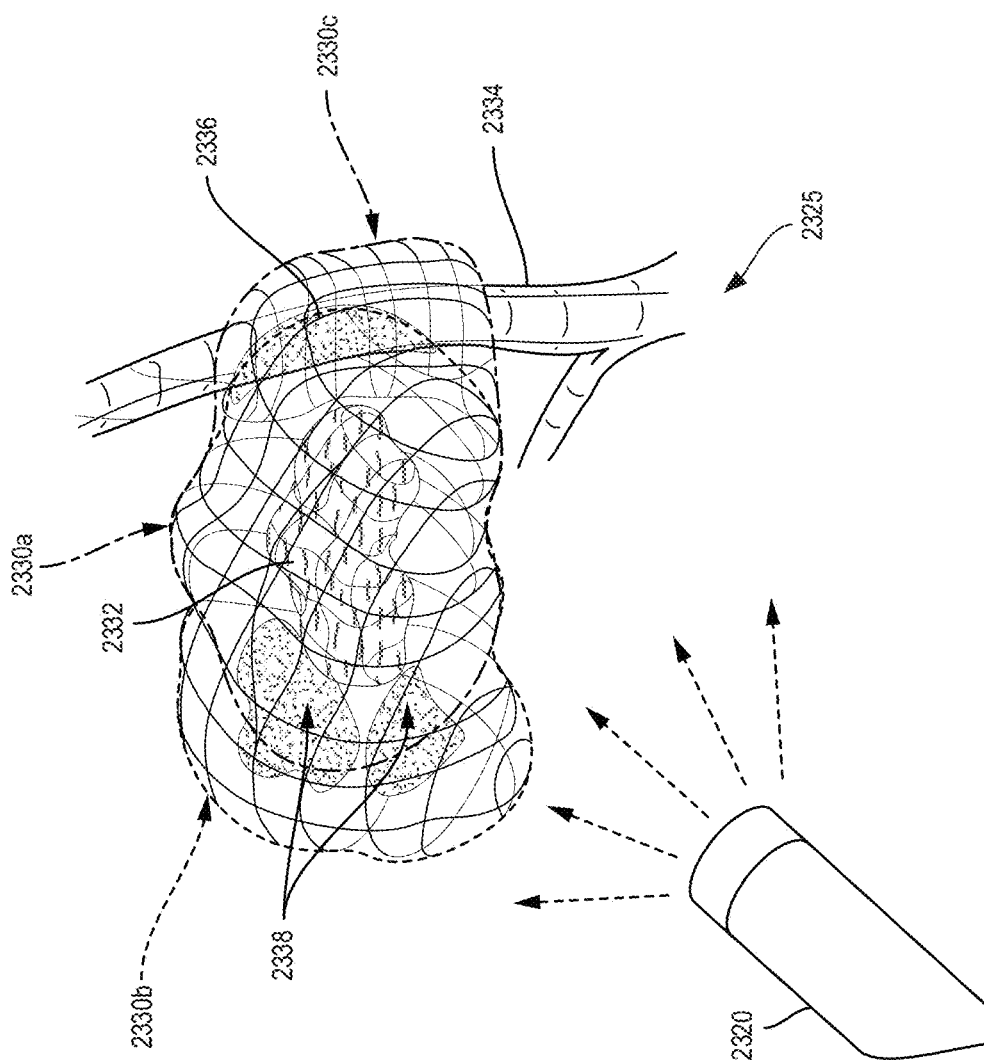
FIG. 13B is a schematic of the visualization of anatomical structures via a spectral surgical visualization system, according to at least one aspect of the present disclosure.

An illustration of the utilization of spectral imaging techniques to visualize different tissue types and/or anatomical structures is shown in FIG. 13B. In FIG. 13B, a spectral emitter 2320 (e.g., spectral light source 150) is being utilized by an imaging system to visualize a surgical site 2325. The EMR emitted by the spectral emitter 2320 and reflected from the tissues and/or structures at the surgical site 2325 can be received by an image sensor 135 (FIG. 2) to visualize the tissues and/or structures, which can be either visible (e.g., be located at the surface of the surgical site 2325) or obscured (e.g., underlay other tissue and/or structures at the surgical site 2325). In this example, an imaging system 142 (FIG. 2) can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system 142, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Further, the imaging system 142 can be configured to tailor or update the displayed surgical site visualization according to the identified tissue and/or structure types. For example, the imaging system 142 can display a margin 2330a associated with the tumor 2332 being visualized on a display screen (e.g., display 146). The margin 2330a can indicate the area or amount of tissue that should be excised to ensure complete removal of the tumor 2332. The control system 133 (FIG. 2) can be configured to control or update the dimensions of the margin 2330a based on the tissues and/or structures identified by the imaging system 142. In the illustrated example, the imaging system 142 has identified multiple abnormalities 2338 within the FOV. Accordingly, the control system 133 can adjust the displayed margin 2330a to a first updated margin 2330b having sufficient dimensions to encompass the abnormalities 2338. Further, the imaging system 142 has also identified an artery 2334 partially overlapping with the initially displayed margin 2330a (as indicated by the highlighted region 2336 of the artery 2334). Accordingly, the control system 133 can adjust the displayed margin 2330a to a second updated margin 2330c having sufficient dimensions to encompass the relevant portion of the artery 2334.

Tissues and/or structures can also be imaged or characterized according to their reflective characteristics, in addition to or in lieu of their absorptive characteristics described above with respect to FIGS. 13A and 13B, across the EMR wavelength spectrum. For example, FIGS. 13C-13E illustrate various graphs of reflectance of different types of tissues or structures across different EMR wavelengths. FIG. 13C is a graphical representation 1050 of an illustrative ureter signature versus obscurants. FIG. 13D is a graphical representation 1052 of an illustrative artery signature versus obscurants. FIG. 13E is a graphical representation 1054 of an illustrative nerve signature versus obscurants. The plots in FIGS. 13C-13E represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

In various instances, select wavelengths for spectral imaging can be identified and utilized based on the anticipated critical structures and/or obscurants at a surgical site (i.e., "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 14 and 15, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 15, for example, which can be measured by the receiver 1108.

Based on the delay between the emitted wave 1124 and the received wave 1125, the time-of-flight sensor system 1104 is configured to determine the distance d (FIG. 14). A time-of-flight timing diagram 1130 for the emitter 1106 and the receiver 1108 of FIG. 14 is shown in FIG. 15. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance d in FIG. 14. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t.$$

where:
$d_A$=the depth of the critical structure 1101;
$d_w$=the distance from the emitter 1106 to the critical structure 1101 (d in FIG. 14); and
$d_t$=the distance from the emitter 1106 (on the distal end of the surgical device 1102) to the surface 1105 of the obscuring tissue 1103.

In one aspect of the present disclosure, referring now to FIG. 16, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the -receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described in various U.S. Patent Applications, which are incorporated by reference herein in the present disclosure.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}$, $d_{2a}$, $d_{3a}$, $d_{1b}$, $d_{2b}$, $d_{2e}$ indicated in FIG. 16.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}$, $d_{2a}$, $d_{3a}$, $d_{1b}$, $d_{2b}$, $d_{2e}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 16, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 16, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization systems disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure (s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

In various instances, clinicians may not know the location of a critical structure with respect to a surgical tool. For example, when a critical structure is embedded in tissue, the clinician may be unable to ascertain the location of the critical structure. In certain instances, a clinician may want to keep a surgical device outside a range of positions surrounding the critical structure and/or away from the visible tissue covering the hidden critical structure. When the location of a concealed critical structure is unknown, the clinician may risk moving too close to the critical structure, which can result in inadvertent trauma and/or dissection of the critical structure and/or too much energy, heat, and/or tension in proximity of the critical structure. Alternatively, the clinician may stay too far away from a suspected location of the critical structure and risk affecting tissue at a less desirable location in an effort to avoid the critical structure.

A surgical visualization system is provided that presents surgical device tracking with respect to one or more critical structures. For example, the surgical visualization system can track the proximity of a surgical device with respect to a critical structure. Such tracking can occur intraoperatively, in real-time, and/or in near real-time. In various instances, the tracking data can be provided to the clinicians via a display screen (e.g. a monitor) of an imaging system.

In one aspect of the present disclosure, a surgical visualization system includes a surgical device comprising an emitter configured to emit a structured light pattern onto a visible surface, an imaging system comprising a camera configured to detect an embedded structure and the structured light pattern on the visible surface, and a control circuit in signal communication with the camera and the imaging system, wherein the control circuit is configured to determine a distance from the surgical device to the embedded structure and provide a signal to the imaging system indicative of the distance. For example, the distance can be determined by computing a distance from the camera to the critical structure that is illuminated with fluoroscopy technology and based on a three-dimensional view of the illuminated structure provided by images from multiple lenses (e.g. a left-side lens and a right-side lens) of the camera. The distance from the surgical device to the critical structure can be triangulated based on the known positions of the surgical device and the camera, for example. Alternative means for determining the distance to an embedded critical structure are further described herein. For example, NIR time-of-flight distance sensors can be employed. Additionally or alternatively, the surgical visualization system can determine a distance to visible tissue overlying/covering an embedded critical structure. For example, the surgical visualization system can identify a hidden critical structure and augment a view of the hidden critical structure by depicting a schematic of the hidden critical structure on the visible structure, such as a line on the surface of the visible tissue. The surgical visualization system can further determine the distance to the augmented line on the visible tissue.

By providing the clinician with up-to-date information regarding the proximity of the surgical device to the concealed critical structure and/or visible structure, as provided by the various surgical visualization systems disclosed herein, the clinician can make more informed decisions regarding the placement of the surgical device relative to the concealed critical structure. For example, the clinician can view the distance between the surgical device and the critical structure in real-time/intraoperatively and, in certain instances, an alert and/or warning can be provided by the imaging system when the surgical device is moved within a predefined proximity and/or zone of the critical structure. In certain instances, the alert and/or warning can be provided when the trajectory of the surgical device indicates a likely collision with a "no-fly" zone in the proximity of the critical structure (e.g. within 1 mm, 2 mm, 5 mm, 10 mm, 20 mm or more of the critical structure). In such instances, the clinician can maintain momentum throughout the surgical procedure without requiring the clinician to monitor a suspected location of the critical structure and the surgical device's proximity thereto. As a result, certain surgical procedures can be performed more quickly, with fewer pauses/interruptions, and/or with improved accuracy and/or certainty, for example. In one aspect, the surgical visualization system can be utilized to detect tissue variability, such as the variability of tissue within an organ to differentiate tumors/cancerous tissue/unhealthy tissue from healthy tissue. Such a surgical visualization system can maximize the removal of the unhealthy tissue while minimizing the removal of the healthy tissue.

Surgical Hub System

The various visualization or imaging systems described herein can be incorporated into a surgical hub system, such as is illustrated in connection with FIGS. 17-19 and described in further detail below.

Referring to FIG. 17, a computer-implemented interactive surgical system 2100 includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. In one example, as illustrated in FIG. 17, the surgical system 2102 includes a visualization system 2108, a robotic system 2110, and a handheld intelligent surgical instrument 2112, which are configured to communicate with one another and/or the hub 2106. In some aspects, a surgical system 2102 may include an M number of hubs 2106, an N number of visualization systems 2108, an O number of robotic systems 2110, and a P number of handheld intelligent surgical instruments 2112, where M, N, O, and P are integers greater than or equal to one.

FIG. 18 depicts an example of a surgical system 2102 being used to perform a surgical procedure on a patient who is lying down on an operating table 2114 in a surgical operating room 2116. A robotic system 2110 is used in the surgical procedure as a part of the surgical system 2102. The robotic system 2110 includes a surgeon's console 2118, a patient side cart 2120 (surgical robot), and a surgical robotic hub 2122. The patient side cart 2120 can manipulate at least one removably coupled surgical tool 2117 through a minimally invasive incision in the body of the patient while the surgeon views the surgical site through the surgeon's console 2118. An image of the surgical site can be obtained by a medical imaging device 2124, which can be manipulated by the patient side cart 2120 to orient the imaging device 2124. The robotic hub 2122 can be used to process the images of the surgical site for subsequent display to the surgeon through the surgeon's console 2118.

Other types of robotic systems can be readily adapted for use with the surgical system 2102. Various examples of robotic systems and surgical tools that are suitable for use with the present disclosure are described in various U.S. Patent Applications, which are incorporated by reference herein in the present disclosure.

Various examples of cloud-based analytics that are performed by the cloud 2104, and are suitable for use with the present disclosure, are described in various U.S. Patent Applications, which are incorporated by reference herein in the present disclosure.

In various aspects, the imaging device 2124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 2124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 2124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in various U.S. Patent Applications that are incorporated by reference herein in the present disclosure. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 2124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 2108 includes one or more imaging sensors, one or more image-processing units, one or more storage arrays, and one or more displays that are strategically arranged with respect to the sterile field, as illustrated in FIG. 18. In one aspect, the visualization system 2108 includes an interface for HL7, PACS, and EMR. Various components of the visualization system 2108 are described in various U.S. Patent Applications that are incorporated by reference herein in the present disclosure.

As illustrated in FIG. 18, a primary display 2119 is positioned in the sterile field to be visible to an operator at the operating table 2114. In addition, a visualization tower 21121 is positioned outside the sterile field. The visualization tower 21121 includes a first non-sterile display 2107 and a second non-sterile display 2109, which face away from each other. The visualization system 2108, guided by the hub 2106, is configured to utilize the displays 2107, 2109, and 2119 to coordinate information flow to operators inside and outside the sterile field. For example, the hub 2106 may cause the visualization system 2108 to display a snapshot of a surgical site, as recorded by an imaging device 2124, on a non-sterile display 2107 or 2109, while maintaining a live feed of the surgical site on the primary display 2119. The snapshot on the non-sterile display 2107 or 2109 can permit a non-sterile operator to perform a diagnostic step relevant to the surgical procedure, for example.

In one aspect, the hub 2106 is also configured to route a diagnostic input or feedback entered by a non-sterile operator at the visualization tower 21121 to the primary display 2119 within the sterile field, where it can be viewed by a sterile operator at the operating table. In one example, the input can be in the form of a modification to the snapshot displayed on the non-sterile display 2107 or 2109, which can be routed to the primary display 2119 by the hub 2106.

Referring to FIG. 18, a surgical instrument 2112 is being used in the surgical procedure as part of the surgical system 2102. The hub 2106 is also configured to coordinate information flow to a display of the surgical instrument 2112, as is described in various U.S. Patent Applications that are incorporated by reference herein in the present disclosure. A diagnostic input or feedback entered by a non-sterile operator at the visualization tower 21121 can be routed by the hub 2106 to the surgical instrument display 2115 within the sterile field, where it can be viewed by the operator of the surgical instrument 2112. Example surgical instruments that are suitable for use with the surgical system 2102 are described in various U.S. Patent Applications that are incorporated by reference herein in the present disclosure.

FIG. 19 illustrates a computer-implemented interactive surgical system 2200. The computer-implemented interactive surgical system 2200 is similar in many respects to the computer-implemented interactive surgical system 2100. The surgical system 2200 includes at least one surgical hub 2236 in communication with a cloud 2204 that may include a remote server 2213. In one aspect, the computer-implemented interactive surgical system 2200 comprises a surgical hub 2236 connected to multiple operating theater devices such as, for example, intelligent surgical instruments, robots, and other computerized devices located in the operating theater. The surgical hub 2236 comprises a communications interface for communicably coupling the surgical hub 2236 to the cloud 2204 and/or remote server 2213. As illustrated in the example of FIG. 19, the surgical hub 2236 is coupled to an imaging module 2238 that is coupled to an endoscope 2239, a generator module 2240 that is coupled to an energy device 2421, a smoke evacuator module 2226, a suction/irrigation module 2228, a communication module 2230, a processor module 2232, a storage array 2234, a smart device/instrument 2235 optionally coupled to a display 2237, and a non-contact sensor module 2242. The operating theater devices are coupled to cloud computing resources and data storage via the surgical hub 2236. A robot hub 2222 also may be connected to the surgical hub 2236 and to the cloud computing resources. The devices/instruments 2235, visualization systems 2209, among others, may be coupled to the surgical hub 2236 via wired or wireless communication standards or protocols, as described herein. The surgical hub 2236 may be coupled to a hub display 2215 (e.g., monitor, screen) to display and overlay images received from the imaging module, device/instrument display, and/or other visualization systems 208. The hub display also may display data received from devices connected to the modular control tower in conjunction with images and overlaid images.

Situational Awareness

The various visualization systems or aspects of visualization systems described herein can be utilized as part of a situational awareness system that can be embodied or executed by a surgical hub 2106, 2236 (FIGS. 17-19). In particular, characterizing, identifying, and/or visualizing surgical instruments or other surgical devices (including their positions, orientations, and actions), tissues, structures, users, and other things located within the surgical field or the operating theater can provide contextual data that can be utilized by a situational awareness system to infer the type of surgical procedure or a step thereof being performed, the type of tissue(s) and/or structure(s) being manipulated by the surgeon, and so on. This contextual data can then be utilized by the situational awareness system to provide alerts to users, suggest subsequent steps or actions for the users to undertake, prepare surgical devices in anticipation for their use (e.g., activate an electrosurgical generator in anticipation of an electrosurgical instrument being utilized in a subsequent step of the surgical procedure), control surgical instruments intelligently (e.g., customize surgical instrument operational parameters based on each patient's particular health profile), and so on.

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control modular device incorrectly or suboptimally given the particular context-free sensed data. Modular devices can include any surgical devices that is controllable by a situational awareness system, such as visualization system devices (e.g., a camera or display screen), surgical instruments (e.g., an ultrasonic surgical instrument, an electrosurgical instrument, or a surgical stapler), and other surgical devices (e.g., a smoke evacuator). For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 20 illustrates a diagram of a situationally aware surgical system 2400, in accordance with at least one aspect of the present disclosure. In some exemplifications, the data sources 2426 include, for example, the modular devices 2402 (which can include sensors configured to detect parameters associated with the patient and/or the modular device itself), databases 2422 (e.g., an EMR database containing patient records), and patient monitoring devices 2424 (e.g., a blood pressure (BP) monitor and an electrocardiography (EKG) monitor).

A surgical hub 2404, which may be similar to the hub 106 in many respects, can be configured to derive the contextual information pertaining to the surgical procedure from the data based upon, for example, the particular combination(s) of received data or the particular order in which the data is received from the data sources 2426. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2404 to derive or infer information related to the surgical procedure from received data can be referred to as "situational awareness." In one exemplification, the surgical hub 2404 can incorporate a situational awareness system, which is the hardware and/or programming associated with the surgical hub 2404 that derives contextual information pertaining to the surgical procedure from the received data.

The situational awareness system of the surgical hub 2404 can be configured to derive the contextual information from the data received from the data sources 2426 in a variety of different ways. In one exemplification, the situational awareness system includes a pattern recognition system, or machine learning system (e.g., an artificial neural network), that has been trained on training data to correlate various inputs (e.g., data from databases 2422, patient monitoring devices 2424, and/or modular devices 2402) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2402. In one exemplification, the contextual information received by the situational awareness system of the surgical hub 2404 is associated with a particular control adjustment or set of control adjustments for one or more modular devices 2402. In another exemplification, the situational awareness system includes a further machine learning system, lookup table, or other such system, which generates or retrieves one or more control adjustments for one or more modular devices 2402 when provided the contextual information as input.

A surgical hub 2404 incorporating a situational awareness system provides a number of benefits for the surgical system 2400. One benefit includes improving the interpretation of sensed and collected data, which would in turn improve the processing accuracy and/or the usage of the data during the course of a surgical procedure. To return to a previous example, a situationally aware surgical hub 2404 could determine what type of tissue was being operated on; therefore, when an unexpectedly high force to close the surgical instrument's end effector is detected, the situationally aware surgical hub 2404 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2404 could infer whether a surgical procedure being performed is a thoracic or an abdominal procedure, allowing the surgical hub 2404 to determine whether the tissue clamped by an end effector of the surgical stapling and cutting instrument is lung (for a thoracic procedure) or stomach (for an abdominal procedure) tissue. The surgical hub 2404 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2404 could determine whether the surgical site is under pressure (by determining that the surgical procedure is utilizing insufflation) and determine the procedure type. As a procedure type is generally performed in a specific body cavity, the surgical hub 2404 could then control the motor rate of the smoke evacuator appropriately for the body cavity being operated in. Thus, a situationally aware surgical hub 2404 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 2404 could determine whether the surgical procedure is an arthroscopic procedure. The surgical hub 2404 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2404 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2404 can be configured to adjust the energy level for the ultrasonic surgical instrument or RF electrosurgical instrument throughout the course of a surgical procedure, rather than just on a procedure-by-procedure basis. A situationally aware surgical hub 2404 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2426 to improve the conclusions that the surgical hub 2404 draws from one data source 2426. A situationally aware surgical hub 2404 could augment data that it receives from the modular devices 2402 with contextual information that it has built up regarding the surgical procedure from other data sources 2426. For example, a situationally aware surgical hub 2404 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2404 can be further configured to compare a physiologic measurement (e.g., blood pressure sensed by a BP monitor communicably connected to the surgical hub 2404) with the visual or image data of hemostasis (e.g., from a medical imaging device 124 (FIG. 2) communicably coupled to the surgical hub 2404) to make a determination on the integrity of the staple line or tissue weld. In other words, the situational awareness system of the surgical hub 2404 can consider the physiological measurement data to provide additional context in analyzing the visualization data. The additional context can be useful when the visualization data may be inconclusive or incomplete on its own.

Another benefit includes proactively and automatically controlling the paired modular devices 2402 according to the particular step of the surgical procedure that is being performed to reduce the number of times that medical personnel are required to interact with or control the surgical system 2400 during the course of a surgical procedure. For example, a situationally aware surgical hub 2404 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2404 could determine whether the current or subsequent step of the surgical procedure requires a different view or degree of magnification on the display according to the feature(s) at the surgical site that the surgeon is expected to need to view. The surgical hub 2404 could then proactively change the displayed view (supplied by, e.g., a medical imaging device for the visualization system 108) accordingly so that the display automatically adjusts throughout the surgical procedure.

As yet another example, a situationally aware surgical hub 2404 could determine which step of the surgical procedure is being performed or will subsequently be performed and whether particular data or comparisons between data will be required for that step of the surgical procedure. The surgical hub 2404 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2404 could determine whether the operating theater is setup properly or optimally for the surgical procedure to be performed. The surgical hub 2404 can be configured to determine the type of surgical procedure being performed, retrieve the corresponding checklists, product location, or setup needs (e.g., from a memory), and then compare the current operating theater layout to the standard layout for the type of surgical procedure that the surgical hub 2404 determines is being performed. In one exemplification, the surgical hub 2404 can be configured to compare the list of items for the procedure scanned by a suitable scanner for example and/or a list of devices paired with the surgical hub 2404 to a recommended or anticipated manifest of items and/or devices for the given surgical procedure. If there are any discontinuities between the lists, the surgical hub 2404 can be configured to provide an alert indicating that a particular modular device 2402, patient monitoring device 2424, and/or other surgical item is missing. In one exemplification, the surgical hub 2404 can be configured to determine the relative distance or position of the modular devices 2402 and patient monitoring devices 2424 via proximity sensors, for example. The surgical hub 2404 can compare the relative positions of the devices to a recommended or anticipated layout for the particular surgical procedure. If there are any discontinuities between the layouts, the surgical hub 2404 can be configured to provide an alert indicating that the current layout for the surgical procedure deviates from the recommended layout.

As another example, a situationally aware surgical hub 2404 could determine whether the surgeon (or other medical personnel) was making an error or otherwise deviating from the expected course of action during the course of a surgical procedure. For example, the surgical hub 2404 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2404 determined is being performed. In one exemplification, the surgical hub 2404 can be configured to provide an alert indicating that an unexpected action is being performed or an unexpected device is being utilized at the particular step in the surgical procedure.

Overall, the situational awareness system for the surgical hub 2404 improves surgical procedure outcomes by adjusting the surgical instruments (and other modular devices 2402) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2402 in the surgical theater according to the specific context of the procedure.

Referring now to FIG. 21, a timeline 2500 depicting situational awareness of a hub, such as the surgical hub 106 or 206 (FIGS. 1-11), for example, is depicted. The timeline 2500 is an illustrative surgical procedure and the contextual information that the surgical hub 106, 206 can derive from the data received from the data sources at each step in the surgical procedure. The timeline 2500 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 2502 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 2504, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 2506, the medical personnel scan the patient band via a scanner that is communicably connected to the surgical hub 106, 206. The surgical hub 106, 206 can then confirm the patient's identity based on the scanned data.

Fourth step 2508, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 2510, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 2512, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 2512, the pre-operative portion of the lung segmentectomy procedure is completed and the operative portion begins.

Seventh step 2514, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 2516, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 2504 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 2518, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 2520, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 2522, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 2524, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 2524, the incisions are closed up and the post-operative portion of the procedure begins.

Thirteenth step 2526, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 2528 is that the medical personnel remove the various patient monitoring devices from the patient. The surgical hub 2106, 2236 can thus infer that the patient is being transferred to a recovery room when the hub loses EKG, BP, and other data from the patient monitoring devices. As can be seen from the description of this illustrative procedure, the surgical hub 2106, 2236 can determine or infer when each step of a given surgical procedure is taking place according to data received from the various data sources that are communicably coupled to the surgical hub 2106, 2236.

Situational awareness is further described in various U.S. Patent Applications that are incorporated by reference herein in the present disclosure, which is herein incorporated by reference in its entirety. In certain instances, operation of a robotic surgical system, including the various robotic surgical systems disclosed herein, for example, can be controlled by the hub 2106, 2236 based on its situational awareness and/or feedback from the components thereof and/or based on information from the cloud 2104 (FIG. 17).

Imaging System Utilizing Fusion Imagery

One issue inherent to surgical procedures where surgeons rely upon imaging systems 142 (FIG. 2) is obstructions to the camera 144 (FIG. 2) that impinge upon the imaging systems' 142 ability to visualize the surgical site and, thus, the surgeon's ability to perform the surgical tasks required for the procedure. Obstructions can include, for example, fluid (e.g., blood) on the lens of the camera 144, on the surface of the body cavity, or otherwise present at the surgical site; smoke generated by electrosurgical instruments or other aerosols present within the body cavity; and/or tissues or other structures overlaying the target tissues or structures. A surgical system could be configured to utilize various imaging techniques to compensate for obstructions including multispectral imaging of sub-regions of the FOV of the camera 144, interpolating sub-regions of prior image frames captured by the camera 144, comparative multispectral analysis of captured images, and so on.

In one general aspect, the present disclosure is directed to a surgical system configured to utilize segments of images captured at a sampling rate via an imaging system 142 a multispectral light source to minimize the impairment of visualization due to various obstructions (e.g., surgical smoke). In one aspect, the surgical system can be configure to combine hyperspectral imaging with visible light imaging to minimize image interference caused by obstructions. The surgical system can, for example, be configured to detect aspects of underlying or obstructed portions of surgical instruments, the surgical site, or the surroundings by utilizing a separate wavelength or range of wavelengths of EMR. For example, the surgical system can utilize a frame from a sequential scanning device to transmit separate wavelength (s) of EMR, include a hyperspectral imaging device configured to scan both within and outside of the visible light spectrum, or a second imaging system configured to emit EMR at a different length than the first or primary imaging system. Accordingly, the surgical system can be configured to identify obstructed portions of image frames at a particular wavelength or set of wavelengths and interpolate or substitute portions of the obstructed image portions with unobstructed image portions of image frames obtained at other EMR wavelengths in order to provide a fully visualized, unobstructed image of the surgical site for the users.

In aspects utilizing an imaging system including a hyperspectral imaging device, the hyperspectral imaging device could scan at a particular rate (e.g., 240 frames per second) that would allow a portion of the emitted scan to include EMR from a near IR or UV laser source. Since those EMR at those wavelengths are not affected in the same manner as visible light to obstructions such as surgical smoke, fluids, and so on, the hyperspectral imaging device could be utilized to obtain images of shapes, contours, or features that exist in both the hyperspectral image and the corresponding visible light image. A control system of the surgical system, such as the control system 133 illustrated in FIG. 2, could then be configured to substitute obstructed portions of the images obtained utilizing visible light with the corresponding detected hyperspectral feature(s) or image portion(s) to complete the visualization for the surgeon. As another example, the imaging system can include a tunable EMR source (e.g., the spectral light source 150) that is controllable by the control system 133 to emit EMR at a wavelength or set of wavelengths where absorption of the EMR by water is at a minimum (e.g., in the visible blue-green wavelength range) since obscuration by water or water-containing fluids is especially likely during a surgical procedure. As another example, the surgical system could further include a second imaging system in addition to the first primary imaging system (e.g., the imaging system 142 shown in FIG. 2). In this example, the first imaging system 142 could be configured for imaging of the visible or near visible EMR spectrums and the second imaging system could be configured for imaging of a different wavelength spectrum(s) (e.g., long-wave IR (LWIR)). Accordingly, the second imaging system could be activated or otherwise utilized by the surgical system as needed when the first imaging system is being obscured. In these various aspects, the surgical system would minimize the amount of cleaning required for the camera 144 (e.g., to remove obstructions from the image sensor 135 or other scanning array) and prevent temporary loss of sight of the surgical field due to obstructions between the camera 144 and the surgical field (e.g., surgical smoke or insufflation gasses).

In particular examples, the imaging or visualization systems are described as including a hyperspectral imaging device or as utilizing hyperspectral imaging techniques. However, it should be noted that hyperspectral imaging is one particular type of multispectral imaging. In hyperspectral imaging, the wavelength "bins" are continuous, so hyperspectral imaging techniques are utilizing the entire EMR spectrum. Conversely, multispectral can mean that the "bins" are separated. In other words, a multispectral imaging system may sense EMR within, for example, the visible, mid-wave IR (MWIR), and LWIR portions of the EMR spectrum (there can be gaps that a multispectral imaging system does not sense in, e.g., the near IR (NIR) portion of the EMR spectrum and/or between MWIR and LWIR portions). The imaging or visualization systems and methods described herein should not be construed to be limited to any particular example, including examples describing hyperspectral imaging. In fact, the imaging or visualization systems and methods can broadly utilize any multispectral imaging devices and techniques.

In order to assist in the understanding of the aforementioned systems and methods, various examples will be described within the context of a video-assisted thoracoscopic surgery (VATS) procedure. It should be understood that this is simply for illustrative purposes though and that the described systems and methods are applicable to other contexts and/or surgical procedures, however. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Accordingly, FIG. 22 is a diagram of a surgical system 3000 during the performance of a surgical procedure on a lung 3010, in accordance with at least one aspect of the present disclosure. A surgical system 3000 for performing a video-assisted surgical procedure can include a variety of different surgical devices, including an imaging device 3002, a grasper 3004, an electrosurgical instrument 3006 or another surgical instrument, and a smoke evacuator 3008. Further, the surgical system 3000 can include or be coupled to a surgical hub 2106, 2236 (FIGS. 17-19), a visualization system 2108 (FIGS. 17-19) or an imaging system 142 (FIG. 2), a control system 133 (FIG. 2), a robotic system 2110 (FIGS. 17-19), and any other systems or devices described herein. The imaging device 3002 can include a camera 144 (FIG. 2), a spectral light source 150 (FIG. 2), a structured light source 152 (FIG. 2), any other imaging emitters or receivers described herein, or combinations thereof. The imaging device 3002 can be configured to capture and provide images or video of the surgical site within a FOV 3020 to a display screen (e.g., the display 146 as in FIG. 2) for viewing by a user (e.g., a surgeon). The imaging device 3002 can be configured to sense EMR within or outside of the visible light portion of the EMR spectrum and thereby visualize tissues and/or structures that are either visible or invisible to the naked eye. Based on the visualization provided by the imaging system 142 associated with the imaging device 3002, the surgeon can then control the surgical devices to manipulate the tissues and/or structures to perform the surgical procedure.

During a surgical procedure, various obscurants, such as surgical smoke clouds 3014 or other aerosols, fluids, gasses, tissues, structures, and so on, can move across the FOV 3020 of the imaging device(s) 3002 and thereby prevent the imaging system 132 from being able to fully visualize the surgical site, which can in turn negatively impact the surgeon's ability to perform the procedure. Many surgical systems 3000 include smoke evacuators 3008 to remove surgical smoke clouds 3014, other aerosols, and gasses from the body cavity being operated on. However, smoke evacuators 3008 may not be sufficient to remove all obscurants or there may be a delay associated with the removal of the obscurants during which the surgeon is unable to properly visualize the surgical site. Accordingly, systems and methods are needed to compensate for the presence of obscurants and allow for visualization of a surgical site through those obscurants.

In one aspect, an imaging system, such as the imaging system 142 illustrated in FIG. 2, can be configured to utilize hyperspectral imaging and image fusion techniques to allow for visualization through obscurants. For example, FIG. 23 is a diagram of an imaging device 3002 faced with multiple obscurants. In this example, the target of the surgical procedure is a subsurface tumor 3038. However, to actually visualize the tumor 3038, the imaging device 3002 would have to compensate for a number of different obscurants, including fluid 3030 present on the lens of the imaging device 3002, surgical smoke 3032 present within the body cavity, blood 3034 on the surface of the tissue 3036, the tissue 3036 itself, and structures 3040 located throughout the tissue 3036. In one aspect, the imaging device 3002 can be a hyperspectral imaging device that is configured to sense EMR across the wavelength spectrum. EMR interacts differently with various objects at different wavelengths. In particular, certain wavelengths of EMR may not be absorbed by particular obscurants at particular wavelengths or wavelength ranges. Therefore, by sensing EMR at multiple portions of the EMR spectrum, the imaging system 142 can visualize through obscurants by sensing EMR at wavelengths that are not absorbed by the obscurants. Further, the wavelengths sensed by the imaging device 3002 can be selected to sense at wavelengths that are non-interactive (or substantially non-interactive) with typical or expected obscurants. In the depicted example, the imaging device 3002 can be configured to sense EMR within the visible light, MWIR, and LWIR portions of the EMR spectrum.

In one aspect, a control system can be configured to utilize multispectral (e.g., hyperspectral) imaging to visualize a surgical site at multiple portions of the EMR spectrum and then provide a visualization to a user that is free from obscurants by replacing obscured portions of an image captured at one wavelength range with a corresponding portion of an image that is captured at another portion of the wavelength range that is not absorbed by the obscurant. One example of such an algorithm is shown in FIG. 24, which is a logic flow diagram of a process 3050 for generating fused images utilizing a multispectral EMR source. In the following description of the process 3050, reference should also be made to FIG. 2 and FIG. 23. The process 3050 can be embodied as, for example, instructions stored in a memory 134 coupled to a control circuit 132 that, when executed by the control circuit 132, cause the control circuit 132 to perform the enumerated steps of the process 3050. For brevity, the process 3050 is described as being executed by the control circuit 132; however, it should be understood that the process 3050 can be executed by other combinations of hardware, software, and/or firmware.

Accordingly, the control circuit 132 executing the process 3050 can cause the imaging system 142 to sense 3052 EMR (e.g., via the imaging device 3002) at a first wavelength range (e.g., visible light) from the surgical site and then generate 3054 a corresponding first image therefrom. Correspondingly, the control circuit 132 can cause the imaging system 142 to sense 3056 EMR (e.g., via the imaging device 3002) at a second wavelength range (e.g., MWIR or LWIR) from the surgical site and then generate 3058 a corresponding second image therefrom.

Accordingly, the control circuit 132 can determine 3060 whether the first image is at least partially obstructed. The control circuit 132 can be configured to make this determination by detecting obstructions utilizing object recognition and other computer vision techniques. If the first image is not at least partially obstructed, then the process 3050 proceeds along the NO branch and the control circuit 132 can continue sensing 3052, 3054 EMR and generating 3054, 3058 corresponding images, as described above. If the first image is at least partially obstructed (i.e., there is an obstruction present within the image), then the process 3050 proceeds along the YES branch and the control circuit 132 can generate 3062 a third image by replacing the obstructed portion of the first image with the corresponding portion of the second image. If the second wavelength range was selected such that it is not absorbed by the obscurant, then the corresponding portion of the second image should be unobstructed. Therefore, the third image should provide an unobstructed visualization of the surgical site for viewing by the surgeon.

For the brevity, the process 3050 is described in the context of generating and combining two images captured at two different wavelength ranges; however, the imaging system 142 can be configured to sense and generate images at any number of wavelength ranges. FIG. 23, for example, illustrates an implementation that combines image data from at least three different EMR wavelength ranges to generate the resulting image. Each of the depicted first image 3042a, second image 3042b, third image 3042c, and fourth image 3042d include an array of pixels 3043 that collectively visualize the surgical site at the corresponding EMR wavelength range. In this example, the first image 3042a was captured utilizing the visible light portion of the EMR spectrum and includes a first unobstructed portion 3044a, with the remaining portions of the image 3042a being obstructed; the second image 3042b was captured utilizing the MWIR portion of the EMR spectrum and includes a second unobstructed portion 3044b; and the third image 3042c was captured utilizing the LWIR portion of the EMR spectrum and includes a third unobstructed portion 3044c. The control system 133 can also be configured to perform various image processing techniques on the various generated images to improve the visualizations provided thereby. For example, the fourth image 3042d was also captured utilizing the visible light portion of the EMR spectrum and thus can correspond to the first image 3042a, but includes additional image processing to identify a fluid (water) obstructed portion 3044d. Accordingly, the corresponding portion of the first image 3042a could be filtered at a corresponding wavelength or wavelength range (e.g., the blue-green portion of the visible light spectrum) to remove the obstruction. Accordingly, a control circuit 132 executing the process 3050 can be configured to generate a combination or fused image 3070 from the aforementioned initial images 3042a, 3042b, 3042c, 3042d. The fused image 3070 can include a first portion 3072 corresponding to the unobstructed portion 3044a of the first image 3042a generated from the visible light portion of the EMR spectrum, a second portion 3074 corresponding to the unobstructed portion 3044b of the second image 3042b generated from the MWIR portion of the EMR spectrum, a third portion 3076 corresponding to the unobstructed portion 3044c of the third image 3042c generated from the LWIR portion of the EMR spectrum, and a fourth portion 3078 corresponding to the obstructed portion 3044d of an image generated from the visible light portion of the EMR spectrum, but post-processed to remove the blue-green portion of the visible light spectrum. Each of the aforementioned image portions 3072, 3074, 3076, 3078 can be fused together by the control system 133 to generate the fused image 3070 that provides for an unobstructed visualization of the tumor 3038 and any other relevant structures 3040.

Another technique that can be utilized to compensate for obscurants present at the surgical site is to image sub-region interpolation, whereby portions of an image that are obscured, damaged, or otherwise interfered with can be replaced by corresponding portions of images from a synchronized image set. For example, a surgical control system could utilize lucky-region fusion (LRF) techniques to enhance the quality of the visualization provided to users by using multiple image frames. In one aspect, a control system can be configured to provide a visualization to a user that is free from obscurants by replacing obscured portions of an image with an unobscured portion of a previously captured image. One example of such an algorithm is shown in FIG. 26, which is a logic flow diagram of a process 3100 for generating fused images utilizing multiple image frames. In the following description of the process 3100, reference should also be made to FIG. 2 and FIGS. 27-29. The process 3100 can be embodied as, for example, instructions stored in a memory 134 coupled to a control circuit 132 that, when executed by the control circuit 132, cause the control circuit 132 to perform the enumerated steps of the process 3100. For brevity, the process 3100 is described as being executed by the control circuit 132; however, it should be understood that the process 3100 can be executed by other combinations of hardware, software, and/or firmware.

Accordingly, the control circuit 132 executing the process 3100 can (e.g., via the imaging system 142) generate 3102 an image of the surgical site and then determine 3104 whether the image is at least partially obstructed, as described above. For example, FIG. 27 is a diagram of a series 3150 of n image frames 3160 captured by the imaging system 142. The nth image frame 3160 can be the most recently captured image frame 3160, the (n−1)th image frame 3160 can be the immediately previously captured image frame 3160, and so on. Each of the image frames 3160 comprises a number of pixels 3151, which may or may not correspond to the pixels or cells of an image sensor 135, for example. As can be seen in FIG. 27, the image frames 3160 can include unobstructed portions 3162 and obstructed portions 3164. In evaluating the nth image frame 3160 specifically, a control circuit 123 executing the process 3100 would determine that the nth image frame 3160 is at least partially obstructed because it includes an obstructed portion 3164 of pixels 3151.

If the control circuit 132 determines 3104 that the image is not at least partially obstructed, then the process 3100 proceeds along the NO branch and the control circuit 132 can cause the imaging system 142 to continue generating images (i.e., visualizing the surgical site) for visualization of the surgical site, as described above. If the control circuit 132 determines 3104 that the image is at least partially constructed (e.g., as shown in the nth image frame 3160), then the process proceeds along the YES branch and the control circuit 132 can retrieve 3106 a prior image from the image set 3150. In one aspect, the control circuit 132 can successively retrieve 3106 one or more prior images from the image set 3150 until the control circuit 132 has located corresponding unobstructed image portions with which they replace the obstructed portion(s) of the first image.

Accordingly, the control circuit 132 can generate 3108 an updated image from the original image and the one or more prior images retrieved from the image set 3150. For example, FIG. 28 and FIG. 29 illustrated an updated or fused image 3152 generated from multiple successive image frames 3160. In this particular example, n is equal to 60, although this is simply for illustrative purposes. In FIG. 28, the number indicated within each pixel 3151 corresponds to the image frame 3160 from which the particular pixel 3151 was extracted. As can be seen, the fused image 3152 is generated from a combination of pixels 3151 across a number of different image frames 3160. Specifically, image frames 3160 55 through 60, which in turn correspond to the (n−5)th through nth image frames 3160, respectively, as shown in FIG. 27. Accordingly, the control circuit 132 can be configured to repeatedly retrieve 3106 a preceding image from the image set 3150 captured by the imaging system 142 and extract the image portions, such as the pixels 3151, that are unobstructed in the retrieved image, but correspond to pixels 3151 that are obstructed in the successive image. The control circuit 132 can repeat this process until a completely or substantially unobstructed collection of image portions from the image set 3150 have been retrieved and then fuse the image portions together to generate 3108 an updated image. A resulting fused image 3152 generated using this technique is shown in FIG. 29, illustrating how a tumor 3038 and structures 3140, such as vessels, would be visualized for users from an initial partially obstructed image.

Another technique that can be utilized to compensate for obscurants present at the surgical site is to perform a comparative analysis of a set of synchronized imaging devices. A control system 133 could be configured to interlace multiple image portions generated by multiple synchronized imaging devices to generate a fused image. In particular, a portion of an image generated by a first or primary imaging system (e.g., the imaging system 142 shown in FIG. 2) could be substituted with a corresponding portion of an image generated by a secondary imaging system. In particular, a set of imaging systems could be configured to time index their scans. Obscured, corrupted, indistinct, or otherwise interfered with portions of a first scan generated by a first imaging system could be replaced with clearer and/or verified portions of a second scan (which is time indexed in accordance with the first scan) generated by a second imaging system. If image data is missing, corrupted, or obscured in the imaging of the primary dynamic data set generated by a first imaging system, a secondary scan from another imaging system (which could also be sensing in another wavelength or range of wavelengths) could be utilized by a control system 133 to sharpen, replace, or interpolate the primary image to improve the visualization of the surgical site for users.

Surgical System Control Based on Multiple Sensed Parameters

One issue that is inherent to any surgical procedures and surgical instruments is controlling the surgical instruments in an ideal manner for the given patient and/or tissue conditions. To that end, some surgical instruments include sensors for sensing various parameters associated with the surgical instruments and/or the tissues being manipulated by the surgical instruments. However, some sensed data can be indicative of different states or conditions of the tissue and can thus be inconclusive absent additional data. Accordingly, a surgical system could incorporate data from an imaging system with other sensed data to resolve ambiguities and control surgical instruments ideally according to the determined state/condition of the tissue.

In one general aspect, the present disclosure is directed to a control system configured to utilize of two sources of related, but not identical, data sources to differentiate between different states of a tissue being acted on by a surgical instrument. Such states that include, for example, fluid flow within the tissue and thermal impacts of energy directed by a surgical instrument on the tissue. The control system can be configured to control a surgical instrument, such as the surgical instrument 3290 described below.

FIG. 30 is a schematic diagram of a surgical instrument 3290 configured to control various functions, in accordance with at least one aspect of the present disclosure. In one aspect, the surgical instrument 3290 is programmed to control distal translation of a displacement member such as the closure member 3264. The surgical instrument 3290 comprises an end effector 3292 that may comprise a clamp arm 3266, a closure member 3264, and an ultrasonic blade 3268, which may be interchanged with or work in conjunction with one or more RF electrodes 3296 (shown in dashed line). The ultrasonic blade 3268 is coupled to an ultrasonic transducer 3269 driven by an ultrasonic generator 3271.

In one aspect, sensors 3288 may be implemented as a limit switch, electromechanical device, solid-state switches, Hall-effect devices, MR devices, GMR devices, magnetometers, among others. In other implementations, the sensors 3288 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 3288 may include electrical conductorless switches, ultrasonic switches, accelerometers, and inertial sensors, among others.

In one aspect, the position sensor 3284 may be implemented as an absolute positioning system comprising a magnetic rotary absolute positioning system implemented as an AS5055EQFT single-chip magnetic rotary position sensor available from Austria Microsystems, AG. The position sensor 3284 may interface with the control circuit 3260 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 3284 may be omitted. Where the motor 3254 is a stepper motor, the control circuit 3260 may track the position of the closure member 3264 by aggregating the number and direction of steps that the motor has been instructed to execute. The position sensor 3284 may be located in the end effector 3292 or at any other portion of the instrument.

The control circuit 3260 may be in communication with one or more sensors 3288. The sensors 3288 may be positioned on the end effector 3292 and adapted to operate with the surgical instrument 3290 to measure the various derived parameters such as gap distance versus time, tissue compression versus time, and anvil strain versus time. The sensors 3288 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 3292. The sensors 3288 may include one or more sensors.

An RF energy source 3294 is coupled to the end effector 3292 and is applied to the RF electrode 3296 when the RF electrode 3296 is provided in the end effector 3292 in place of the ultrasonic blade 3268 or to work in conjunction with the ultrasonic blade 3268. For example, the ultrasonic blade is made of electrically conductive metal and may be employed as the return path for electrosurgical RF current. The control circuit 3260 controls the delivery of the RF energy to the RF electrode 3296.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

In various aspects, the sensors 3288 of the surgical instrument 3290 can include sensors configured to detect or take measurements of various electrical parameters associated with a tissue acted on by the surgical instrument 3290, such as the capacitance or impedance of the tissue. In various aspects, the sensors 3288 can also include sensors configured to detect or take measurements of various physical parameters associated with the tissue acted on by the surgical instrument 3290, such as the temperature, viscoelastic compression (e.g., the tissue creep, time to stability, or rate of initial loading), or thickness (e.g., which can be detected upon first contact of the jaws with the tissue). Further, the image sensor 135 of the control system 133 illustrated in FIG. 2 can be utilized to detect or take measurements of various tissue parameters based on the EMR emitted by the imaging system 142 using the various techniques described above. For example, the image sensor 135 can be configured to detect the refractivity of the tissue at various wavelengths, the polarization of EMR/light reflected by the tissue, passive IR emissions by the tissue, or Doppler wavelength shift associated with the tissue. Any of these imaging-based parameters can be utilized in conjunction with other sensed parameters (e.g., electrical or physical parameters) to ascertain the state or condition of the tissue that may not be directly ascertainable via the parameters individually.

In one aspect, a control system can be configured to control one or more operational parameters associated with the surgical system based on the state or condition of the tissue being acted on by a surgical instrument, which can be determined based on parameters sensed by the imaging system and other sensors. One example of such an algorithm is shown in FIG. 31, which is a logic flow diagram of a process 3300 for controlling a surgical system according to sensed parameters. In the following description of the process 3300, reference should also be made to FIG. 2 and FIG. 30. The process 3300 can be embodied as, for example, instructions stored in a memory 134 coupled to a control circuit 132 that, when executed by the control circuit 132, cause the control circuit 132 to perform the enumerated steps of the process 3300. For brevity, the process 3300 is described as being executed by the control circuit 132; however, it should be understood that the process 3300 can be executed by other combinations of hardware, software, and/or firmware.

Accordingly, a control circuit 132 executing the process 3300 can receive 3302 a measurement of a first tissue parameter via the imaging system 142. As noted previously, the first tissue parameter can include, for example, the refractivity of the tissue at various wavelengths, the polarization of light reflected by the tissue, passive IR emissions by the tissue, or Doppler wavelength shift associated with the tissue.

Accordingly, the control circuit 132 can receive 3304 a measurement of a second tissue parameter via the sensor(s) 788. As noted previously, the second tissue parameter can include, for example, various electrical and/or physical characteristics of the tissue, such as the temperature, viscoelastic compression, or thickness of the tissue.

Accordingly, the control circuit 132 can determine 3306 a state or condition of the tissue based on the combination of the measurements of the received 3302, 3304 tissue parameters and then control 3308 the surgical instrument 3290 accordingly. The same measurement value for various electrical and/or physical characteristics of the tissue can be indicative of different conditions of the tissue, which can in turn necessitate different control adjustments to be applied to the surgical instrument 3290. Absent additional or supplementary information, a control system 133 may not control the surgical instrument 3290 correctly for the given condition of the tissue in situations where the tissue condition is ambiguous based on the measurement value for various electrical and/or physical characteristics of the tissue. Therefore, the presently described control system supplements the electrical and/or physical characteristic(s) sensed by the sensor(s) 3288 with a tissue parameter(s) sensed via the imaging system 142 in order to accurately ascertain the state or condition of the tissue and then control the surgical instrument 3290 in an appropriate manner. For example, different manners of controlling a surgical instrument 3290 could be appropriate in response to detecting an increase in the tissue temperature (i.e., the second tissue parameter received 3304 during the process 3300) localized to the end effector 3292 of the surgical instrument 3290. If the control system 133 detects a corresponding change in the polarization or refractivity of the tissue (i.e., the first tissue parameter received 3302 during the process 3300), then the control circuit 132 can determine 3306 that the tissue is suffering from collateral thermal damage and control 3308 the surgical instrument 3290 to decrease the instrument power level or provide a suggestion to the user to decrease the instrument power level. Conversely, if no corresponding change in the polarization or refractivity of the tissue is detected, then the control circuit 132 can determine 3306 that the tissue is not suffering from collateral thermal damage and control 3308 the surgical instrument 3290 to maintain or increase the instrument power level or provide a suggestion to this effect. As another example, different manners of controlling a surgical instrument 3290 could be appropriate in response to detecting the tissue impedance (i.e., the second tissue parameter received 3304 during the process 3300) for the tissue grasped by the end effector 3292 of the surgical instrument 3290. If the control system 133 detects no change in the tissue impedance while the imaging system 142 visualizes movement, creep, or compression of the tissue (i.e., the first tissue parameter received 3302 during the process 3300), then the control circuit 132 can determine 3306 that there is a subsurface irregularity in the grasped tissue.

The control system 133 described herein can be, for example, implemented on or executed by surgical instrument 3290, a surgical hub 2236 (FIG. 21) to which a surgical instrument 3290 (e.g., an energy device 3241 as shown in FIG. 21) is communicably couplable, or a combination thereof (e.g., using a distributed processing protocol). When the control system is embodied as a component of a surgical instrument 3290, the imaging data can be received by either directly from the imaging system 142 or through a surgical hub 2106, 2236 (FIGS. 17-19), which is in turn coupled to an imaging system 142. When the control system 133 is embodied as a component of a surgical hub 2106, 2236, the imaging data can be received from an imaging system 142 coupled to the surgical hub 2106, 2236, the surgical instrument sensor data can be received from the surgical instrument 3290 coupled to the surgical hub 2106, 2236, and then the control system 133 of the surgical hub 2106, 2236 can determine the appropriate surgical instrument control adjustments and transmit them to the surgical instrument 3290 for execution thereby.

Adaptive Optics to Compensate for Imaging Artifacts

In one aspect, a control system, such as the control system 133 described in connection with FIG. 2, can be configured to compensate for imaging artifacts associated with the imaging system 142 coupled thereto. In one aspect, the control system 133 can be configured to adjust the optical signal received by the imaging system 142 across multiple light wavelengths in combination with selective imaging segment selection within a sample rate above 60 Hz to remove optical particulate obstructions from visualization. In one aspect, the control system 133 can be configured to emit a projected control beam (e.g., via the imaging system 142) and correspondingly monitor the return signal on an isolated frame of the scanning array (e.g., of the image sensor 135) to determine the distortion of the EMR/light by particulates within the gasses occupying the body cavity. The variance of the control projection from its source would give the control system 133 a baseline by which to adjust the scope visualization frames in a later portion of the scan.

Surgical System Control Based on Airborne Particulate Characteristics

One issue inherent to surgical procedures using electrosurgical instruments is the smoke generated by the instruments. Surgical smoke can include toxic gas and vapors; bioaerosols, including dead and living cell material, blood fragments, and viruses; and mutagenic and carcinogenic compounds. Therefore, it is highly desirable to remove these particulates from the surgical site and, accordingly, smoke evacuators are generally utilized in surgical procedures that result in the generation of surgical smoke. However, it would be desirable to control smoke evacuators and other surgical devices (including surgical instruments) according to the type(s) of particulates being generated because different particulate types may necessitate different types of control adjustments to precisely control and mitigate the generation of smoke during the surgical procedure. A surgical system could, e.g., change the surgical instrument energy profile to generate less smoke and/or automatically control the smoke evacuator according to the type of particulate being generated.

In one general aspect, the present disclosure is directed to a control system configured to detect the level of polarization of light emitted by an imaging system to determine a parameter of a particulate cloud and adjust the control parameters of a linked system or device accordingly. In one further aspect, the polarization of the EMR reflected from the detected particulates can be utilized in combination with the vectorization and quantity of the generated particulates to determine the source of the particulates, which can in turn be utilized to control the device(s) causing the generation of the particulates to improve visualization at the surgical site. In one further aspect, the polarization of the EMR reflected from the detected particulates could be utilized to determine whether adjusting the control parameters of an electrosurgical instrument or a smoke evacuator would be more effective at improving visualization at the surgical site.

FIG. 32 is a diagram of a polarizing EMR source 3500 for detecting different particulate types, in accordance with at least one aspect of the present disclosure. The polarizing EMR source 3500 can include an emitter 3502 configured to emit EMR 3506 and a polarizing filter 3504 configured to polarize the emitted EMR 3506. The polarizing filter 3504 can be removably affixable or integrally affixed to the emitter 3502. The polarizing EMR source 3500 can be embodied as a component of an imaging system, which can include the surgical visualization system 100 shown in FIG. 1, the imaging system 142 shown in FIG. 2, and/or the surgical visualization system 500 shown in FIG. 5, for example. Correspondingly, the emitter 3502 can include the emitter 106 shown in FIG. 1, the structured light source 152 shown in FIG. 2, the spectral light source 150 shown in FIG. 2, and so on. The imaging system can in turn be embodied as a component of a surgical system, such the robotic surgical system 110 shown in FIG. 1, which can further include a control system configured to control various aspects of the surgical system. The control system can include the control system 133 shown in FIG. 2 and/or the control system 600 shown in FIG. 11, for example.

During a surgical procedure, airborne particulates may be present at the surgical site. These particulates can include both naturally occurring particulates and non-natural or synthetic particulates. Naturally occurring particulates can be generated due to the interactions between the surgical instruments, such as an electrosurgical instrument, and the tissue being treated. Naturally occurring particulates can include, for example, dead and living cell material, blood fragments, and other biological material. Man-made or synthetic particulates can be introduced to the surgical site by surgical staff. These particulates can be embodied as smoke or aerosols present within or at the surgical site. Generally speaking, the presence of such particulates can be undesirable, so many surgical systems include a smoke evacuator to remove undesired smoke or aerosols from the surgical site. However, the imaging system can be configured to detect the particulates (i.e., smoke) generated at the surgical site and the control system can be configured to control various operational parameters of the surgical system or components thereof based on the characteristics or properties of the detected particulates. Some examples of such control algorithms are described herein.

Referring back to FIG. 32, as noted above, airborne particulates at a surgical site can include both naturally occurring particulates 3510 and man-made particulates 3512. It can be beneficial to be able to distinguish between the different types of particulates present at the surgical site because different actions may be needed to mitigate the presence of each of the different types of particulates. For example, if the detected particulate types are naturally occurring particulates 3510, which can be created from an electrosurgical instrument treating a tissue, then it may be desirable to control the electrosurgical instrument to mitigate the generation of the naturally occurring particulates 3510 (e.g., by decreasing the energy duty cycle or otherwise altering the energy delivery profile of the instrument). Conversely, if the detected particulate types are synthetic particulates 3512, then controlling the electrosurgical instrument would have no effect on the presence of the synthetic particulates 3512 since that particulate type is not generated by the action of the electrosurgical instrument. Instead, it may be desirable to increase the suction flow rate of a smoke evacuator to clear the synthetic particulates 3512 from the surgical site. Further, if a combination of different particulate types are detected at the surgical site, then it could be desirable to control the electrosurgical instrument and the smoke evacuator in combination with each other, with varying control adjustments for each device. Accordingly, a control system for a surgical system can be configured to detect the different types of airborne particulates present at the surgical site and control the various devices or components of the surgical system appropriately to mitigate or eliminate the particulates from the surgical site.

In one aspect, naturally occurring particulates 3510 and synthetic particulates 3512 can be distinguished from each other based upon the reflective characteristics of the airborne particulates 3510, 3512 when subject to polarized EMR 3506. For example, a control system 133 can be configured to cause the emitter 3502 to pulse coherent EMR, with and without polarization, at multiple different wavelength in order to determine the distance to the body that is subject to the surgical procedure and define a range gate so that the control system 133 is only taking depolarization measurements from EMR 3506 reflected from particulates within the air space between the emitter 3502 and the body cavity and not from the body cavity itself. In particular, the control system 133 can be configured to cause the emitter 3502 to pulse coherent EMR at a first wavelength and a second wavelength. The first wavelength can be selected such that the EMR at the first wavelength is substantially non-interactive with naturally occurring particulates 3510 and synthetic particulates 3512 and can therefore penetrate smoke and be reflected from the body cavity. The control system 133 can then determine the distance to the body cavity via, for example, a time-of-flight sensor system 1104, 1204, as described in connection with FIGS. 14-16, according to the difference in time between when the EMR is emitted and when the reflected EMR is detected. The second wavelength can be selected such that the EMR at the second wavelength is substantially interactive with naturally occurring particulates 3510 and synthetic particulates 3512 and can therefore be utilized to detect or measure characteristics associated with the different particulate types. Accordingly, the control system 133 can utilize the body cavity distance determined by pulsing EMR at the first wavelength to range gate the measurements received by the EMR at the second wavelength to ensure only that measurements are being taken of airborne particulates. The control system 133 can then determine whether the airborne particulates are naturally occurring particulates 3510 and/or synthetic particulates 3512 based on the reflective characteristics of the airborne particulates 3510, 3512 and control the other components of the surgical system accordingly.

In one aspect, a control system can be configured to control one or more operational parameters associated with the surgical system based on the type of airborne particulates detected at a surgical site. Example of such algorithms are shown in FIG. 33A, which is a logic flow diagram of a process 3600 for controlling a surgical system according to detected particulate types, and FIG. 33B, which is a logic flow diagram of a process 3650 for controlling a surgical system according to detected particulate types detected within a defined range gate. In the following description of the processes 3600, 3650, reference should also be made to FIG. 2. The processes 3600, 3650 can be embodied as, for example, instructions stored in a memory 134 coupled to a control circuit 132 that, when executed by the control circuit 132, cause the control circuit 132 to perform the enumerated steps of the processes 3600, 3650. For brevity, the processes 3600, 3650 are described as being executed by the control circuit 132; however, it should be understood that the processes 3600, 3650 can be executed by other combinations of hardware, software, and/or firmware.

Turning now specifically to FIG. 33A, the control circuit 132 executing the process 3600 can cause an imaging system 142 to emit 3602 polarized EMR directed at a surgical site via, for example, the polarizing EMR source 3500.

Accordingly, the control circuit 132 can receive 3604 the polarized EMR reflected from the airborne particulates at the surgical site (e.g., within the body cavity) and determine 3606 whether the detected particulate type is a naturally occurring particulate 3510 or a man-made particulate 3512. The control circuit 132 can differentiate between the different types of airborne particulates 3510, 3512 due to their different reflective characteristics when subject to polarized EMR. In particular, one of the types of the airborne particulates 3510, 3512 (e.g., man-made particulates 3512) could scatter polarized EMR at a higher rate than the other type (e.g., naturally occurring particulates 3510). This would decrease the degree of visualization of the scattering airborne particulate type or otherwise affect the manner in which the reflected EMR is received by the image sensor 135 of the imaging system 142. Therefore, this difference in visualization of the different types of airborne particulates 3510, 3512 can be characterized and utilized to identify the types of airborne particulates 3510, 3512 present at the surgical site (e.g., within the body cavity).

Accordingly, if the particulates are naturally occurring particulates 3510, then the process 3600 can proceed along the YES branch and the control circuit 132 can adjust 3608 a control parameter of the surgical system to a first state corresponding to naturally occurring particulates 3510. Conversely, if the particulates are man-made particulates 3512, then the process 3600 can proceed along the NO branch and the control circuit 132 can adjust 3610 the control parameter of the surgical system to a second state corresponding to man-made particulates 3512.

In another aspect, there could be various combinations of naturally occurring particulates 3510 and man-made particulates 3512 present within the body cavity. In such a case, the control circuit 132 could instead determine a relative ratio of the types of airborne particulates 3510, 3512 present within the body cavity (e.g., due to the relative degree by which visualization is reduced or impacted) and then control a surgical device or combination of surgical devices accordingly.

In yet another aspect, a control system can be configured to range gate the measurements and/or visualization based on the polarizing EMR source 3500. Such an aspect can be embodied by the process 3650 illustrated in FIG. 33B.

Accordingly, the control circuit 132 executing the process 3650 can cause the imaging system 142 to emit 3652 EMR at a first wavelength directed at a surgical site via, for example, a structured light source 152 and/or a spectral light source 150. In one aspect, the first wavelength can be a wavelength that is substantially non-interactive with the naturally occurring particulates 3510 and synthetic particulates 3512 that are to be imaged by the imaging system 142.

Accordingly, the control circuit 132 can, via the imaging system 142, receive 3654 the EMR reflected from the body cavity (i.e., surgical site) and define 3656 a range gate corresponding to the airspace between the emitter(s) of the imaging system 142 and the body cavity surface, as is described above.

Accordingly, the control circuit 132 can cause the imaging system 142 to emit 3658 polarized EMR at a second wavelength directed at a surgical site via, for example, a polarizing EMR source 3500. In one aspect, the second wavelength can be a wavelength that is substantially interactive with the naturally occurring particulates 3510 and synthetic particulates 3512 that are to be imaged by the imaging system 142.

Accordingly, the control circuit 132 can, via the imaging system 142, receive the polarized EMR reflected within the defined range gate, which could correspond to the airborne particulates 3510, 3512 located between the emitter(s) of the imaging system 142 and the body cavity surface. The control circuit 132 can then determine 3662 whether the detected particulate type is a naturally occurring particulate 3510 or a man-made particulate 3512 and adjust 3608, 3610 a control parameter of the surgical system to a first state or a second state, as is described above with respect to the process 3600 shown in FIG. 33A.

In another aspect, the surgical system can further be configured to track the movement of the airborne particulates throughout the course of a surgical procedure, which can in turn be utilized to characterize the movement and change in size or configuration of a cloud defined by the airborne particulates. By characterizing the movement of the airborne particulates over time, the surgical system can, for example, determine how well the smoke evacuation of the body cavity is performing and then adjust or provide recommendations to the user to adjust the location or magnitude of smoke evacuation or insufflation. For example, the surgical system could deactivating a first smoke evacuator or first insufflator and activate a second smoke evacuator or second insufflator to adjust the gaseous circulation currents within the body cavity and thereby mitigate any eddies within the body cavity (i.e., areas where the movement vectors of the particulates and/or gasses are zero or near zero) to improve smoke evacuation performance. As another example, the surgical system could adjust a motor or fan level of a smoke evacuator or insufflator to improve smoke evacuation performance.

In one aspect, the control system 133 can be configured to track and characterize the movement of airborne particulates by characterizing the detection of particulates across the cells or pixels of an image sensor 135. In particular, the control system 133 can determine at which pixels the image sensor 135 has detected particulates and then track the movement of the particulates over time across the pixel array of the image sensor 135. In one aspect, the control system 133 can be configured to divide an image obtained via an image sensor 135 into two or more pixel array sections, generate a movement vector corresponding to the generalized change in position by the detected airborne particulates from a first time instance to a second time instance, and then characterize the movement or change in configuration of the particulate cloud accordingly.

For example, FIGS. 34A-C illustrate a pixel array 3700 of an image sensor 135 that consists of a number of pixels 3701. Further, FIGS. 34A-C indicate the change in detected particulate position over time and a generalized particulate cloud movement vector calculated therefrom. It should be noted that although the pixel array 3700 is depicted as being a 5×5 array, this is simply for illustrative purposes and neither the image sensor 135 nor a selected subsection of the pixels thereof are restricted to being a 5×5 array. In the following description of FIGS. 34A-C, reference should also be made to FIG. 2.

FIG. 34A illustrates the detection array 3700 at time $t_1$, which indicates the detection of a first particulate 3702a, second particulate 3702b, third particulate 3702c, fourth particulate 3702d, and fifth particulate 3702e at the indicated pixels 3701 of the image sensor 135. FIG. 34B illustrates the detection array 3700 at time $t_2$, which indicates that the first and fifth particulates 3702a, 3702e have not changed positions and the second, third, and fourth particulate 3702b, 3702c, 3702d have been detected at different pixels 3701 of the image sensor 135. Based on the detected movements of the particulates, the control circuit 132 can be configured to determine a vector representation of the movement of each of the pixels. The vector representations can include both a direction and a magnitude. Based on the directions and magnitudes of the movement vectors, the control circuit 132 can be further configured to calculate (e.g., using vector addition) a vector 3704 corresponding to the generalized movement of the cloud defined by the detected particulates. Accordingly, the control circuit 132 can track the change in a particulate cloud or aerosol from a first state 3710 (e.g., a first position or a first size) to a second state 3712 (e.g., a second position or a second size), as shown in FIG. 35, according to the vector 3704 calculated from the change in pixels of the image sensor 135 at which the particulates are detected.

In one aspect, a control circuit 132 coupled to the image sensor 135 can be configured to track the movements of detected airborne particulates, calculate a generalized movement vector corresponding to the changes in position of the detected airborne particulates within the pixel array 3700 (which can represent the entire pixel array of the image sensor 135 or a subsection thereof), and then control various connected surgical devices, such as insufflators, smoke evacuators, and/or surgical instruments accordingly. In one aspect, the control system 133 including the control circuit 132 can be embodied as a surgical hub 2106, 2236 as described above under the heading SURGICAL HUB SYSTEM. In this aspect, the surgical devices can be communicatively connected to (e.g., paired with) a surgical hub 2106, 2236 and controlled according to the described systems and processes.

In another aspect, the control system 133 can be configured to utilize Raman spectroscopy techniques to determine vibrational/rotational aspects of the airborne particulates using, for example, near IR, UV, or a combination of near IR and UV wavelengths. Data derived from such techniques could, for example, provide information on the gas phase species (e.g., benzenes vs. aldehydes), which in turn could give insights into the type of tissue from which the particulates were generated or to the efficiency of the energy being applied to the tissue. The control system 133 can include, for example, a filter (e.g., a bandpass or notch filter) coupled to the detector to filter out elastic scattering of the source EMR, since the desired information of the species is contained in the inelastic scattering of the EMR. The signals generated by the image sensor 135 or another such detector (e.g., a CCD detector) according to the Raman spectroscopy techniques can be based on the intrinsic structural properties of the detected molecules. In particular, Raman spectroscopy is based on the concept that, e.g., a photon emitted by an appropriate emitter excites a molecule to a higher energy state, which causes the scattered photon to change frequency as a result of conserving energy from the vibrational/rotational change in the molecule. This change in frequency of the scattered photon can be utilized to characterize the type of molecule with which the photon interacted with by comparing the detected signal with pre-characterized data for a given excitation frequency according to the particular type of monochromatic light source utilized. The determined molecule type of the particulates could be utilized for a number of different applications, including providing specific data on relative amounts of potentially hazardous molecules being generated at the surgical site for safety monitoring purposes. The determined molecule type of the particulates could also be utilized to assess the effectiveness and health of the smoke evacuator system or a filter thereof.

Surgical System Control Based on Smoke Cloud Characteristics

One issue inherent to surgical procedures using electrosurgical instruments is the smoke generated by the instruments. Surgical smoke can include toxic gas and vapors; bioaerosols, including dead and living cell material, blood fragments, and viruses; and mutagenic and carcinogenic compounds. Therefore, it is highly desirable to remove these particulates from the surgical site and, accordingly, smoke evacuators are generally utilized in surgical procedures that result in the generation of surgical smoke. However, it would be desirable to control smoke evacuators and other surgical devices (including surgical instruments) according to the amount of smoke at the surgical site, the variation in the smoke cloud over time (e.g., whether a smoke cloud is actively accumulating or diminishing), and other such smoke cloud characteristics in order to precisely control and mitigate the generation of smoke during the surgical procedure. A surgical system could, e.g., change the surgical instrument energy profile to generate less smoke and/or automatically control the smoke evacuator according to the amount of surgical smoke being generated.

In one general aspect, the present disclosure is directed to a surgical system configure to detect and characterize amorphous, three-dimensional particulate clouds generated during surgical procedures. The surgical system can be configured to detect the movements of the particulate cloud within the abdominal cavity and relative to the surgical site and then control various surgical devices, such as surgical instruments or a smoke evacuator, accordingly. In one general aspect, the present disclosure is directed to a control system configured to define a surface or boundary of a cloud or particulate cluster generated during a surgical procedure and analyze various characteristics of the defined cloud, such as the direction and rate-of-change of the boundary, to control various control parameters of a surgical system, such as the power level of a surgical instrument/generator or smoke evacuation motor control. In one further aspect, the control system can be configured to develop the boundary by defining a predefined density of the particulates based on the overall volume of the particulates or the size of the particulates. In another further aspect, the rate-of-change of the particulate cloud surface boundary can be utilized to directionally define the rate of change of the energy device or the smoke evacuation mechanism.

FIG. 36 is a diagram of a surgical system 3750 during the performance of a surgical procedure in which a particulate cloud 3752 is being generated, in accordance with at least one aspect of the present disclosure. The surgical system 3750 can be embodied as a robotic surgical system, such as the robotic surgical system 110 shown in FIG. 1, for example. The surgical system 3750 can include an electrosurgical instrument 3754, a smoke evacuator 3756, a grasper 3750, and any other surgical devices for treating, cutting, or otherwise manipulating a tissue 3760 for a surgical procedure. Although not shown in FIG. 36, the surgical system 3750 can further include an imaging system, which can include the surgical visualization system 100 shown in FIG. 1, the imaging system 142 shown in FIG. 2, and/or the surgical visualization system 500 shown in FIG. 5, for example. The surgical system 3750 can still further include a control system, which can include the control system 133 shown in FIG. 2 and/or the control system 600 shown in FIG. 11, for example.

During a surgical procedure, airborne particulates 3751 may be generated due to the interactions between the surgical instruments, such as an electrosurgical instrument 3754, and the tissue 3760 being treated. These particulates 3751 can be embodied as a cloud 3752 of smoke or an aerosol present within or at the surgical site. Generally speaking, the presence of such particulates 3751 can be undesirable, so many surgical systems 3750 include a smoke evacuator 3756 to remove the particulates 3751 from the surgical site. However, the imaging system can be configured to image the particulates 3751 and/or smoke generated at the surgical site and the control system can be configured to control various operational parameters of the surgical system 3750 or components thereof based on the characteristics or properties of the imaged smoke. Some examples of such control algorithms are described herein.

In one aspect, a control system can be configured to control one or more operational parameters associated with the surgical system 3750 based on one or more characteristics associated with a smoke cloud generated at a surgical site. One example of such an algorithm is shown in FIG. 37, which is a logic flow diagram of a process 3800 for controlling a surgical system according to particulate cloud characteristics. In the following description of the process 3800, reference should also be made to FIG. 2. The process 3800 can be embodied as, for example, instructions stored in a memory 134 coupled to a control circuit 132 that, when executed by the control circuit 132, cause the control circuit 132 to perform the enumerated steps of the process 3800. For brevity, the process 3800 is described as being executed by the control circuit 132; however, it should be understood that the process 3800 can be executed by other combinations of hardware, software, and/or firmware.

Accordingly, the control circuit 132 executing the process 3800 can detect 3802 the presence of airborne particulates within the FOV of the imaging system 142 using any of the techniques described above. In general, the image sensor 135 of the imaging system 142 can detect EMR emitted by a structured light source 152 and/or a spectral light source 150 and reflected by the airborne particulates to detect/image the particulates.

Accordingly, the control circuit 132 can characterize 3804 the particulate cloud defined by the detected particulates. In one aspect, the control circuit 132 can be configured to define a three-dimensional boundary of the particulate cloud to delineate an amorphous, three-dimensional construct whose density, volume, position, movement, and/or boundaries can be tracked over time. The boundary of the particulate cloud at the surgical site can be defined in a variety of different manners. For example, the particulate cloud boundary can be defined as the volume encompassing all of the airborne particulates detected within the FOV of the imaging system 142. As another example, the particulate cloud boundary can be defined as the volume having a threshold density of airborne particulates.

Accordingly, the control circuit 132 can determine 3806 whether one or more characteristics of the particulate cloud violate a threshold. Such tracked characteristics can include, for example, the density of the particulate cloud, volume of the particulate cloud, position of the particulate cloud and/or its boundary, movement of the particulate cloud and/or its boundary, and/or the rate of change or other derivative of any of the aforementioned characteristics. The threshold(s) for the tracked characteristics can be preprogrammed or dependent upon other parameters, such as the surgical context (e.g., the type of surgical procedure being performed). If a threshold is not violated, then the process 3800 can proceed along the NO branch and the control circuit 132 can continue as described above until, for example, a stopping criterion has been satisfied (e.g., the surgical procedure being completed). If a threshold is violated, then the process 3800 can proceed along the YES branch and the control circuit 132 can continue as described below.

Accordingly, the control circuit 132 can adjust 3808 one or more control parameters of the surgical system 3750. The control parameters that are adjustable by the control circuit 132 can include surgical instrument/generator energy level, smoke evacuator suction, visualization parameters, and so on. For example, FIG. 38 is a series of graphs 3850, 3852, 3854 illustrating the adjustment of control parameters based on particulate cloud characteristics by a control circuit 132 executing the process 3800. The first graph 3850 illustrates a first line 3860 indicating the change in smoke cloud density, represented by the vertical axis 3856, over time, represented by the horizontal axis 3858. The second graph 3852 illustrates a second line 3868 indicating the change in energy duty cycle of an electrosurgical instrument 3754 (or the generator driving the electrosurgical instrument 3754), represented by the vertical axis 3866, over time, represented by the horizontal axis 3858. The third graph 3854 illustrates a third line 3880 indicating the change in the smoke evacuation or suction flow rate of a smoke evacuator 3756, represented by the vertical axis 3878, over time, represented by the horizontal axis 3858. In combination, the graphs 3850, 3852, 3854 illustrate a representative, prophetic implementation of the process 3800 during a surgical procedure, wherein the process 3800 adjusts 3808 the electrosurgical instrument energy duty cycle and smoke evacuator suction flow rate control parameters according to the characterized smoke cloud density.

Initially, the electrosurgical instrument 3754 is not applying energy to the captured tissue 3760, as indicated by a first graphic 3890. Accordingly, the energy duty cycle of the electrosurgical instrument 3754 is zero, the smoke evacuator suction flow rate is at a base or default rate, and no smoke is being generated (because no energy is being applied to the tissue 3760). At time $t_1$, the surgeon activates the electrosurgical instrument 3754 and begins applying energy to the tissue 3760, represented by the energy duty cycle increasing 3870 from zero to $E_3$. Due to the application of energy to the tissue 3760, smoke begins to be generated at the surgical site, represented by the smoke cloud density sharply increasing 3862 from zero a period of time after $t_1$. Further, in response to the energy being activated, the smoke evacuator flow rate can be increased 3882 by the control circuit 132 from $Q_1$ to $Q_2$ as the smoke evacuator 3756 begins attempting to remove the generated smoke from the surgical site. At this stage, the control circuit 132 can begin detecting 3802 the airborne particulates generated by the application of energy and characterizing 3804 the corresponding smoke cloud defined by the airborne particulates.

At time $t_2$, the application of energy to the tissue 3760 has caused a smoke cloud 3752 to develop at the surgical site, as indicated by a second graphic 3892. The control circuit 132 can determine 3806 that the cloud density has exceeded a smoke cloud density threshold (e.g., as represented by $D_3$). Accordingly, the control circuit 132 adjusts 3808 the electrosurgical instrument energy duty cycle control parameter by decreasing 3872 it from $E_3$ to $E_2$. The control circuit 132 can elect to make this adjustment because applying lower levels of energy to a tissue 3760 can result in less smoke being generated. In response, the smoke cloud density begins decreasing 3864 at time $t_1$.

At time $t_3$, the smoke cloud 3752 has decreased in size, but has not completely dissipated, as indicated by a third graphic 3894. The control circuit 132 can determine 3806 that the cloud density is not decreasing at a fast enough rate or that some other characteristic of the smoke cloud is violating some other threshold. Accordingly, the control circuit 132 again adjusts 3808 the electrosurgical instrument energy duty cycle control parameter by decreasing 3874 it from $E_2$ to $E_1$ in order mitigate further smoke generation.

At time $t_4$, the smoke cloud 3752 has nearly dissipated, as indicated by the fourth graphic 3896. The control circuit 132 can determine 3806 can determine 3806 that the smoke cloud has violated another threshold, such as the cloud density being above a particular level (e.g., as represented by $D_1$) for longer than a threshold period of time (e.g., as represented by $t_4$). Accordingly, the control circuit 132 adjusts the smoke evacuator suction flow rate control parameter by increasing 3884 it from $Q_2$ to $Q_3$ in order to fully remove the smoke particulates from the surgical site.

It should be noted that the implementation of the process 3800 embodied by FIG. 38 is provided for illustrative purposes and simply represents one possible implementation. In particular, different control parameters can be controlled by the process 3800, different thresholds can be utilized, different smoke cloud characteristics can be tracked, and so on. Therefore, FIG. 38 should not be construed to limit the process 3800 of FIG. 37 or any other described systems and methods in any way.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

Various aspects of the subject matter described herein are set out in the following numbered examples.

Example 1. A control system for a surgical system, the control system comprising an imaging system and a control circuit coupled to the imaging system. The imaging system comprises an emitter configured to emit electromagnetic radiation (EMR), a polarizing filter configured to polarize the EMR emitted by the emitter, and an image sensor. The control circuit is configured to detect the polarized EMR reflected from an airborne particulate as received by the image sensor, determine whether a particulate type of the airborne particulate is a naturally occurring particulate or a synthetic particulate based on a reflective characteristic of the polarized EMR, and adjust a control parameter of the surgical system according to the determined particulate type.

Example 2. The control system of Example 1, wherein the surgical system comprises a smoke evacuator and the control parameter comprises at least one of a flow rate, a fan level, or a motor level of the smoke evacuator.

Example 3. The control system of Example 1, wherein the surgical system comprises an electrosurgical instrument and the control parameter comprises at least one of a power level or an energy profile of the electrosurgical instrument.

Example 4. The control system of any one of Examples 1-3, wherein the airborne particulate is one of a plurality of airborne particulates, the image sensor comprises a pixel array, and the control circuit is further configured to detect a change in detection of the plurality of airborne particulates according to the pixel array and characterize a movement of a surgical smoke cloud defined by the plurality of airborne particulates according to the detected change.

Example 5. The control system of Example 4, wherein the control circuit is further configured to determine a quantity of the plurality of airborne particulates, determine vectors of movement of the plurality of airborne particulates, and characterize the movement of the surgical cloud according to the determined quantity and the determined vectors.

Example 6. The control system of any one of Examples 1-5, wherein a surgical hub comprises the control system.

Example 7. A control system for a surgical system, the control system comprising an imaging system and a control circuit coupled to the imaging system. The imaging system comprises multispectral electromagnetic radiation (EMR) source, a polarizing filter configured to polarize EMR emitted by the multispectral EMR source, and an image sensor. The control circuit is configured to detect the polarized EMR reflected from a particulate in an aerosol as received by the image sensor, determine whether a particulate type of the particulate is a naturally occurring particulate or a synthetic particulate based on a reflective characteristic of the polarized EMR, determine whether to adjust a first control parameter or a second control parameter according to the determined particulate type, and adjust the first control parameter or the second control parameter accordingly.

Example 8. The control system of Example 7, wherein the surgical system comprises a smoke evacuator and the first control parameter comprises at least one of a flow rate, a fan level, or a motor level of the smoke evacuator.

Example 9. The control system of Example 7, wherein the surgical system comprises an electrosurgical instrument and the second control parameter comprises at least one of a power level or an energy profile of the electrosurgical instrument.

Example 10. The control system of any one of Examples 7-9, wherein the particulate is one of a plurality of particulates, the image sensor comprises a pixel array, and the control circuit is further configured to detect a change in detection of the plurality of particulates according to the pixel array and characterize a movement of the aerosol defined by the plurality of particulates according to the detected change.

Example 11. The control system of Example 10, wherein the control circuit is further configured to determine a quantity of the plurality of particulates, determine vectors of movement of the plurality of particulates, and characterize the movement of the aerosol according to the determined quantity and the determined vectors.

Example 12. A method for controlling a surgical system, the surgical system comprising an imaging system, the imaging system comprising an emitter configured to emit electromagnetic radiation (EMR), a polarizing filter configured to polarize the EMR emitted by the emitter, and an image sensor. The method comprises detecting the polarized EMR reflected from an airborne particulate as received by the image sensor, determining whether a particulate type of the airborne particulate is a naturally occurring particulate or a synthetic particulate based on a reflective characteristic of the polarized EMR, and adjusting a control parameter of the surgical system according to the determined particulate type.

Example 13. The method of Example 12, wherein the surgical system further comprises a smoke evacuator and the control parameter comprises at least one of a flow rate, a fan level, or a motor level of the smoke evacuator.

Example 14. The method of Example 12, wherein the surgical system further comprises an electrosurgical instrument and the control parameter comprises at least one of a power level or an energy profile of the electrosurgical instrument.

Example 15. The method of any one of Examples 12-14, wherein the airborne particulate is one of a plurality of airborne particulates, the image sensor comprises a pixel array, and the method further comprises detecting a change in detection of the plurality of airborne particulates according to the pixel array and characterizing a movement of a surgical smoke cloud defined by the plurality of airborne particulates according to the detected change.

Example 16. The method of Example 15, wherein the method further comprises determining a quantity of the plurality of airborne particulates, determining vectors of movement of the plurality of airborne particulates, and characterizing the movement of the surgical cloud according to the determined quantity and the determined vectors.

Example 17. The method of any one of Examples 12-16, wherein a surgical hub comprises the surgical system.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A control system for a surgical system, the control system comprising:
    an imaging system comprising:
        an emitter configured to emit a first electromagnetic radiation (EMR) having a first wavelength and a second EMR having a second wavelength;
        a polarizing filter configured to polarize the second EMR emitted by the emitter; and
        an image sensor; and
    a control circuit coupled to the imaging system, the control circuit configured to:
        detect the first EMR reflected from a surface of a surgical site;
        detect the polarized second EMR reflected from an airborne particulate as received by the image sensor based on a detection of the reflected first EMR;
        determine whether a particulate type of the airborne particulate is a naturally occurring particulate or a synthetic particulate based on a reflective characteristic of the polarized EMR; and
        adjust a control parameter of the surgical system according to the determined particulate type.

2. The control system of claim 1, wherein:
the surgical system comprises a smoke evacuator; and
the control parameter comprises at least one of a flow rate, a fan level, or a motor level of the smoke evacuator.

3. The control system of claim 1, wherein:
the surgical system comprises an electrosurgical instrument; and
the control parameter comprises at least one of a power level or an energy profile of the electrosurgical instrument.

4. The control system of claim 1, wherein:
the airborne particulate is one of a plurality of airborne particulates;
the image sensor comprises a pixel array; and
the control circuit is further configured to:
    detect a change in detection of the plurality of airborne particulates according to the pixel array; and
    characterize a movement of a surgical smoke cloud defined by the plurality of airborne particulates according to the detected change.

5. The control system of claim 4, wherein the control circuit is further configured to:
    determine a quantity of the plurality of airborne particulates;
    determine vectors of movement of the plurality of airborne particulates; and
    characterize the movement of the surgical cloud according to the determined quantity and the determined vectors.

6. The control system of claim 1, wherein a surgical hub comprises the control system.

7. A control system for a surgical system, the control system comprising:
    an imaging system comprising:
        a multispectral electromagnetic radiation (EMR) source;
        a polarizing filter configured to polarize EMR emitted by the multispectral EMR source; and
        an image sensor; and
    a control circuit coupled to the imaging system, the control circuit configured to:
        define a range gate for detecting the polarized EMR reflected from a particulate in an aerosol as received by the image sensor;
        determine whether a particulate type of the particulate is a naturally occurring particulate or a synthetic particulate based on a reflective characteristic of the detected polarized EMR;
        determine whether to adjust a first control parameter or a second control parameter according to the determined particulate type; and
        adjust the first control parameter or the second control parameter accordingly.

8. The control system of claim 7, wherein:
the surgical system comprises a smoke evacuator; and
the first control parameter comprises at least one of a flow rate, a fan level, or a motor level of the smoke evacuator.

9. The control system of claim 7, wherein:
the surgical system comprises an electrosurgical instrument; and
the second control parameter comprises at least one of a power level or an energy profile of the electrosurgical instrument.

10. The control system of claim 7, wherein:
the particulate is one of a plurality of particulates;
the image sensor comprises a pixel array; and
the control circuit is further configured to:
    detect a change in detection of the plurality of particulates according to the pixel array; and
    characterize a movement of the aerosol defined by the plurality of particulates according to the detected change.

11. The control system of claim 10, wherein the control circuit is further configured to:
    determine a quantity of the plurality of particulates;
    determine vectors of movement of the plurality of particulates; and
    characterize the movement of the aerosol according to the determined quantity and the determined vectors.

12. A method for controlling a surgical system, the surgical system comprising an imaging system, the imaging system comprising an emitter configured to emit electromagnetic radiation (EMR), a polarizing filter configured to polarize the EMR emitted by the emitter, and an image sensor, the method comprising:
    detecting the polarized EMR reflected from an airborne particulate as received by the image sensor;
    determining whether a particulate type of the airborne particulate is a naturally occurring particulate or a synthetic particulate based on a reflective characteristic of the polarized EMR, wherein the imaging system is configured to exclude interactions with a surface of the body cavity from the reflective characteristic of the polarized EMR; and adjusting a control parameter of the surgical system according to the determined particulate type.

13. The method of claim 12, wherein:

the surgical system further comprises a smoke evacuator; and the control parameter comprises at least one of a flow rate, a fan level, or a motor level of the smoke evacuator.

14. The method of claim 12, wherein:

the surgical system further comprises an electrosurgical instrument; and the control parameter comprises at least one of a power level or an energy profile of the electrosurgical instrument.

15. The method of claim 12, wherein:

the airborne particulate is one of a plurality of airborne particulates;

the image sensor comprises a pixel array; and the method further comprises:

detecting a change in detection of the plurality of airborne particulates according to the pixel array; and characterizing a movement of a surgical smoke cloud defined by the plurality of airborne particulates according to the detected change.

16. The method of claim 15, wherein the method further comprises:

determining a quantity of the plurality of airborne particulates;

determining vectors of movement of the plurality of airborne particulates; and characterizing the movement of the surgical cloud according to the determined quantity and the determined vectors.

17. The method of claim 12, wherein a surgical hub comprises the surgical system.

* * * * *